US011254638B2

(12) United States Patent
Kanbara et al.

(10) Patent No.: US 11,254,638 B2
(45) Date of Patent: Feb. 22, 2022

(54) NITRILEOXIDE COMPOUND

(71) Applicants: DAIKIN INDUSTRIES, LTD., Osaka (JP); TOKYO INSTITUTE OF TECHNOLOGY, Tokyo (JP)

(72) Inventors: Tadashi Kanbara, Settsu (JP); Tsuyoshi Noguchi, Settsu (JP); Toshikazu Takata, Tokyo (JP); Hiromitsu Sogawa, Tokyo (JP); Shunsuke Monjiyama, Tokyo (JP); Toyokazu Tsutsuba, Tokyo (JP)

(73) Assignees: DAIKIN INDUSTRIES, LTD., Osaka (JP); TOKYO INSTITUTE OF TECHNOLOGY, Tokyo (JP)

( * ) Notice: Subject to any disclaimer, the term of this patent is extended or adjusted under 35 U.S.C. 154(b) by 0 days.

(21) Appl. No.: 16/732,996

(22) Filed: Jan. 2, 2020

(65) Prior Publication Data
US 2020/0140377 A1    May 7, 2020

Related U.S. Application Data

(62) Division of application No. 15/556,806, filed as application No. PCT/JP2016/057646 on Mar. 10, 2016, now Pat. No. 10,562,846.

(30) Foreign Application Priority Data

Mar. 10, 2015  (JP) ................. 2015-047771

(51) Int. Cl.
| C07C 291/06 | (2006.01) |
| C08G 63/08 | (2006.01) |
| C08L 101/02 | (2006.01) |
| C08G 63/91 | (2006.01) |
| C08K 5/32 | (2006.01) |
| C08G 63/16 | (2006.01) |
| C08F 120/36 | (2006.01) |
| C08G 63/685 | (2006.01) |

(52) U.S. Cl.
CPC .......... *C07C 291/06* (2013.01); *C08F 120/36* (2013.01); *C08G 63/08* (2013.01); *C08G 63/16* (2013.01); *C08G 63/6856* (2013.01); *C08G 63/91* (2013.01); *C08G 63/916* (2013.01); *C08K 5/32* (2013.01); *C08L 101/02* (2013.01)

(58) Field of Classification Search
CPC ................................................. C07C 291/06
See application file for complete search history.

(56) References Cited

U.S. PATENT DOCUMENTS

| 9,670,134 B2 * | 6/2017 | Sathiosatham ....... C07C 201/12 |
| 9,676,957 B2 | 6/2017 | Brutto et al. |
| 2013/0217850 A1 | 8/2013 | Tanaka et al. |
| 2015/0251995 A1 | 9/2015 | Kanbara et al. |
| 2015/0322281 A1 | 11/2015 | Brutto et al. |
| 2016/0002153 A1 | 1/2016 | Kanbara et al. |

FOREIGN PATENT DOCUMENTS

| CN | 102942430 A | 2/2013 | |
| CN | 104530417 A | 4/2015 | |
| DE | 2218785 A1 | 4/1973 | |
| JP | 2010-037289 A | 2/2010 | |
| JP | 2013-112741 A | 6/2013 | |
| WO | 2014/092914 A1 | 6/2014 | |
| WO | WO-2014092914 A1 * | 6/2014 | ........... C09D 133/12 |
| WO | 2014/136952 A1 | 9/2014 | |

OTHER PUBLICATIONS

Marsh, Organic Letters, 2007, vol. 9, No. 14, p. 2613-2616 (Year: 2007).*
Bowman, Journal of the Chemical Society, Perkin Transactions 2: Physical Organic Chemistry (1972-1999) (1991), (1), 73-80 (Year: 1991).*
Shen, Synthetic Communications, 2007, 37(20), p. 3677-3687. (Year: 2007).*
Yao, Tetrahedron Letters, vol. 38, No. 36, p. 6419-6420, 1997 (Year: 1997).*
Kao, Tetrahedron, 54, p. 13997-14014, 1998. (Year: 1998).*
Tanaka, Journal of Applied Polymer Science, vol. 8, p. 1787-1799 (1964) (Year: 1964).*
Ching-Fa Yao et al., "Generation of Nitroalkanes, Hydroximoyl Halides and Nitrile Oxides from the Reactions of Beta-Nitrostyrenes with Grignard or Organolithium Reagents", Tetrahedron, Elsevier Science Publishers, Amsterdam, NL, vol. 54, No. 5-6, 1998, pp. 791-822, XP004106605 (32 pages total).
Chen-Gang Wang et al., "Polymer nitrile N-oxides directed toward catalyst- and solvent-free click grafting", ChemComm, vol. 49, No. 70, Jan. 1, 2013 (Jan. 1, 2013), pp. 7723-7725, XP055492296 (3 pages total).
Extended European Search Report dated Jul. 25, 2018 issued by the European Patent Office in counterpart application No. 16761836.2.
International Preliminary Report on Patentability with the translation of Written Opinion dated Sep. 21, 2017 in International application No. PCT/JP2016/057646.

(Continued)

Primary Examiner — Robert C Boyle
(74) Attorney, Agent, or Firm — Sughrue Mion, PLLC

(57) ABSTRACT

A compound of the formula (III):

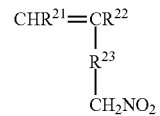

wherein $R^{21}$ is a hydrogen atom or an alkyl group; $R^{22}$ is a hydrogen atom or an alkyl group; and $R^{23}$ is a divalent organic group.

1 Claim, No Drawings

(56) References Cited

OTHER PUBLICATIONS

International Search Report for PCT/JP2016/057646 dated Jun. 7, 2016 [PCT/ISA/210].
Jeffrey W. Bode, et al., "Stereoselective Syntheses of Epothilones A and B via Nitrile Oxide Cycloadditions and Related Studies", J. Org. Chem, 2001, pp. 6410-6424, vol. 66.
Yasuhito Koyama, et al., Japanese Journal of Polymer Science and Technology, 2011, pp. 14-159, vol. 68, No. 4.
Takahashi, Journal of Applied Polymer Science, vol. 12, p. 1683-1695 (1968) (Year: 1968).

* cited by examiner

NITRILEOXIDE COMPOUND

CROSS-REFERENCE TO RELATED APPLICATIONS

This application is a Rule 53(b) Divisional of U.S. application Ser. No. 15/556,806, filed Sep. 8, 2017, which is a National Stage of International Application No. PCT/JP2016/057646, filed Mar. 10, 2016, which claims priority from Japanese Patent Application No. 2015-047771, filed Mar. 10, 2015, the contents of all of which are incorporated herein by reference in their entirety.

TECHNICAL FIELD

The present invention relates to a nitrileoxide compound, and a polymer comprising the nitrileoxide compound.

BACKGROUND ART

A compound having a nitrileoxide group is known to be useful as a reaction agent in various applications since it readily click-reacts with an unsaturated bond in other compound ([2+3] cycloaddition reaction).

With respect to the known nitrileoxide compound, Patent Literature 1 discloses an aromatic nitrileoxide compound and Patent Literature 2 discloses an aliphatic nitrileoxide compound, as a compound having low molecular weight. Patent Literature 3 discloses an acrylate or styrene-based polymer having a nitrileoxide group as a compound having high molecular weight.

On the other hand, a polymeric material is an important compound used in a wide range of applications. In particular, a fluorine-containing polymeric material is widely used as an electronic member or a member of a semiconductor manufacturing process equipment. As the means for curing the polymeric material, usually a crosslinking agent (or a curing agent) has been used.

PRIOR ART LITERATURE

Patent Literature

Patent Literature 1: Japanese Patent Application No. 2010-37289
Patent Literature 2: International Publication No. 2014/136952
Patent Literature 3: Japanese Patent Application No. 2013-112741

SUMMARY OF THE INVENTION

Problem to be Solved by the Invention

The polymeric material may contain a crosslinking agent unreacted as an impurity when the polymeric material is cured with a conventional crosslinking agent. The conventional crosslinking agent has a low molecular weight. When the polymeric material containing such impurity is used as a member of a semiconductor manufacturing process equipment, outgases are generated, thereby causing problems such as process errors.

Therefore, the object of the present invention is to provide a polymeric material which contains a small amount of low molecular weight impurities when is cured.

Means to Solve the Problem

As a result of intensively studying of the inventors of the present invention in order to solve the above problem, the inventors have found that the problem can be solved by using a self-crosslinking polymer capable of crosslinking without using the crosslinking agent. The inventors of the present invention have focused a nitrileoxide compound causing a click reaction, and have studied a polymer having a nitrileoxide group. The inventors of the present invention have found that a polymer which is able to cause an intermolecular crosslinking reaction and cure without the need of the conventional crosslinking agent by introducing a plurality of nitrileoxide groups into the molecule of the polymer. In addition, the inventors have found that the polymer having a plurality of nitrileoxide groups in the molecule can be used in place of the conventional crosslinking agent. It is noted that the known polymer having a nitrileoxide group is only a polymer having one nitrileoxide group at the terminal of the acrylate or styrene-based backbone, and since such polymer has only one nitrileoxide group, it cannot crosslink between molecules.

Further, the inventors have also studied a process for producing the polymer having a plurality of nitrileoxide groups. As a result, the inventors have focused a method of synthesizing a polymer by using a monomer having a nitrileoxide group, and have found that by reacting a nitrileoxide monomer having two nucleophilic groups at the molecular terminals as the monomer with a condensation polymerizable or addition polymerizable monomer, the polymer described above can successfully be obtained. In addition, the inventors have found that by performing the polymerization using a compound having a nitrileoxide group and an ethylenic double bond as a monomer, the polymer described above can successfully be obtained.

Furthermore, the inventors have found that the polymer described in Patent Literature 3 is synthesized by performing the polymerization providing a the acrylate or styrene based main chain and using a compound having a nitrileoxide group as a terminator, and the reaction of functionalizing a terminal described in Patent Literature 3 is low efficient. In addition, in this method, it is impossible to introducing a nitrileoxide group into a position other than the terminal of a molecular main chain of a polymer, for example, in central portion, and it is difficult to introducing a nitrileoxide group into both terminals of the molecular main chain.

As a result of intensively studying of the inventors of the present invention with respect to the above problems, the inventors have found that by using a nitrileoxide compound having a nucleophilic group as a polymerization initiator, a nitrileoxide group may efficiently be introduced into the polymer. In addition, the inventors have found that by using this method, it is possible to introduce a nitrileoxide group into the central portion of a molecular main chain of a polymer and to introduce a nitrileoxide group into the both terminals of the polymer.

Therefore, the present invention provides:
(1) A compound of the formula (I):

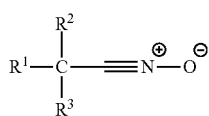

wherein:
$R^1$ is a hydrogen atom or a hydrocarbon group;
$R^2$ is —$R^4$—$R^5$;
$R^3$ is —$R^4$—$R^5$ or —$R^4$—$R^6$;
$R^4$ is a divalent organic group;

$R^5$ is each independently OH, SH, COOH or $NHR^9$;

$R^9$ is a hydrogen atom or an alkyl group having 1-6 carbon atoms; and $R^6$ is a hydrogen atom or an alkyl group having 1-6 carbon atoms;

(2) The compound according to the above (1) wherein $R^2$ and $R^3$ are each independently $—R^4—R^5$;

(3) The compound according to the above (1) wherein $R^2$ is $—R^4—R^5$, and $R^3$ is $—R^4—R^6$;

(4) The compound according to any one of the above (1)-(3) wherein $R^4$ is $—R^{11}—R^{12}—$, $R^{11}$ is an arylene having 3-10 carbon atoms or $—CR^7R^8—$, $R^7$ and $R^8$ are each independently an alkyl group having 1-6 carbon atoms, and $R^{12}$ is, a single bond, a linker having 1-10 atoms of the main chain;

(5) The compound according to any one of the above (1)-(4) wherein $R^1$ is an alkyl group having 1-16 carbon atoms, a cycloalkyl group having 3-20 carbon atoms, an aryl group having 3-20 carbon atoms, or a (poly)alkylether group, which may be substituted by one or more substituents;

(6) The compound according to any one of the above (1)-(5) wherein $R^5$ is OH;

(7) A compound of the formula (III):

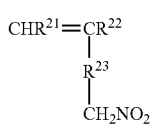

wherein:
$R^{21}$ is a hydrogen atom or an alkyl group;
$R^{22}$ is a hydrogen atom or an alkyl group; and
$R^{23}$ is a divalent organic group;

(8) The compound according to the above (7) wherein $R^{23}$ is $—R^{24}—R^{25}—R^{26}—$;

$R^{24}$ is a single bond, an alkylene having 1-6 carbon atoms, $—CO—$, $—CO—O—$, or $—CO—NR—$ (wherein R is a hydrogen atom or an alkyl group);

$R^{25}$ is a linker having 1-20 atoms of the main chain;

$R^{26}$ is a single bond, an alkylene having 1-6 carbon atoms or $—CR^{27}R^{28}—$; and $R^{27}$ and $R^{28}$ are each independently a hydrogen atom, an alkyl group having 1-6 carbon atoms or an aryl group having 5-10 carbon atoms;

(9) The compound according of the above (8) wherein $R^{24}$ is $—CO—$ or $—CO—O—$;

$R^{25}$ is a linker having 1-20 atoms of the main chain;

$R^{26}$ is $—CR^{27}R^{28}—$;

$R^{27}$ is an aryl group having 5-10 carbon atoms; and $R^{28}$ is a hydrogen atom or an alkyl group having 1-6 carbon atoms;

(10) A copolymer comprising one or more monomer units of the formula (Ia):

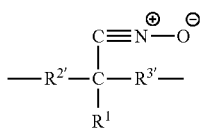

wherein:
$R^1$ is a hydrogen atom or a hydrocarbon group;
$R^{2'}$ and $R^{3'}$ are each independently $—R^4—R^{5'}—$;
$R^4$ is a divalent organic group;
$R^{5'}$ is each independently $—O—$, $—S—$, $—CO—$ or $—NR^9—$; and
$R^9$ is a hydrogen atom or an alkyl group having 1-6 carbon atoms, and one or more condensation polymerizable or addition polymerizable monomer units;

(11) A process of producing the copolymer according to the above (10), comprising a step of polymerizing one or more monomers of the formula (Ia'):

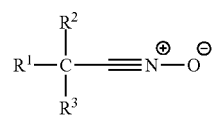

wherein:
$R^1$ is a hydrogen atom or a hydrocarbon group;
$R^2$ and $R^3$ are each independently, $—R^4—R^5$;
$R^4$ is a divalent organic group;
$R^5$ is each independently OH, SH, COOH or $NHR^9$; and
$R^9$ is a hydrogen atom or an alkyl group having 1-6 carbon atoms with one or more condensation polymerizable or addition polymerizable monomers;

(12) A polymer comprising one or more monomer units of the formula (IIa):

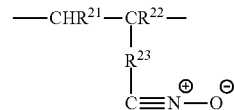

wherein:
$R^{21}$ is a hydrogen atom or an alkyl group;
$R^{22}$ is a hydrogen atom or an alkyl group; and
$R^{23}$ is a divalent organic group;

(13) A polymer comprising one or more monomer units of the formula (IIIa):

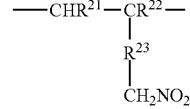

wherein:
$R^{21}$ is a hydrogen atom or an alkyl group;
$R^{22}$ is a hydrogen atom or an alkyl group; and
$R^{23}$ is a divalent organic group;

(14) A process of producing the copolymer according to the above (13), comprising a step of polymerizing one or more monomers of the formula (III):

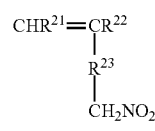

wherein:

R²¹ is a hydrogen atom or an alkyl group;

R²² is a hydrogen atom or an alkyl group; and

R²³ is a divalent organic group;

(15) A process of producing the copolymer according to the above (12), comprising a step of converting the CH₂NO₂ group of the polymer according to the above (13) to a CN⁺O⁻ group by dehydration;

(16) A composition applied to a material containing a group reactive with a nitrileoxide group, comprising one or more polymers according to the above (10) or (12);

(17) The composition according to the above (16), which is a crosslinking agent;

(18) A polymer comprising one or more ring-opening polymerizable monomer units, having a group of the formula (Ib):

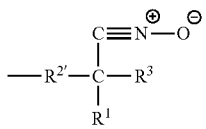

wherein:

R¹ is a hydrogen atom or a hydrocarbon group;

R²′ is —R⁴—R⁵′—;

R³ is —R⁴—R⁶;

R⁴ is a divalent organic group;

R⁵′ is —O—, —S—, —CO—O— or —NR⁹—;

R⁹ is a hydrogen atom or an alkyl group having 1-6 carbon atoms; and

R⁶ is a hydrogen atom or an alkyl group having 1-6 carbon atoms, at one terminal of the main chain;

(19) A polymer comprising one or more ring-opening polymerizable monomer units, having a group of the formula (Ib):

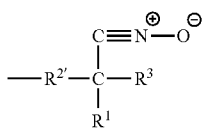

wherein:

R¹ is a hydrogen atom or a hydrocarbon group;

R²′ is —R⁴—R⁵′—;

R³ is —R⁴—R⁶;

R⁴ is a divalent organic group;

R⁵′ is —O—, —S—, —CO—O— or —NR⁹—;

R⁹ is a hydrogen atom or an alkyl group having 1-6 carbon atoms; and

R⁶ is a hydrogen atom or an alkyl group having 1-6 carbon atoms, at one terminal of the main chain and a nitrileoxide group at the other terminal of the main chain;

(20) A polymer comprising one or more ring-opening polymerizable monomer units, having one moiety of the formula (Ic):

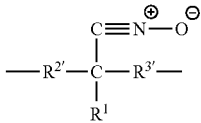

wherein:

R¹ is a hydrogen atom or a hydrocarbon group;

R²′ and R³′ are each independently —R⁴—R⁵′—;

R⁴ is a divalent organic group;

R⁵′ is —O—, —S—, —CO— or —NR⁹—;

R⁹ is a hydrogen atom or an alkyl group having 1-6 carbon atoms; and

R²′ and R³′ are directly attached to the polymerizable monomer unit, in the molecular main chain;

(21) A process of producing the copolymer according to any one of the above (18)-(20), comprising a step of polymerizing one or more ring-opening polymerizable monomer by using a compound of the formula (Id′) as an polymerization initiator:

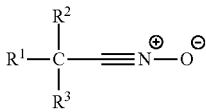

wherein:

R¹ is a hydrogen atom or a hydrocarbon group;

R² is —R⁴—R⁵;

R³ is —R⁴—R⁵ or —R⁴—R⁶;

R⁴ is a divalent organic group;

R⁵ is OH, SH, —COOH or —NHR⁹;

R⁹ is a hydrogen atom or an alkyl group having 1-6 carbon atoms; and

R⁶ is a hydrogen atom or an alkyl group having 1-6 carbon atoms;

(22) A composition applied to a material containing a group reactive with a nitrileoxide group, comprising one or more polymers according to any one of the above (18)-(20);

(23) The composition according to the above (22), which is a grafting agent;

(24) The composition according to the above (22), which is a crosslinking agent.

Effect of the Invention

According to the present invention, the polymer compound having a plurality of nitrileoxide groups is provided. Since such polymer compound has a plurality of nitrileoxide groups, the polymer functions as a crosslinking agent itself, and can self-crosslink and cure without using a conventional crosslinking agent having low molecular weight. In addition, the polymer compound of the present invention can be used as a crosslinking agent in place of conventional crosslinking agent having low molecular weight. Since the polymer compound of the present invention has high molecular weight, the polymer compound hard to become outgases or effluent component, and even when the polymer compound is used as a member of a semiconductor manufacturing process apparatus, the polymer compound hard to cause process errors. According to the present invention, a nitrileoxide group is able to be introduced into any position such as one terminal, both terminals, or a central portion of the polymer compound.

Embodiments to Carry Out the Invention

In the present specification, unless otherwise specified, "a hydrocarbon group" means a group containing a carbon atom and a hydrogen atom (provided that, a part of or all of hydrogen atoms may be replaced with the following substituents). Examples of the hydrocarbon group include, but are not particularly limited to, for example, an aliphatic hydrocarbon group, an aromatic hydrocarbon group, and the like, which may be substituted by one or more substituents, a hydrocarbon group having 1-20 carbon atoms. It is noted that the hydrocarbon group may have one or more N, O, S, or the like at its end or in its molecular chain.

In the present specification, unless otherwise specified, the "aliphatic hydrocarbon group" may be straight, branched or cyclic and saturated or unsaturated, and may contain one or more rings. Examples of the "aliphatic hydrocarbon group" include, but are not particularly limited to, an alkyl group, an alkenyl group, an alkynyl group, a cycloalkyl group, a cycloalkenyl group. The "aliphatic hydrocarbon group" may be substituted by one or more substituents.

In the present specification, unless otherwise specified, the "alkyl group" may be straight or branched, and is for example an alkyl group having 1-20, preferably 1-12, more preferably 1-6 carbon atoms. Examples of the "alkyl group" include, but are not particularly limited to, a methyl group, an ethyl group, a propyl group, an isopropyl group, an n-butyl group, an isobutyl group, a sec-butyl group, a tert-butyl group, a n-pentyl group, a 1-methylbutyl group, a 2-methylbutyl group, a 3-methylbutyl group, a 1-ethylpropyl group, a 1,1-dimethylpropyl group, a 1,2-dimethylpropyl group, a 2,2-dimethylpropyl group, an n-hexyl group, a 1-methylpentyl group, a 2-methylpentyl group, a 3-methylpentyl group, a 4-methylpentyl group, an n-hexyl group, a 2-methylpentyl group, a 3-methylpentyl group, a 4-methylpentyl group, a 1-ethylbutyl group, a 2-ethylbutyl group, a 1,1-dimethylbutyl group, a 1,2-dimethylbutyl group, a 1,3-dimethylbutyl group, a 2,2-dimethylbutyl group, a 2,3-dimethylbutyl group, a 3,3-dimethylbutyl group, a 1,1,2-trimethylpropyl group, a 1,2,2-trimethylpropyl group, a 1-ethyl-1-methylpropyl group, a 1-ethyl-2-methylpropyl group, and the like. The "alkyl group" may be substituted by one or more substituents.

In the present specification, unless otherwise specified, the "alkenyl group" may be straight or branched, and is for example an alkenyl group having 2-20, preferably 2-12, more preferably 2-6 carbon atoms. Examples of the "alkenyl group" include, but are not particularly limited to, for example, a group which at least one carbon-carbon single bond in the above alkyl group is replaced with a carbon-carbon double bond, specifically, a vinyl group, an allyl group, a 1-propenyl group, an isopropenyl group, a 2-methyl-1-propenyl group, a 2-methyl-2-propenyl group, a 1-butenyl group, a 2-butenyl group, a 3-butenyl group, a 1-pentenyl group, a 1-hexenyl group, a 1,3-hexadienyl group, a 1,5-hexadienyl group, and the like. The "alkenyl group" may be substituted by one or more substituents.

In the present specification, unless otherwise specified, the "alkynyl group" may be straight or branched, and is for example an alkynyl group having 2-20, preferably 2-12, more preferably 2-6 carbon atoms. Examples of the "alkynyl group" include, but are not particularly limited to, for example, a group which at least one carbon-carbon single bond in the above alkyl group is replaced with a carbon-carbon triple bond, specifically, an ethynyl group, a 1-propynyl group, a 2-propynyl group, a 1-butynyl group, a 2-butynyl group, a 3-butynyl group, a 1-methyl-2-propynyl group, a 1-pentynyl group, a 1-ethyl-2-propynyl group, a 1-hexynyl group, a 2-hexynyl group, and the like. The "alkynyl group" may be substituted by one or more substituents.

In the present specification, unless otherwise specified, the "cycloalkyl group" is a cyclic alkyl group having 3-20, preferably 5-12 carbon atoms. Examples of the "cycloalkyl group" include, but are not particularly limited to, for example, a cyclopropyl group, a cyclobutyl group, a cyclopentyl group, a cyclohexyl group, a cycloheptyl group, a cyclooctyl group, and the like. The "cycloalkyl group" may be substituted by one or more substituents.

In the present specification, unless otherwise specified, the "cycloalkenyl group" is a cyclic alkenyl group having 3-20, preferably 5-12 carbon atoms. Examples of the "cycloalkenyl group" include, but are not particularly limited to, for example, a cyclopropenyl group, a cyclobutenyl group, a cyclopentenyl group, a cyclohexenyl group, a cycloheptenyl group, a cyclooctenyl group, and the like. The "cycloalkenyl group" may be substituted by one or more substituents.

In the present specification, unless otherwise specified, the "aromatic hydrocarbon group (hereinafter, referred to as an aryl group)" may be monocyclic or polycyclic, for example bicyclic or tricyclic, or may be an aromatic heterocyclic group (hereinafter, referred to as a heteroaryl group). Examples of the "aromatic hydrocarbon group" include, but are not particularly limited to, an aryl group having 3-20 carbon atoms such as a phenyl group, a naphthyl group, and a heteroaryl group having 3-20 carbon atoms such as a furyl group, a thienyl group, a pyridyl group, an indolyl group, a quinolyl group, an isoquinolyl group, or an imidazolyl group. The "aromatic hydrocarbon group" may be substituted by one or more substituents.

In the present specification, unless otherwise specified, the "alkylene group" is a divalent group obtained by removing a hydrogen atom on a carbon atom in the alkyl group described above.

In the present specification, unless otherwise specified, the "(poly)alkylether group" is a group obtained by inserting an etheric oxygen atom into one or more carbon-carbon bonds in the alkyl group described above A preferable (poly)alkylether group is a group of the following formula:

R—(O(CH$_2$)$_n$)$_m$— wherein R is a C$_{1-16}$ alkyl group, m is an integer of 1-300, and n is at each occurrence an integer of 1-6.

Another preferable (poly)alkylether group is a group of the following formula:

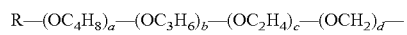

R—(OC$_4$H$_8$)$_a$—(OC$_3$H$_6$)$_b$—(OC$_2$H$_4$)$_c$—(OCH$_2$)$_d$— wherein:
R is a C$_{1-16}$ alkyl group;
a, b, c and d are each independently an integer of 0 or more and 200 or less, the sum of a, b, c and d is at least one, and the occurrence order of the respective repeating units in parentheses with the subscript a, b, c or d is not limited in the formula.

When the (poly)alkylether group described above is used as a divalent group, it is a group of the following formula:

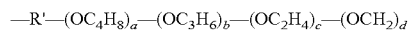

—R'—(OC$_4$H$_8$)$_a$—(OC$_3$H$_6$)$_b$—(OC$_2$H$_4$)$_c$—(OCH$_2$)$_d$— wherein R' is a $C_{0-16}$ alkylene group. It is noted that in the present specification, C0 means that a carbon atom is absent, for example a $C_{0-16}$ alkylene group is a single bond or a $C_{1-16}$ alkylene group.

In the present specification, unless otherwise specified, the hydrocarbon group, the alkyl group, the alkenyl group, the alkynyl group, the cycloalkyl group, the cycloalkenyl group, the aromatic hydrocarbon group and an alkylene group may be substituted. Examples of the substituents include, but are not particularly limited to, for example, an oxygen atom; a halogen atom (fluorine, chlorine, bromine, iodine); a hydroxyl group; an unsubstituted, mono-substituted or di-substituted amino group; a nitro group; an azide group; a $C_{1-16}$ alkyl group, a $C_{2-16}$ alkenyl group, a $C_{2-16}$ alkynyl group, a $C_{3-16}$ cycloalkyl group, a $C_{2-16}$ cycloalkenyl group, a $C_{6-16}$ heterocycloalkyl group, a $C_{6-16}$ heterocycloalkenyl group, a $C_{6-16}$ aryl group, a $C_{6-16}$ heteroaryl group, a $C_{1-16}$ alkoxy group, a $C_{6-16}$ aryloxy, a $C_{1-16}$ alkylthio or a $C_{1-20}$ (poly)alkyl ether group which may be substituted by one or more halogen atoms; —O—C(O)—OR$^a$, —O—C(O)—NR$^a_2$, —C(O)—R$^a$, —C(O)—OR$^a$, —NR$^a$—C(O)—R$^a$, —NR$^a$—C(NR$^a$)—R$^a$, —C(NR$^a$)—R$^a$ or —C(NR$^a$)—NR$^a_2$ (wherein R$^a$ represents each independently a hydrogen atom, a $C_{1-16}$ alkyl group, a $C_{2-16}$ alkenyl group, a $C_{2-16}$ alkynyl group, a $C_{3-16}$ cycloalkyl group, a $C_{3-16}$ cycloalkenyl group, a $C_{6-16}$ heterocycloalkyl group, a $C_{6-16}$ heterocycloalkenyl group, a $C_{6-16}$ aryl group or a $C_{6-16}$ heteroaryl group).

The "mono-substituted amino group" represents an amino group substituted by one substituent independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ a cycloalkenyl group, a $C_{6-16}$ heterocycloalkyl group, a $C_{6-16}$ heterocycloalkenyl group, a $C_{6-16}$ aryl group and a $C_{6-16}$ heteroaryl group, but is not particularly limited thereto. Examples of the "mono-substituted amino group" include, but are not limited to, methylamino, ethylamino, phenylamino, and the like.

The "di-substituted amino group" represents an amino group substituted by two substituents independently selected from the group consisting of a $C_{1-16}$ alkyl group, a $C_{2-16}$ alkenyl group, a $C_{2-16}$ alkynyl group, a $C_{3-16}$ cycloalkyl group, a $C_{3-16}$ a cycloalkenyl group, a $C_{6-16}$ heterocycloalkyl group, a $C_{6-16}$ heterocycloalkenyl group, a $C_{6-16}$ aryl group and a $C_{6-16}$ heteroaryl group, but are not particularly limited thereto. Examples of the "di-substituted amino group" include, but are not limited to, dimethylamino, diethylamino, diphenylamino, and the like.

Examples of the "$C_{1-16}$ alkoxy group" include, but are not particularly limited to, for example, a methoxy group, an ethoxy group, an n-propoxy group, an isopropoxy group, an n-butoxy group, an isobutoxy group, a sec-butoxy group, a tert-butoxy group, an n-pentyloxy group, an isopentyloxy group, a neopentyloxy group, a tert-pentyloxy group, a 1-ethylpropoxy group, an n-hexyloxy group, an isohexyloxy group, a neohexyloxy group, a 2-ethylbutoxy group, and the like.

Examples of the "$C_{6-16}$ aryloxy" include, but are not particularly limited to, for example, phenoxy, naphthyloxy, and the like.

Examples of the "$C_{1-16}$ alkylthio" include, but are not particularly limited to, for example, methylthio, ethylthio, propylthio, isopropylthio, butylthio, sec-butylthio, tert-butylthio, and the like.

In the present specification, unless otherwise specified, the "halogen (or halogen atom)" means a fluorine atom, a chlorine atom, a bromine atom, an iodine atom, and the like.

In the present specification, unless otherwise specified, the "perfluoroalkyl group" means a group which all hydrogen atoms in the above alkyl group are replaced with a fluorine atom, and is represented by —C$_m$F$_{2m+1}$ wherein m is an integer, specifically an integer of 1-16, for example an integer of 1- or 1-6. The "perfluoroalkyl group" may be straight or branched, preferably straight.

Hereinafter, the compound of the present invention will be described below.

The present invention provides a compound of the formula (I):

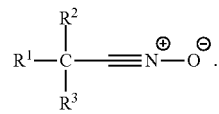

In the formula (I), $R^1$ is a hydrogen atom or a hydrocarbon group, preferably a hydrocarbon group.

The hydrocarbon group in $R^1$ is an alkyl group having 1-16 carbon atoms, a cycloalkyl group having 3-20 carbon atoms, an aryl group having 3-20 carbon atoms, or a (poly)alkylether group. These groups may have one or more substituents.

Examples of the substituents include, but are not limited to, preferably a halogen atom (for example, fluorine, chlorine, bromine, iodine), an alkyl group having 1-10 carbon atoms, a cycloalkyl group having 3-14 carbon atoms, an aryl group having 3-14 carbon atoms, or a (poly)alkylether group having 1-10 carbon atoms.

In one embodiment, $R^1$ is $R^{1'}$—Z—. In the formula, $R^{1'}$ is a hydrocarbon group. In one embodiment, $R^{1'}$ is an alkyl group having 1-16 carbon atoms or (poly)alkylether, which may be substituted by fluorine. When they are substituted by fluorine, these alkyl groups or (poly)alkylether groups may be preferably a perfluoroalkyl group, a perfluoro(poly)alkylether group, perfluoroalkyl-(CH$_2$)$_n$—, or perfluoro(poly)alkylether-(CH$_2$)$_n$—. In another embodiment, $R^{1'}$ may be H(CH$_2$)$_n$, F(CF$_2$)$_m$, CF(F(CF$_2$)$_m$)$_2$—, H(CF$_2$)$_m$—, F(CF$_2$)$_m$—(OCF(CF$_3$)CF$_2$)$_p$—OCF(CF$_3$)—, or (F(CF$_2$)$_m$)$_2$—C(CH$_3$)—CF$_2$—, wherein n is an integer of 1-6, m is an integer of 1-8, and p is an integer of 0-4. In the formula, Z is a single bond or —(CH$_2$)$_l$O— wherein l is an integer of 0-6.

In the formula (I), $R^2$ is —$R^4$—$R^5$.

In the formula (I), $R^3$ is —$R^4$—$R^5$ or —$R^4$—$R^6$.

$R^4$ is a divalent organic group. $R^4$ is preferably, —$R^{11}$—$R^{12}$—.

$R^{11}$ is cycloalkylene having 3-10 carbon atoms, an arylene having 3-10 carbon atoms or —CR$^7$R$^8$—.

$R^7$ and $R^8$ are each independently a hydrogen atom or an alkyl group having 1-6 carbon atoms. The alkyl group having 1-6 carbon atoms is preferably an alkyl group having 1-3 carbon atoms, for example, a methyl group, an ethyl group or a propyl group.

With respect to the hydrocarbon of —CR$^7$R$^8$— preferably has larger substitution level. That is, preferably, at least one of $R^7$ and $R^8$ is an alkyl group having 1-6 carbon atoms. When one of $R^7$ and $R^8$ is an alkyl group having 1-6 carbon atoms, the carbon atom of —CR$^7$R$^8$— is a tertiary carbon (however, a secondary carbon when $R^{12}$ is a single bond and $R^6$ is a hydrogen atom), the stability of the nitrileoxide group is increased. When both of $R^7$ and $R^8$ are an alkyl group having 1-6 carbon atoms, a carbon atom of —CR$^7$R$^8$— is quaternary carbon (however, a tertiary carbon when $R^{12}$ is a single bond, and $R^6$ is a hydrogen atom), the stability of the nitrileoxide group is more increased.

$R^{11}$ is preferably an arylene having 3-10 carbon atoms or —$CR^7R^8$— wherein $R^7$ and $R^8$ are an alkyl group having 1-6 carbon atoms, more preferably an arylene having 3-10 carbon atoms, for example, phenylene.

$R^{12}$ is a single bond or a linker having 1-10 atoms of the main chain.

The linker having 1-10 atoms of the main chain is, but not particularly limited to, for example, an alkylene group, a cycloalkylene group, a heterocycloalkylene group, anarylene group, a heteroarylene group or a divalent (poly) alkylether group, or a combination thereof, and preferably an alkylene group or a divalent (poly)alkylether group. These groups may have one or more substituents. Examples of the substituents include, but are not limited to, preferably a halogen atom (for example, fluorine, chlorine, bromine, iodine), an alkyl group having 1-10 carbon atoms, a cycloalkyl group having 3-14 carbon atoms, an aryl group having 3-14 carbon atoms, or a (poly)alkylether group having 1-10 carbon atoms.

Preferable $R^4$ is a phenylene group, phenylene—an alkylene group, phenylene-oxyalkylene group, or phenylene-polyalkylether group. In the —$R^4$—$R^5$ group, $R^4$ is more preferably, phenylene-alkylene, phenylene-oxyalkylene group or phenylene-polyalkylether group.

In one embodiment, the —$R^4$-$R^5$ group may be a phenyl group.

$R^5$ is OH, SH, COOH or $NHR^9$, preferably OH, SH, COOH or $NH_2$, more preferably OH.

$R^9$ is a hydrogen atom or an alkyl group having 1-6 carbon atoms. The alkyl group having 1-6 carbon atoms is preferably an alkyl group having 1-3 carbon atoms, particularly a methyl group, an ethyl group or a propyl group, more preferably a methyl group. $R^9$ is preferably a hydrogen atom.

Since —$R^4$—$R^5$ has $R^5$ which is a reactive group at the terminal, a compound of the formula (I) can cause various reactions by this group.

$R^6$ is a hydrogen atom or an alkyl group having 1-6 carbon atoms. The alkyl group having 1-6 carbon atoms is preferably an alkyl group having 1-3 carbon atoms, particularly a methyl group, an ethyl group or a propyl group, more preferably a methyl group. $R^6$ is preferably a hydrogen atom.

A preferable compound of the formula (I) is a compound wherein $R^1$ is an alkyl group having 1-10 carbon atoms, $R^2$ and $R^3$ are —$R^4$—$R^5$, $R^4$ is phenylene, phenylene-alkylene, phenylene-oxyalkylene or phenylene-polyalkylether group, and $R^5$ is OH.

A more preferable compound of the formula (I) is a compound wherein $R^1$ is an alkyl group having 1-10 carbon atoms, $R^2$ and $R^3$ are —$R^4$—$R^5$, $R^4$ is a phenylene-oxyalkylene or phenylene-polyalkylether group, and $R^5$ is OH.

Another preferable compound of the formula (I) is a compound wherein $R^1$ is an alkyl group having 1-10 carbon atoms, $R^2$ is —$R^4$—$R^5$, $R^3$ is —$R^4$—$R^6$, $R^4$ is phenylene, phenylene-alkylene, phenylene-oxyalkylene or phenylene-polyalkylether group, and $R^5$ is OH.

A more preferable compound of the formula (I) is a compound wherein $R^1$ is an alkyl group having 1-10 carbon atoms, $R^2$ is —$R^4$—$R^5$ (wherein $R^4$ is a phenylene-oxyalkylene or phenylene-polyalkylether group), $R^3$ is —$R^4$—$R^6$ (wherein $R^4$ is phenylene, phenylene-alkylene, phenylene-oxyalkylene or phenylene-polyalkylether group), and $R^5$ is OH.

Since the nitrileoxide compound of the formula (I) has two condensation polymerizable or addition polymerizable groups (OH, SH, COOH or $NHR^9$) in the molecule, the nitrileoxide compound can be used as a raw monomer for condensation polymerization or addition polymerization reaction. Therefore, the present invention provides a monomer of the formula (Ia'):

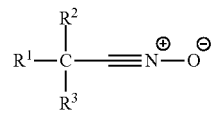

wherein:
$R^1$ is a hydrogen atom or a hydrocarbon group;
$R^2$ and $R^3$ are each independently —$R^4$—$R^5$;
$R^4$ is a divalent organic group;
$R^5$ is OH, SH, COOH or $NHR^9$;
$R^9$ is a hydrogen atom or an alkyl group having 1-6 carbon atoms; and
$R^6$ is a hydrogen atom or an alkyl group having 1-6 carbon atoms.

Since the nitrileoxide compound of the formula (I) has a nucleophilic group (OH, SH, COOH or $NHR^9$), the nitrileoxide compound can be used as an initiator in a ring-opening polymerization reaction. Therefore, the present invention provides an initiator of the formula (Id'):

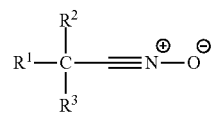

wherein:
$R^1$ is a hydrogen atom or a hydrocarbon group;
$R^2$ is —$R^4$—$R^5$;
$R^3$ is —$R^4$—$R^5$ or —$R^4$—$R^6$;
$R^4$ is a divalent organic group;
$R^5$ is OH, SH, COOH or $NHR^9$;
$R^9$ is a hydrogen atom or an alkyl group having 1-6 carbon atoms; and
$R^6$ is a hydrogen atom or an alkyl group having 1-6 carbon atoms.

The present invention provides a compound of the formula (III):

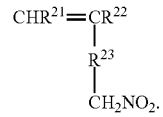

In the formula (III), $R^{21}$ and $R^{22}$ are a hydrogen atom or an alkyl group. The alkyl group is, but not particularly limited to, preferably an alkyl group having 1-6 carbon atoms, more preferably an alkyl group having 1-3 carbon atoms, further preferably a methyl group. $R^{21}$ and $R^{22}$ are preferably a hydrogen atom or a methyl group, more preferably a hydrogen atom.

In the formula (III), $R^{23}$ is a divalent organic group.

In one embodiment, $R^{23}$ is —$R^{24}$—$R^{25}$—$R^{26}$—. It is noted that $R^{24}$ in this group is attached to a carbon tom having an ethylenic double bond, and $R^{26}$ is attached to a nitrileoxide group.

$R^{24}$ is a single bond, an alkylene having 1-6 carbon atoms, —CO— or —CO—O—, —NR—CO— (R is a hydrogen atom or an alkyl group), —O—CO—, $R^{25}$ is a linker having 1-20 atoms of the main chain, $R^{26}$ is a single bond, an alkylene having 1-6 carbon atoms or —$CR^{27}R^{28}$—, $R^{27}$ and $R^{28}$ are each independently a hydrogen atom, an alkyl group having 1-6 carbon atoms or an aryl group having 5-10 carbon atoms.

In the compound of the formula (III), when $R^{27}$ is —$CR^{27}R^{28}$—, the nitrileoxide group is attached to this carbon atom. In order to increase the stability of nitrileoxide, this carbon atom is preferably a tertiary carbon, more preferably quaternary carbon.

In a preferable embodiment, $R^{24}$ is —CO—, —CO—NR— (R is an alkyl group or a hydrogen atom) or —CO—O—, —NR—CO— (R is a hydrogen atom or an alkyl group), —O—CO—;

$R^{25}$ is a linker having 1-20 atoms of the main chain;

$R^{26}$ is —$CR^{27}R^{28}$—;

$R^{27}$ is an aryl group having 5-10 carbon atoms; and $R^{28}$ is a hydrogen atom or an alkyl group having 1-6 carbon atoms, more preferably an alkyl group having 1-6 carbon atoms.

The linker having 1-20 atoms of the main chain of $R^{25}$ is, but not particularly limited to, for example, a group or a combination of two or more groups selected from the group consisting of an alkylene group, a cycloalkylene group, an arylene group, a carbonyl group, an ester group (—COO— or —OCO—), an amide group (—$CONH_2$— or —$NH_2CO$—), —O— and —S—. These group may be substituted by one or more substituents, for example substituent selected from the group consisting of a halogen atom (for example, fluorine, chlorine, bromine or iodine, preferably fluorine), an alkyl group having 1-6 carbon atoms, a cycloalkyl group having 3-10 carbon atoms and an aryl group having 3-10 carbon atoms.

$R^{25}$ is preferably,

—($CH_2CH_2$—O)$_{p1}$— (p1 is an integer of 1-6),

—($CHR^{31}$)$_{p2}$—O— (p2 is an integer of 1-9, and $R^{31}$ is a hydrogen atom or a methyl group), —($CH_2CH_2$—O)$_{p3}$—CONH—$CH_2CH_2$—O— (p3 is an integer of 1-5), —($CH_2CH_2$)$_{p4}$—O—($CH_2CH_2$)$_{p5}$— (p4 is an integer of 1-16, and p5 is an integer of 1-16), —($CH_2$)$_{p6}$—O—CONH—($CH_2$)$_{p7}$— (p6 is an integer of 1-8, and p7 is an integer of 1-8), —($CH_2$)$_{p8}$— (p8 is an integer of 1-10), -phenyl-, or —O— (in this case, $R^1$ is not —O— and —CO—O—).

$R^{25}$ is more preferably

—($CH_2CH_2$—O)$_{p1}$— (p1 is an integer of 1-6),

—($CHR^{31}$)$_{p2}$—O— (p2 is an integer of 1-9, and $R^{31}$ is a hydrogen atom or a methyl group), —($CH_2$)$_{p8}$— (p8 is an integer of 1-10), or -phenyl-.

The compound of the formula (III) has the —$CH_2NO_2$ group at the terminal. By subjecting this group to dehydration, this group can be converted to the —$CN^+O^-$ group. By polymerizing the compound of the formula (III), and then dehydrating the —$CH_2NO_2$ group of the resulting polymer, a polymer having a plurality of nitrileoxide groups can be obtained.

The dehydration can be performed, but not particularly limited, by using a concentrated sulfuric acid, trifluoromethanesulfonic acid, trifluoromethane sulfonimide, or phenyl isocyanate, or other strong acid having a non-nucleophilic counter anion.

In a preferable embodiment, the dehydration is performed by using an isocyanate compound in the presence of a base, particularly preferably by using phenyl isocyanate in the presence of triethylamine.

The present invention provides a copolymer comprising one or more monomer units of the formula (Ia):

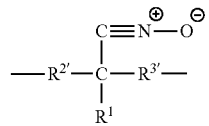

wherein:

$R^1$ is a hydrogen atom or a hydrocarbon group;

$R^{2'}$ and $R^{3'}$ are each independently, —$R^4$—$R^{5'}$— wherein $R^4$ is attached to a carbon atom having a nitrileoxide group;

$R^4$ is a divalent organic group;

$R^{5'}$ is each independently —O—, —S—, —CO— or —$NR^9$—; and $R^9$ is a hydrogen atom or an alkyl group having 1-6 carbon atoms, and one or more condensation polymerizable or addition polymerizable monomer units.

When the polymer consists of for example only one type of the monomer unit of the formula (Ia) and only one type of the condensation polymerizable or addition polymerizable monomer unit, the polymer may comprise a polymer of the following formula:

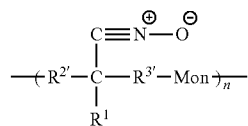

wherein $R^1$, $R^{2'}$ and $R^{3'}$ are as defined in the formula (Ia),

Mon is a condensation polymerizable or addition polymerizable monomer unit; and n is any integer.

The copolymer can be obtained by condensation polymerizing or addition polymerizing one or more compounds of the formula (I) (both of $R^2$ and $R^3$ are —$R^4$—$R^5$) and one or more condensation polymerizable or addition polymerizable monomers. Therefore, the present invention provides a process for producing the copolymer comprising a monomer unit of the formula (Ia) and one or more condensation polymerizable or addition polymerizable monomer units, comprising a step of polymerizing a monomer of the formula (Ia'):

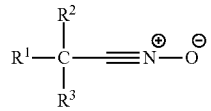

wherein:

$R^1$ is a hydrogen atom or a hydrocarbon group;

$R^2$ and $R^3$ are each independently —$R^4$—$R^5$;

$R^4$ is a divalent organic group;

$R^5$ is OH, SH, COOH or $NHR^9$;

$R^9$ is a hydrogen atom or an alkyl group having 1-6 carbon atoms, and one or more condensation polymerizable or addition polymerizable monomers.

The monomer unit of the formula (Ia) corresponds to a monomer of the formula (I).

In the formula (Ia), $R^1$ is as defined for $R^1$ in the formula (I), and is a hydrogen atom or a hydrocarbon group.

In the formula (Ia), $R^{2'}$ and $R^{3'}$ are as defined for $R^2$ and $R^3$ in the formula (I), respectively, is a residue of $R^2$ and $R^3$ after condensation polymerization or addition polymerization.

$R^{2'}$ and $R^{3'}$ are each independently —$R^4$—$R^{5'}$—.$R^5$, corresponds to $R^5$ in the formula (I), and is a divalent group in which a leaving group is removed from $R^5$. $R^{5'}$ is specifically each independently —O—, —S—, —CO— or —$NR^9$—.

$R^9$ is as defined for $R^9$ in the formula (I), is a hydrogen atom or an alkyl group having 1-6 carbon atoms.

In the copolymer, a structure of one or more condensation polymerizable or addition polymerizable monomer units is not limited, and may be a residue of various condensation polymerizable or addition polymerizable monomers.

The one or more condensation polymerizable monomers used in producing of the above copolymer is not limited as long as it is a compound having two or more group polymerizable with $R^5$ (for example, —COCl, —COBr, —COF, —OH, —F, —Cl, —Br, —I, —COOH, —$NH_2$, carboxylic acid anhydride, etc., depending on the type of $R^5$).

Examples of the condensation polymerizable monomer include, but are not particularly limited, as follows:

Hal-CO—$R^{41}$—CO-Hal wherein: Hal is a halogen atom, preferably chlorine, bromine, fluorine, particularly preferably chlorine, $R^{41}$ is an alkyl group or an aryl group;

Fluoroarenes (for example, hexafluorobenzene, bis(4-fluorophenyl)ketone),

Chloroarenes (for example, dichlorobenzene, bis(4-chlorophenyl) ketone),

Aliphatic chloride (for example, dichloromethane, 1,2-dichloroethane, bifunctional benzyl chloride), Aliphatic bromide (for example, dibromomethane, bifunctional benzyl bromide, α,ω-dibromide oligomethylene), Aliphatic iodide (for example, diiodomethane), Aromatic tetra acid anhydride, Aromatic diamine, Aromatic hydroxy amine The one or more addition polymerizable monomers used in producing of the above copolymer is not limited as long as the compound comprises two or more groups to which $R^5$ can added (for example, an epoxy group, —C=O, —C=C—, —C≡N, —N=C=O, —N=C=S, carbodiimide, ketene, keteneimine, or the like).

Examples of the addition polymerizable monomer include, but are not particularly limited, as follows:

EPO—$CH_2$—$R^{42}$—$CH_2$-EPO;
H—C(O)—$R^{42}$—C(O)H;
N≡C—$R^{42}$—C≡N;
O=C=N—$R^{42}$—N=C=O;
S=C=N—$R^{42}$—N=C=S wherein: EPO is an epoxy group, and $R^{42}$ is an alkylene group, an arylene group or a divalent group which these groups are linked, which may be substituted by a fluorine atom, for example a perfluoroalkylene group.

In one embodiment, in producing of the copolymer, further condensation polymerizable or addition polymerizable monomer may be used. The further condensation polymerizable or addition polymerizable monomer may be that capable of condensation or addition reaction with a compound having one or more groups which are not directly reacted with the compound of the formula (I) and are able to condensation polymerize or addition polymerize with $R^5$. For example, example of the monomer may be a compound having two same groups as $R^5$ in the compound of the formula (I) and does not fall in the scope of the formula (I).

Examples of the further condensation polymerizable monomer include a group of the formula:

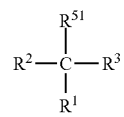

wherein $R^1$, $R^2$ and $R^3$ are as defined for $R^1$, $R^2$ and $R^3$ in the formula (I), and $R^{51}$ is an alkyl group or an aryl group.

In one embodiment, the polymer may be a polymer obtained by carbon monoxide insertion reaction. In this case, —CO— group exists between the monomer unit of the formula (Ia) and the condensation polymerizable or addition polymerizable monomer unit.

The polymer described above may include, for example, when the polymer consists of only one monomer unit of the formula (Ia) and only one condensation polymerizable monomer unit or addition polymerizable monomer, a polymer of the following formula:

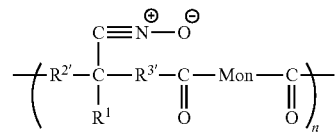

wherein $R^1$, $R^{2'}$ and $R^{3'}$ are as defined in the formula (Ia),

Mon is a condensation polymerizable monomer unit or addition polymerizable monomer unit; and n is any integer.

In the above embodiment, the polymerizable monomer unit may be a monomer unit of the formula (Ia'):

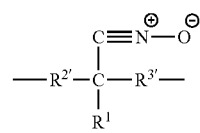

wherein:

$R^1$ is a hydrogen atom or a hydrocarbon group;

$R^{2'}$ and $R^{3'}$ are each independently —$R^4$— or —$R^4$—$R^{5'}$— wherein $R^4$ is attached to a carbon atom having a nitrileoxide group;

$R^4$ is a divalent organic group;

$R^{5'}$ is each independently —O—, —S—, —CO— or —$NR^9$—; and $R^9$ is a hydrogen atom or an alkyl group having 1-6 carbon atoms. The monomer unit of the formula (Ia') and the monomer unit of the formula (Ia) are derived from the monomer of the same formula (I).

The above polymer may include a polymer of the following formula:

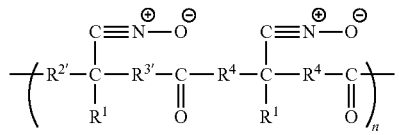

wherein $R^1$, $R^{2'}$, $R^{3'}$ and $R^4$ are as defined in the formula (Ia), and n is any integer.

The above polymer can be obtained by reacting the monomer of the formula (I), and optionally a condensation polymerizable monomer, and carbon monoxide in the presence of a transition metal such as Pd. The reaction can be represented by the following scheme, and known as a carbon monoxide insertion reaction.

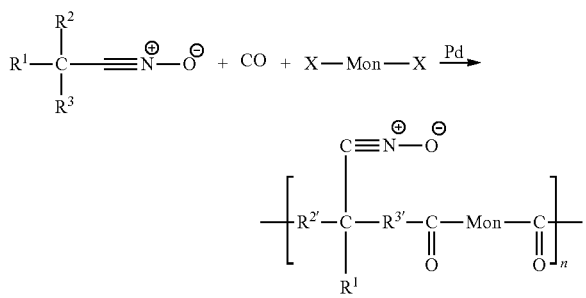

wherein X is a leaving group, and the other symbols are as defined above.

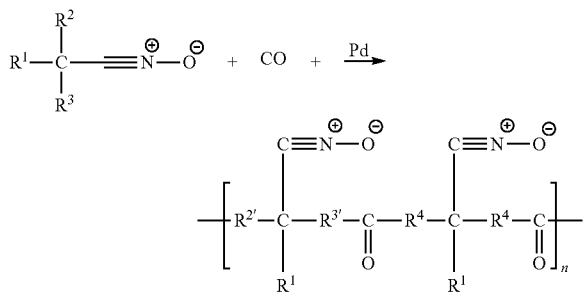

wherein each symbol is as defined above.

Specifically, it includes the following reaction.

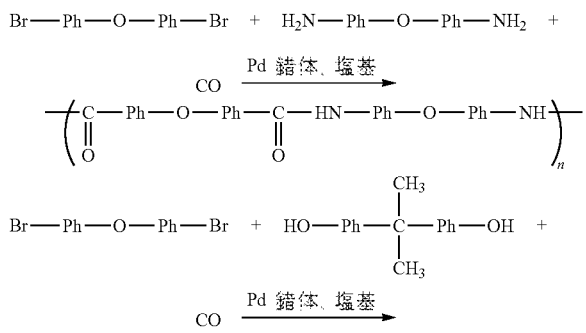

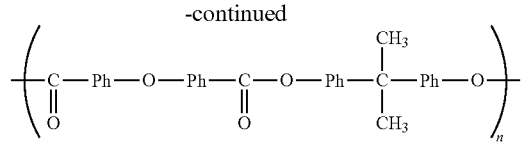

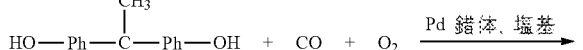

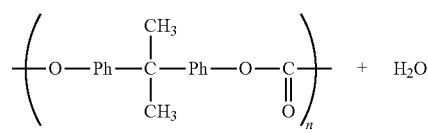

The present invention provides a homopolymer or copolymer comprising one or more monomer units of the formula (IIIa):

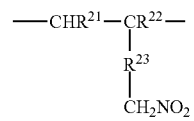

wherein:

$R^{21}$ is a hydrogen atom or an alkyl group;

$R^{22}$ is a hydrogen atom or an alkyl group; and $R^{23}$ is a divalent organic group.

The above polymer can be obtained by polymerizing one or more compounds of the formula (III). Therefore, the present invention provides a process for producing a polymer comprising one or more monomer units of the formula (IIIa), comprising a step of polymerizing a monomer of the formula (III):

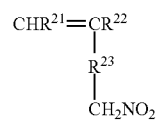

wherein:

$R^{21}$ is a hydrogen atom or an alkyl group;

$R^{22}$ is a hydrogen atom or an alkyl group; and $R^{23}$ is a divalent organic group.

One or more compounds of the formula (III) describe above can be polymerized with one or more polymerizable monomers. In this case, a copolymer comprising one or more monomer units of the formula (IIIa) and one or more polymerizable monomer units.

The monomer unit of the formula (IIIa) corresponds to the monomer of the formula (III).

In the formula (IIIa), $R^{21}$ is as defined for $R^{21}$ in the formula (III), and is a hydrogen atom or an alkyl group.

In the formula (IIIa), $R^{22}$ is as defined for $R^{22}$ in the formula (III), and is a hydrogen atom or an alkyl group.

In the formula (IIIa), $R^{23}$ is as defined for $R^{23}$ in the formula (III), and is a divalent organic group.

The present invention provides a homopolymer or a copolymer comprising one or more monomer units of the formula (IIa):

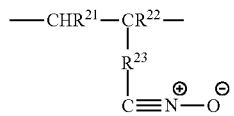

wherein:
R$^{21}$ is a hydrogen atom or an alkyl group;
R$^{22}$ is a hydrogen atom or an alkyl group; and
R$^{23}$ is a divalent organic group.

The present invention provides a copolymer comprising one or more monomer units of the formula (IIa) and one or more polymerizable monomer unit.

The polymer comprising the monomer unit of the formula (IIa) can be produced by dehydrating a CH$_2$NO$_2$ group in the corresponding polymer comprising the monomer unit of the formula (IIIa) to convert a CN$^+$O$^-$ group.

The structure of one or more polymerizable monomer unit in the above copolymer may be a residue of various monomers.

One or more polymerizable monomers used in producing of the above polymer are not particularly limited, and for example, a radical polymerizable monomer, an anion polymerizable monomer, a cation polymerizable monomer, a coordination polymerizable monomer can be used. Preferable polymerizable monomer is a radical polymerizable monomer.

The present invention provides a polymer comprising a monomer unit of the formula (Xa) or the formula (Xb):

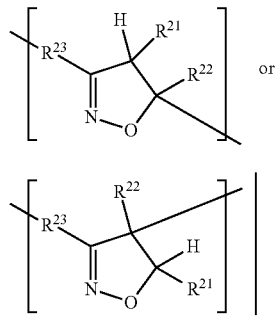

wherein:
R$^{21}$ is a hydrogen atom or an alkyl group;
R$^{22}$ is a hydrogen atom or an alkyl group; and
R$^{23}$ is a divalent organic group.

The polymer of the formula (Xa) or the formula (Xb) can be obtained by dehydrating a compound of the formula (III):

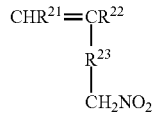

wherein:
R$^{21}$ is a hydrogen atom or an alkyl group;
R$^{22}$ is a hydrogen atom or an alkyl group; and R$^{23}$ is a divalent organic group,
to obtain a monomer of the formula (II):

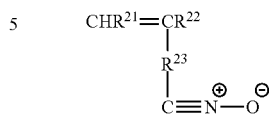

wherein:
R$^{21}$ is a hydrogen atom or an alkyl group;
R$^{22}$ is a hydrogen atom or an alkyl group; and
R$^{23}$ is a divalent organic group,
and polymerizing the monomer.

The present invention provides a polymer comprising one or more ring-opening polymerizable monomer units, having a group of the formula (Ib):

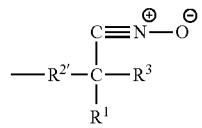

wherein:
R$^1$ is a hydrogen atom or a hydrocarbon group;
R$^{2'}$ is —R$^4$—R$^{5'}$— wherein R$^4$ is a carbon atom having a nitrileoxide group;
R$^3$ is —R$^4$—R$^6$;
R$^4$ is a divalent organic group;
R$^{5'}$ is —O—, —S—, —CO—O— or —NR$^9$—;
R$^9$ is a hydrogen atom or an alkyl group having 1-6 carbon atoms; and
R$^6$ is a hydrogen atom or an alkyl group having 1-6 carbon atoms, at one terminal.

The polymer described above, when for example it comprises only one polymerizable monomer unit, can be represented by the following formula.

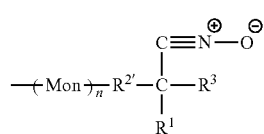

wherein R$^1$, R$^{2'}$ and R$^3$ are as defined in the formula (Ib),
Mon is a polymerizable monomer unit; and
n is any integer.

The polymer described above can be obtained by polymerizing one or more compounds of the formula (I) wherein R$^2$ is —R$^4$—R$^5$, and R$^3$ is —R$^4$—R$^6$, and one or more ring-opening polymerizable monomers. Therefore, the present invention provides a process for producing the polymer comprising one or more ring-opening polymerizable monomer units wherein the polymer has one group of the formula (Ib) at one terminal of the main chain, comprising a step of polymerizing one or more ring-opening polymerizable monomer by using the formula (Ib') as an initiator:

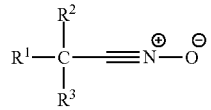

wherein:

$R^1$ is a hydrogen atom or a hydrocarbon group;

$R^2$ is —$R^4$—$R^5$;

$R^3$ is —$R^4$—$R^6$;

$R^4$ is a divalent organic group;

$R^5$ is OH, —SH, —COOH or —$NHR^9$;

$R^9$ is a hydrogen atom or an alkyl group having 1-6 carbon atoms; and $R^6$ is a hydrogen atom or an alkyl group having 1-6 carbon atoms.

The present invention provides a polymer comprising one or more ring-opening polymerizable monomer units wherein the polymer has a group of the formula (Ib):

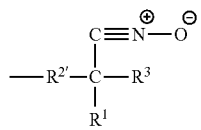

at one terminal of the main chain, and a nitrileoxide group at the other terminal.

When the polymer comprises, for example, only one polymerizable monomer unit, the polymer can by represented by the following formula:

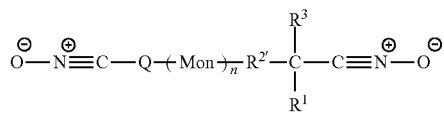

wherein:

$R^1$ is a hydrogen atom or a hydrocarbon group;

$R^{2'}$ is —$R^4$—$R^{5'}$— wherein $R^4$ is a carbon atom having a nitrileoxide group;

$R^3$ is —$R^4$—$R^6$;

$R^4$ is a divalent organic group;

$R^{5'}$ is —O—, —S—, —CO—O— or —$NR^9$—;

$R^9$ is a hydrogen atom or an alkyl group having 1-6 carbon atoms;

$R^6$ is a hydrogen atom or an alkyl group having 1-6 carbon atoms;

Mon is ring-opening polymerizable monomer unit;

n is any integer; and

Q is a divalent organic group.

The polymer can be obtained by polymerizing the compound of the formula (I) (provided that, $R^2$ is —$R^4$—$R^5$, and $R^3$ is —$R^4$—$R^6$) and one or more ring-opening polymerizable monomer, and stopping the reaction using a compound having a nitrileoxide group as a terminating agent, or providing a compound having a precursor group of the nitrileoxide group, and then converting the precursor group into the nitrileoxide group. In the formula -Q-CNO is derived from the terminating agent.

Examples of the terminating agent include, but are not particularly limited, for example, $(Ph)_2C=CHNO_2$ or $(Ph)HC=CHNO_2$ wherein Ph is a phenyl group.

For example, when $(Ph)_2C=CHNO_2$ is used as a terminator agent, a compound obtained after polymerization is the following compound.

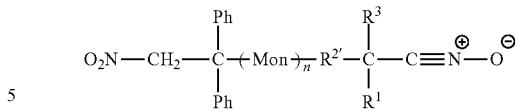

By dehydrating the compound, the following polymer having the nitrileoxide group at both terminals can be obtained.

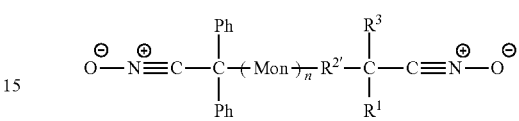

The present invention provides a polymer comprising one or more ring-opening polymerizable monomer units, wherein the polymer comprises one moiety of the formula (Ic) in the molecular chain:

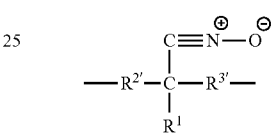

wherein:

$R^1$ is a hydrogen atom or a hydrocarbon group;

$R^{2'}$ and $R^{3'}$ are each independently —$R^4$—$R^{5'}$— wherein $R^4$ is attached to a carbon atom having a nitrileoxide group;

$R^4$ is a divalent organic group;

$R^{5'}$ is —O—, —S—, —CO—O— or —$NR^9$—, preferably —O—;

$R^9$ is a hydrogen atom or an alkyl group having 1-6 carbon atoms; and $R^{2'}$ and $R^{3'}$ are directly attached to the ring-opening polymerizable monomer unit.

When the polymer comprises, for example, only one type of the polymerizable monomer unit, the polymer can be represented by the following formula:

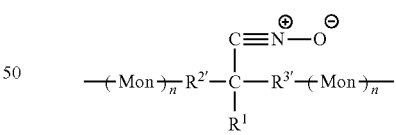

wherein $R^1$, $R^{2'}$ and $R^{3'}$ are as defined above,

Mon is a ring-opening polymerizable monomer unit, and n is each independently any integer.

The copolymer described above can obtained by polymerizing a compound of the formula (I) (provided that, both of $R^2$ and $R^{2'}$ are —$R^4$—$R^5$) and one or more ring-opening polymerizable monomer. Therefore, the present invention provides a process for producing a polymer comprising one or more ring-opening polymerizable monomer units and comprising one moiety of the formula (Ic) in the molecular main chain, comprising a step of polymerizing one or more ring-opening polymerizable monomer by using a compound of the formula (Ic') as an initiator:

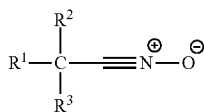

wherein:
$R^1$ is a hydrogen atom or a hydrocarbon group;
$R^2$ and $R^3$ are each independently, $-R^4-R^5$;
$R^4$ is a divalent organic group;
$R^5$ is OH, SH, COOH or $NHR^9$, preferably OH; and
$R^9$ is a hydrogen atom or an alkyl group having 1-6 carbon atoms.

Examples of one or more ring-opening polymerizable monomer used in preparing of the copolymer include, but are not particularly limited, preferably, monomer able to cause a ring-opening polymerization, for example, an oxetane, a fluorine-containing oxetane, an epoxy, a cyclic ester, and the like.

The monomer unit described above has a structure in which a ring-opening polymerizable monomer is opened, and includes, for example, the following groups.

Group Derived from an Epoxy Monomer
—CH(R)CH$_2$O— wherein R is H or an alkyl group which may be substituted,
—CH$_2$CH(R)O—

Group Derived from an Oxetane Monomer
—CH$_2$CH$_2$CH$_2$O— wherein a hydrogen atom may be substituted with a functional group such as an alkyl group, or the like, Group Derived from a Thioether
—CH$_2$CH(R)S—

Group Derived from a Cyclic Lactone
—C(O)—(CH$_2$)$_m$—O— wherein m is an integer of 2-5, and a hydrogen atom may be substituted with another functional group, Group Derived from a Cyclic Thiolactone
—C(S)—(CH$_2$)$_m$—O— wherein m is an integer of 2-5, and a hydrogen atom may be substituted with another functional group, Group Derived from a Cyclic Thionolactone
—(CH$_2$)$_m$—C(O)S— wherein m is an integer of 2-5, and a hydrogen atom may be substituted with another functional group, Group Derived from a Glycolide and an Analog Thereof
—C(O)—C(R)O— wherein R is a hydrogen atom or an alkyl group which may be substituted, Group Derived from a Morpholinedione
—C(O)—C(R)NH—C(O)—C(R)O— wherein R is a hydrogen atom or an alkyl group which may be substituted, Group Derived from a Cyclic Carbonate or a Lactide
—C(O)O—(CH$_2$)$_o$—O— wherein o is an integer of 1-4, and a hydrogen atom may be substituted with another functional group, Group Derived from a Cyclic Thiocarbonate
—C(S)O—(CH$_2$)$_o$—O— wherein o is an integer of 1-4, and a hydrogen atom may be substituted with another functional group, Group Derived from a Cyclic Thiocarbonate
—(CH$_2$)O—O—C(O)S— wherein a hydrogen atom may be substituted with another functional group, Group Derived from a Lactam
—NH—C(O)—(CH$_2$)$_p$— wherein p is an integer of 3-5, and a hydrogen atom may be substituted with another functional group, Group Derived from an α-Amino Acid-N-Carboxilic Anhydride (NCA) and an analog thereof
—C(O)—CHR—NH— wherein R is a hydrogen atom or a substituents such as an alkyl group, or the like, Group Derived from a Cycloalkane
—(CH$_2$)q-C(EWG)$_2$- wherein p is an integer of 2-3, EWG is an electron withdrawing functional group such as CN, C(O)OR, F, Cl, CF$_3$, NO$_2$, Group Derived from a Cyclobutane
—(CH$_2$)$_2$—C(EWG)$_2$-C(EWG)$_2$- wherein a hydrogen atom may be substituted with another functional group, and EWG is an electron withdrawing functional group such as CN, C(O)OR, F, Cl, CF$_3$, NO$_2$, Group Derived from a Cyclic Trisiloxane
—Si(R)(R')—O— wherein R and R' are an alkyl (preferably methyl), phenyl, vinyl, allyl, fluoroalkyl group, Group Derived from a Cyclic Siloxane
—Si(R)(R')O—Si(R)(R')—NR—Si(R)(R')O— wherein R, R' are a substituent, preferably a methyl group, a phenyl group, a vinyl group, an allyl group, particularly preferably a methyl group, Group Derived from 1-Oxa-2,5-Disilacyclopentane
—(CH$_2$)$_2$—Si(R)(R')—O—Si(R")(R''')— wherein R, R', R" and R''' are a substituent, preferably a methyl group, a phenyl group, a naphthyl group)

Group Derived from a Silacycloalkane
—Si(R)(R')—(CH$_2$)$_q$— wherein a hydrogen atom may be substituted with another functional group, Group Derived from Silacyclopentene
—Si(R)$_2$—CH$_2$—CH=CH—CH$_2$— wherein R is a substituent, preferably a methyl group, Group Derived from a Cyclic Disilane
—Si(R)(R')—Si(R")(R''')— wherein R, R', R" and R''' are a substituent, Group Derived from a Cyclic Phosphate Ester, a Cyclic Phosphonate Ester
—P(O)(OR or R)—O(CH$_2$)$_r$—O— wherein r is an integer of 4-8, R is a hydrogen atom, an alkyl group or an aryl group, Copolymer Backbone of an Epoxide or an Oxetane and a Carbon Dioxide, Copolymer Backbone of Ab Episulfide and a Carbon Disulfide
—(CH$_2$)$_q$—X—C(X)X— wherein X is O or S, Copolymer of an Epoxide and a Cyclic Acid Anhydride
—(CH$_2$)$_2$—O—C(O)—(CH$_2$)$_q$—C(O)—O—

The polymer of the present invention may has two or more monomer units described above.

The compound of the present invention is suitably used in various applications, for example, as a hydrophilizing agent, a surface treating agent, a polymerization initiator, a polymerizable monomer, a crosslinking agent, denaturation treatment agent, thermosetting resin, thermosetting elastomer, liquid rubber, low temperature property rubber, modifier of filler or reactive compatibilizing agent.

The present invention provides a composition comprising the polymer of the present invention:
(i) copolymer comprising a monomer unit of the formula (Ia) and one or more condensation polymerizable or addition polymerizable monomer units,
(ii) copolymer comprising a monomer unit of the formula (IIa) and one or more polymerizable monomer unit,
(iii) polymer comprising one or more ring-opening polymerizable monomer units, which has a group of the formula (Ib) at one terminal of the main chain,
(iv) polymer comprising one or more ring-opening polymerizable monomer units, which has a group of the formula (Ib) at one terminal of the main chain, and further has a nitrileoxide group at the other terminal, (v) polymer comprising one or more polymerizable monomer unit, which has one moiety of the formula (Ia) in the molecular main chain, or (vi) copolymer comprising a monomer unit of the formula (IIIa) and one or more polymerizable monomer unit.

The composition may contain one or more polymers. Furthermore, the composition may be composed of only the polymer of the present invention described above.

The polymer of the present invention (i)-(vi) described above has usually 1,000 or higher, preferably 2,000 or higher, particularly preferably 5,000 or higher of a number average molecular weight, but the number average molecular weight is not limited thereto, and can be appropriately selected depending on the application. The upper limit of the number average molecular weight may be, but not particularly limited, 2,000,000 or lower, preferably 1,000,000 or lower, and particularly preferably 500,000 or lower.

In one embodiment, the composition of the present invention may contain a material containing a group reactive with a nitrileoxide group in addition to the composition of the present invention. That is, in this embodiment, the composition of the present invention may be a mixture of the composition of the present invention and the material containing a group reactive with a nitrileoxide group.

In another embodiment, the composition of the present invention may be in the form of combining with other composition, for example the composition containing the material containing a group reactive with a nitrileoxide group. In this embodiment, the composition of the present invention and other composition may be mixed, preferably mixed just before use, and be used in a desired application.

In the above combination form, both the composition of the present invention and other composition may be in the form of a liquid, or one may be in the form of a solid (including a gel), or both may be in the form of a solid (including a gel).

The composition of the present invention may comprise a solvent. The solvent can be appropriately selected depending on components contained in the composition.

In a preferable embodiment, the composition of the present invention is used for applying to the material containing a group reactive with a nitrileoxide group.

Examples of the "group reactive with a nitrileoxide group" include a group having a double bond (C=C, C=N, N=N, C=S, P(V)=C, C=P(III), C=As, C=Se, B=N, P(V)=N, C=O), or a group having a triple bond (C≡C, C≡N, C≡P), specifically an alkenyl group, an alkynyl group, and a nitrile group.

Examples of the "material" in the material containing a group reactive with a nitrileoxide group include, but are not particularly limited to, for example, glass materials, resin materials, compounds which is able to be applied with a crosslinking agent, in particular polymeric compounds (for example, natural rubbers, synthetic rubbers), and various compounds.

The polymer contained the composition of the present invention contains a nitrileoxide group, thus has high reactivity, thereby being able to modify various base material, compounds, etc., and to provide them with desired property.

In particular, (i) a composition comprising a copolymer comprising a monomer unit of the formula (Ia) and one or more condensation polymerizable or addition polymerizable monomer units, and (ii) a composition comprising a copolymer comprising a monomer unit of the formula (IIa) and one or more radical polymerizable monomer units, and (iv) a composition comprising a polymer comprising one or more ring-opening polymerizable monomer units, which has a group of the formula (Ib) at the terminal of the main chain, and a nitrileoxide group at the other terminal may be useful as a crosslinking agent. In this case, in particular, (i) and (ii) compositions are preferable.

In particular, (iii) a composition comprising a polymer comprising one or more ring-opening polymerizable monomer units, which has a group of the formula (Ib) at one terminal or both terminals of the main chain, and (iv) a composition comprising a polymer comprising one or more ring-opening polymerizable monomer units, which has one moiety of the formula (Ia) in the main chain may be useful as a grafting agent. In this case, in particular, (iii) a composition comprising a polymer comprising one or more radical polymerizable monomer units, has a group of the formula (Ib) at one terminal of the main chain and (iv) composition are preferable.

In one embodiment, the composition of the present invention is a hydrophilizing agent.

The hydrophilizing agent of the present invention comprises at least one polymer having a group of the formula (Ib) at the terminal of the main chain of the present invention.

The base material applied with the hydrophilizing agent of the present invention is not limited as long as it has a reactive group with the nitrileoxide group. For example, by reacting the hydrophilizing agent of the present invention with a compound having low hydrophilic, the hydrophilic of the compound can be increased. In addition, by reacting the hydrophilizing agent of the present invention with a surface of a non-hydrophilic resin, the hydrophilic of the surface of the resin can be increased.

In one embodiment, the hydrophilization described above can be performed by mixing the composition of the present invention and other polymeric material or molding (preferably film-forming) other polymeric material, and applying the composition of the present invention to the surface thereof.

In a preferable embodiment, the hydrophilized polymeric material is molded into a porous polymer membrane.

Therefore, the present invention provides a membrane composed from a mixture of the compound of the present invention and other polymeric material.

In a preferable embodiment, the other polymeric materials are fluorine-containing polymer, typically a vinylidene fluoride polymer, preferably polyvinylidene fluoride or a copolymer having a vinylidene fluoride unit.

The compounds of the present invention can be added to the fluorine-containing polymer such that its concentration is 0.5 to 50% by mass to provide a composition. A more preferable lower limit is 5% by weight, more preferable lower limit is 10% by mass, and a more preferable upper limit is 30% by mass.

When the fluorine-containing polymer is a vinylidene fluoride polymer, it is possible to mix it with the compounds of the present invention by melt-kneading, thereby forming a porous polymer membrane having excellent properties. In this respect, the composition is preferably a composition obtained by melt-kneading the compound of the present invention and polyvinylidene fluoride or a copolymer having a vinylidene fluoride unit.

The weight average molecular weight of the polyvinylidene fluoride is, from the viewpoint of mechanical strength and processability of the polymer porous membrane, preferably 30,000 to 2,000,000, more preferably 50,000 to 1,000,000.

The vinylidene fluoride polymer may be a homopolymer consisting of vinylidene fluoride units, or may be a modified polymer comprising a vinylidene fluoride unit and other monomer unit. In the modified polymer, as the other monomer, a monomer copolymerizable with vinylidene fluoride can be used, and examples of the other monomer include tetrafluoroethylene (TFE), hexafluoropropene (HFP), chlorotrifluoroethylene (CTFE), trifluoroethylene, perfluoroalkyl vinyl ethers, fluoroalkyl ethylene, trifluoro propylene, pentafluoropropylene, trifluorobutene, tetrafluoroisobutene, hexafluoroisobutene, a fluoromonomer of the general formula: $CH_2=CFRf$ (wherein Rf is a linear or branched fluoroalkyl group having 1 to 12 carbon atoms), and the like. In polyvinylidene fluoride, the molar ratio of the vinylidene fluoride unit and the other monomeric units (vinylidene fluoride unit/other monomer units) is preferably greater than 99/1 and less than 100/0.

Examples of the copolymer including a vinylidene fluoride unit include vinylidene fluoride/tetrafluoroethylene copolymers and vinylidene fluoride/hexafluoropropylene copolymers. In order to achieve good mechanical strength and alkali resistance, the copolymer including a vinylidene fluoride unit is particularly preferably a vinylidene fluoride/tetrafluoroethylene copolymer.

In order to achieve good membrane formability and alkali resistance, the vinylidene fluoride/tetrafluoroethylene copolymer preferably satisfies a ratio by mole between the vinylidene fluoride unit and the tetrafluoroethylene unit (vinylidene fluoride unit/tetrafluoroethylene unit) of 50 to 99/50 to 1. Examples of such a polymer include VT series (DAIKIN INDUSTRIES, Ltd.). The ratio by mole between the vinylidene fluoride unit and the tetrafluoroethylene unit in the vinylidene fluoride/tetrafluoroethylene copolymer is more preferably 50 to 95/50 to 5, still more preferably 50 to 90/50 to 10. In addition to the vinylidene fluoride/tetrafluoroethylene copolymer consisting only of a vinylidene fluoride unit and a tetrafluoroethylene unit, the vinylidene fluoride/tetrafluoroethylene copolymer may be a ternary or higher copolymer having not only a vinylidene fluoride unit and a tetrafluoroethylene unit but also any other units such as a hexafluoropropylene unit, a chlorotrifluoroethylene unit, and a perfluorovinyl ether unit to the extent that these units do not deteriorate the characteristics The weight average molecular weight of the copolymer including a vinylidene fluoride unit varies in accordance with the application of the resulting porous polymer membrane. In order to achieve good mechanical strength and membrane formability, the weight average molecular weight thereof is preferably 10,000 or more. It is more preferably 30,000 to 2,000,000, still more preferably 50,000 to 1,000,000, particularly preferably 100,000 to 800,000. The weight average molecular weight can be determined by gel permeation chromatography (GPC).

In one embodiment, the other polymeric material may comprise a resin other than vinylidene fluoride polymer.

Examples of the resin other than vinylidene fluoride polymer include polyethylene resin, polypropylene resin, acrylic resin, polyacrylonitrile, acrylonitrile-butadiene-styrene (ABS) resin, polystyrene resin, acrylonitrile-styrene (AS) resin, vinyl chloride resin, polyethylene terephthalate, polyamide resin, polyacetal resin, polycarbonate resin, modified polyphenylene ether resin, polyphenylene sulfide resin, polyamide imide resin, polyether imide resin, polysulfone resin, polyether sulfone resin, and mixtures and copolymers thereof. Resin miscible with these resins may also be mixed.

The resin other than vinylidene fluoride polymer is preferably at least one selected from the group consisting of a polyethylene resin, a polypropylene resin, and an acrylic resin.

The polyethylene resin is a resin comprising an ethylene homopolymer or an ethylene copolymer. The polyethylene resin may comprise multiple ethylene copolymers. Examples of the ethylene copolymer include copolymers of ethylene and at least one selected from unsaturated linear hydrocarbons such as propylene, butene, and pentene.

The polypropylene resin is a resin comprising a propylene homopolymer or a propylene copolymer. The polypropylene resin may comprise multiple propylene copolymers. Examples of the propylene copolymer include copolymers of propylene and at least one selected from the group consisting of unsaturated linear hydrocarbons such as ethylene, butene, and pentene.

The acrylic resin is a polymeric compound mainly containing acrylic acid, methacrylic acid or a derivative thereof, such as a polymer of acrylamide or acrylonitrile. Particularly preferred are acrylate resin and methacrylate resin.

The resin other than vinylidene fluoride polymer is most preferably acrylic resin.

The characteristics of the resulting porous polymer membrane such as membrane strength, water permeability, and the blocking performance can be adjusted by adjusting the type and the amount of the resin other than vinylidene fluoride polymer.

In order to achieve hydrophilization, to control phase separation, and to improve the mechanical strength, the composition of the present invention may further contain additives such as polyvinylpyrrolidone, polymethyl methacrylate resin, polyethylene glycol, montmorillonite, $SiO_2$, $TiO_2$, $CaCO_3$, and polytetrafluoroethylene The porous polymer membrane described above can be produced by any of various methods. Examples thereof include phase separation, melt extraction, vapor solidification, stretching, etching, sintering of a polymer sheet into a porous membrane, crushing of a bubble-containing polymer sheet into a porous membrane, and electrospinning.

The melt extraction is a method of forming a porous structure by melt-kneading inorganic particles and organic liquid matter with a mixture; extrusion-molding the kneaded matter through a die or molding it with a press at a temperature not lower than the melting points of the compound of the present invention and the fluorine-containing polymer; cooling and solidifying the molded article; and then extracting the organic liquid matter and the inorganic particles.

The vapor solidification is a method of forcedly supplying saturated vapor or vapor containing mist of one or both of a nonsolvent and a poor solvent which are compatible with a good solvent and do not dissolve the compound of the present invention and the fluorine-containing polymer for at least one surface of a membrane-like article formed from a composition prepared by dissolving the compound of the present invention and the fluorine-containing polymer in a good solvent.

In a preferable embodiment, the porous polymer membrane of the present invention is preferably produced by the phase separation because the pore size is easily controlled. Examples of the phase separation include thermally induced phase separation (TIPS) and nonsolvent-induced phase separation (NIPS).

In the case of thermally induced phase separation, the porous polymer membrane of the present invention can be produced by a method including a step of dissolving the compound of the present invention and the fluorine-containing polymer in a solvent that is a poor solvent or a good solvent at a relatively high temperature to provide a composition, and a step of cooling and solidifying the composition.

The composition prepared by dissolving the compound of the present invention and the fluorine-containing polymer in a solvent is in the form of a uniform single-phase liquid when it is maintained at a temperature higher than what is called a cloud point. In contrast, phase separation occurs at a temperature not higher than the cloud point so that the composition is separated into two phases, i.e., a polymer-rich phase and a solvent-rich phase. When the temperature reaches the crystallization temperature or lower, the polymer matrix is immobilized, so that a porous membrane is formed.

In the case of thermally induced phase separation, the sum of the amounts of the compound of the present invention and the fluorine-containing polymer in the composition is preferably 10 to 60% by mass relative to the sum of the amounts of the compound of the present invention and the fluorine-containing polymer, and the solvent. It is more preferably 15 to 50% by mass.

The viscosity of the composition can be adjusted within an appropriate range by adjusting the concentration of the compound of the present invention and the fluorine-containing polymer within an appropriate range. If the viscosity of the composition is beyond an appropriate range, the porous polymer membrane may not be formed The poor solvent is a solvent that is not capable of dissolving 5% by mass or more of the compound of the present invention and the fluorine-containing polymer at a temperature lower than 60° C. but capable of dissolving 5% by mass or more thereof at a temperature of 60° C. or higher and not higher than the melting points of the resins. In contrast to the poor solvent, a solvent that is capable of dissolving 5% by mass or more of the resins even at a temperature lower than 60° C. is called a good solvent. A solvent that neither dissolves nor swells the resins until the temperature reaches the melting points of the resins or the boiling point of the liquid is called a nonsolvent.

Examples of the poor solvent include middle-chain-length alkyl ketones, esters, glycol esters and organic carbonates such as cyclohexanone, isophorone, γ-butyrolactone, methyl isoamyl ketone, dimethyl phthalate, diethyl phthalate, dibutyl phthalate, aliphatic polyhydric alcohols, propylene glycol methyl ether, propylene carbonate, diacetone alcohol, and glycerol triacetate, and solvent mixtures thereof. Fluorosolvents such as HFC-365, diphenyl carbonate, methyl benzoate, diethylene glycol ethyl acetate, or benzophenone may also be used. Even with respect to a solvent mixture of a nonsolvent and a poor solvent, a solvent that satisfies the definition of a poor solvent is defined as a poor solvent.

In the case of thermally induced phase separation, a solvent for the composition is preferably, but not limited to, a poor solvent. As a result of examining the behavior of phase separation of a fluoropolymer, a good solvent may be used in some cases.

Examples of the good solvent include fluorosolvents such as HCFC-225, lower alkyl ketones, esters, and amides such as N-methyl-2-pyrrolidone, dimethyl sulfoxide, dimethyl acetamide, dimethyl formamide, methyl ethyl ketone, acetone, methanol, tetrahydrofuran, tetramethylurea, and trimethyl phosphate, and solvent mixtures thereof.

Examples of the nonsolvent include water, aliphatic hydrocarbons, aromatic hydrocarbons, aromatic polyhydric alcohols, and chlorinated hydrocarbons or other chlorinated organic liquids such as hexane, pentane, benzene, toluene, carbon tetrachloride, o-dichlorobenzene, trichloroethylene, ethylene glycol, diethylene glycol, triethylene glycol, tetraethylene glycol, propylene glycol, butylene glycol, pentane diol, hexane diol, methanol, ethanol, propanol, and low molecular weight polyethylene glycol, and solvent mixtures thereof.

In the case of thermally induced phase separation, the step of providing a composition is preferably a step of dissolving the compound of the present invention and the fluorine-containing polymer in a solvent that is a poor solvent or a good solvent at 20° C. to 270° C. The dissolving temperature is preferably 30° C. to 250° C. When dissolved at a relatively high temperature, the compound of the present invention and the fluorine-containing polymer can be at a high concentration. This enables production of a porous polymer membrane having high mechanical strength. If the concentration of the compound of the present invention and the fluorine-containing polymer is too high, the resulting porous polymer membrane may have a low porosity, resulting in poor water permeability. If the viscosity of the prepared composition is beyond an appropriate range, a porous membrane may not be formed.

The composition is preferably cooled and solidified by a method of ejecting the composition into a cooling bath through a die, for example. For the porous polymer membrane in the form of a flat membrane, a method of casting and immersing the composition in a cooling bath is also one preferable method.

Those able to be used as a cooling liquid for the cooling bath have a temperature lower than that of the composition. Examples thereof include a liquid containing a solvent that is a poor solvent or a good solvent at a temperature of 0° C. to 80° C. and a concentration of 60 to 100% by mass. The cooling liquid may be a nonsolvent or a nonsolvent containing a poor solvent or a good solvent.

In the production of the porous polymer membrane of the present invention, important features are the concentration of the composition, the constitution of the solvent that dissolves the compound of the present invention and the fluorine-containing polymer, and the constitution of the cooling liquid constituting the cooling bath. The porous structure of the porous polymer membrane can be adjusted by adjusting these compositions.

For example, one surface and the other surface of the porous polymer membrane may have different combinations of the constitution of the composition and the constitution of a cooling liquid. Thereby, the structure of the one surface of the porous polymer membrane may be made different from the structure of the other surface.

In producing the porous polymer membrane by nonsolvent-induced phase separation, for example, the porous polymer membrane is preferably produced by a method including a step of dissolving the compound of the present invention and the fluorine-containing polymer in a solvent to provide a composition, and a step of ejecting the composition into a solidification bath containing a nonsolvent through a die.

Immersion of the composition in a solidification bath containing a nonsolvent can cause nonsolvent-induced phase separation with the concentration gradient between the solvent and nonsolvent in the composition and the solidification bath used as a power for phase separation. In such a method, a fine skin layer is first formed on the outer surface where phase separation occurs due to replacement between the solvent and the nonsolvent. Then, the phase-separating phenomenon proceeds toward the inside of the membrane. As a result, after the formation of the skin layer, an asymmetric membrane can also be produced in which the pore size continually increases toward the inside of the membrane.

In the case of nonsolvent-induced phase separation, the composition preferably comprises the compound of the present invention, the fluorine-containing polymer, and the solvent. The composition further comprising a nonsolvent in addition to the compound of the present invention, the fluorine-containing polymer, and the solvent is also one preferable embodiment.

The composition preferably contains 5 to 60% by mass of the compound of the present invention, and the fluorine-containing polymer relative to the sum of the amounts of the compound of the present invention, the fluorine-containing polymer, the solvent, and the nonsolvent (if the composition contains no nonsolvent, the sum of the amounts of the compound of the present invention, the fluorine-containing polymer, and the solvent). This value is more preferably 10 to 50% by mass. The composition preferably contains 0.1 to 10% by mass of the nonsolvent relative to the sum of the amounts of the compound of the present invention, the fluorine-containing polymer, the solvent, and the nonsolvent. This value is more preferably 0.5 to 8% by mass. The viscosity of the composition can be adjusted within an appropriate range by adjusting the fluoropolymer concentration within an appropriate range. If the viscosity of the composition is beyond an appropriate range, a porous polymer membrane may not be formed.

The composition may be at room temperature or may be heated. For example, the composition is preferably at 10° C. to 75° C.

The solvent to be used in nonsolvent-induced phase separation may be any solvent exemplified for thermally induced phase separation. The solvent may be either a poor solvent or a good solvent, and is preferably a good solvent. The nonsolvent may be any nonsolvent exemplified for thermally induced phase separation.

With respect to a solidification liquid to be used as the solidification bath, solidification is preferably achieved using a liquid containing a nonsolvent. The liquid may further contain a poor solvent and a good solvent. The nonsolvent may be any nonsolvent exemplified for thermally induced phase separation. For example, water may suitably be used.

In production of the porous polymer membrane of the present invention, the thermally induced phase separation and the nonsolvent-induced phase separation may be used in combination.

The nonsolvent-induced phase separation and the thermally induced phase separation can provide a porous membrane by ejecting a composition prepared by dissolving the compound of the present invention, the fluorine-containing polymer in a solvent through a die and solidifying the composition. Examples of the die include slit dies, double orifice spinnerets, and triple orifice spinnerets.

In the case of producing a porous polymer membrane in the form of a hollow fiber membrane, the die to be used is preferably a double orifice spinneret or a triple orifice spinneret for spinning hollow fiber membranes.

In the case of a double orifice spinneret, the composition is emitted from the outer tube of the double orifice spinneret, while a hollow-forming fluid such as ion exchange water is emitted from the inner tube, and then the composition is solidified in a solidification bath or a cooling bath. Thereby, a hollow fiber membrane can be produced.

The hollow-forming fluid is usually in the form of gas or liquid. In thermally induced phase separation, a liquid containing a poor solvent or a good solvent at a concentration of 60 to 100%, which is the same as the cooling liquid, can preferably be used. Alternatively, a nonsolvent or a nonsolvent containing a poor solvent or a good solvent may also be used. In the nonsolvent-induced phase separation, the hollow-forming fluid is preferably the aforementioned nonsolvent. For example, water such as ion exchange water is preferred. The aforementioned nonsolvent may contain a poor solvent or a good solvent.

In thermally induced phase separation, the hollow-forming fluid is preferably the aforementioned solvent. For example, a poor solvent such as glycerol triacetate is preferred. In thermally induced phase separation, nitrogen gas may also be used.

A hollow fiber membrane with two structures may be formed by varying the constitution of a hollow-forming fluid and of a cooling liquid or solidification liquid. The hollow-forming fluid may be supplied in the cooled state. If the cooling force of the cooling bath alone is sufficient for solidifying the hollow fiber membrane, the hollow-forming fluid may be supplied without cooling.

A triple orifice spinneret is suitable for the cases of using two resin solutions. For example, two compositions are emitted from the outer tube and the middle tube, respectively, of the triple orifice spinneret, while a hollow-forming liquid is emitted from the inner tube, and then the compositions are solidified in a solidification bath or a cooling bath. Thereby, a hollow fiber membrane can be formed. Alternatively, a composition is emitted from the outer tube of the triple orifice spinneret, a resin solution containing a resin other than the compound of the present invention, the fluorine-containing polymer is emitted from the middle tube, and a hollow-forming fluid is emitted from the inner tube, while the emitted materials are solidified in a solidification bath or a cooling bath. Thereby, a hollow fiber membrane can be formed. The resin other than the compound of the present invention, the fluorine-containing polymer may be any of those mentioned above. Preferred is the aforementioned thermoplastic resin, and more preferred is acrylic resin.

As mentioned above, production of a hollow fiber membrane by a method using a double orifice spinneret or a triple orifice spinneret is preferred in that the amount of a solidification liquid or a cooling liquid can be smaller than in production of a flat membrane.

The porous polymer membrane of the present invention in the form of a hollow fiber membrane may further have a fluoropolymer layer or a resin layer of a resin other than the compound of the present invention, the fluorine-containing polymer on the outer surface or the inner surface of the hollow fiber membrane formed by the above method.

The fluoropolymer layer or the resin layer can be formed by applying a composition or a resin solution to the outer surface or the inner surface of the hollow fiber membrane. A method of applying the composition or the resin solution to the outer surface of the hollow fiber membrane is preferably immersing the hollow fiber membrane in the composition or the resin solution or dropping the composition or the resin solution onto the hollow fiber membrane. A method of applying the composition or the resin solution to the inner surface of the hollow fiber membrane is preferably injecting the composition or the resin solution into the hollow fiber membrane. The amount of the composition or the resin solution to be applied can preferably be controlled by a method of controlling the amount itself of the composition or the resin solution to be applied, as well as a method of partially scraping off or blowing with an air knife the composition or the resin solution after immersing the porous membrane in the composition or the resin solution or applying the composition or the resin solution to the porous membrane, or a method of adjusting the concentration thereof upon application.

The porous polymer membrane in the form of a flat membrane can be produced by casting the composition and immersing the composition in a cooling bath or a solidification bath. Alternatively, such a membrane can be produced by ejecting the composition into a cooling bath or a solidification bath through a slit die.

The porous polymer membrane in the form of a composite membrane comprising a porous base can be produced by immersing a porous base in the composition or by applying the composition to at least one face of a porous base, for example.

The aforementioned production method can provide a porous polymer membrane having low contact angle. Still, if the water permeability is insufficient, the porous membrane produced by the above production method may be further stretched so that the porous polymer membrane of the present invention can be obtained.

The pore size of the porous polymer membrane can be controlled by, for example, mixing an additive for controlling the pore size with the composition, and then allowing the additive to be eluted during or after formation of the porous structure of the compound of the present invention, the fluorine-containing polymer. The additive may be made to remain in the porous membrane.

In each of the nonsolvent-induced phase separation and the thermally induced phase separation, the composition may contain an additive. Elution of the additive after formation of the porous structure enables control of the pore size of the porous polymer membrane. The additive may be made to remain in the porous membrane, if necessary.

Examples of the additive include organic compounds and inorganic compounds. The organic compounds are preferably those dissolved or uniformly dispersed in a solvent constituting the composition. They are also preferably those dissolved in a nonsolvent contained in the solidification liquid for nonsolvent-induced phase separation or a solvent contained in the cooling liquid for thermally induced phase separation.

Examples of the organic compounds include water-soluble polymers such as polyvinylpyrrolidone, polyethylene glycol, polyvinyl alcohol, polyethylene imine, polyacrylic acid, and dextran, surfactants such as Tween 40 (polyoxyethylene sorbitan monopalmitate), glycerin, and saccharides.

The inorganic compounds are preferably water-soluble compounds. Examples thereof include calcium chloride, lithium chloride, and barium sulfate.

The average pore size on the surface can also be controlled by controlling the phase separation rate in accordance with the type, concentration, and temperature of a nonsolvent in the solidification liquid without any additive. In general, the higher the phase separation rate is, the smaller the average pore size on the surface is, whereas the lower the rate is, the larger the size is. Addition of a nonsolvent to the composition is also effective to control the phase separation rate.

In order to achieve hydrophilization, to control phase separation, and to improve mechanical strength, the composition may further contain any additives such as polyvinylpyrrolidone, polymethyl methacrylate resin, montmorillonite, $SiO_2$, $TiO_2$, $CaCO_3$, and polytetrafluoroethylene.

In order to improve the water permeability, the porous polymer membrane may be treated with an alkali. The alkali herein means a NaOH aqueous solution, a KOH aqueous solution, ammonia water, an amine solution, or the like. They may contain any alcohol such as ethanol and methanol, and organic solvents. The alkali preferably contains an alcohol, but it is not limited thereto.

By applying the compound of the present invention to the porous polymer membrane, the compound can form a coating to provide hydrophilicity. As the porous polymer membrane, those described above are able to be used.

Therefore, the present invention provides a membrane obtained by applying the compound of the present invention to the surface of the membrane of the other polymeric material.

The compound of the present invention may contain an organic solvent, and when the compound contains the organic solvent, it is possible to easily applied.

Examples of the organic solvent include the following solvents:

aromatic hydrocarbons such as benzene, toluene, xylene, naphthalene and solvent naphtha;

esters such as methyl acetate, ethyl acetate, propyl acetate, n-butyl acetate, isobutyl acetate, isopropyl acetate, isobutyl acetate, cellosolve acetate, propylene glycol methyl ether acetate, carbitol acetate, diethyl oxalate, ethyl pyruvate, ethyl-2-hydroxybutyrate, ethyl acetoacetate, amyl acetate, methyl lactate, ethyl lactate, methyl 3-methoxypropionate, ethyl 3-methoxypropionate, methyl 2-hydroxyisobutyrate and ethyl 2-hydroxyisobutyrate;

ketones such as acetone, methyl ethyl ketone, cyclohexanone, methyl isobutyl ketone, cyclohexanone, methyl isobutyl ketone, 2-hexanone, cyclohexanone, methyl amino ketone and 2-heptanone;

glycol ethers such as ethyl cellosolve, methyl cellosolve, methyl cellosolve acetate, ethyl cellosolve acetate, propylene glycol monomethyl ether, propylene glycol monoethyl ether, propylene glycol monobutyl ether, propylene glycol monomethyl ether acetate, propylene glycol monoethyl ether acetate, propylene glycol monobutyl ether acetate, dipropylene glycol dimethyl ether and ethylene glycol monoalkyl ether;

alcohols such as methanol, ethanol, iso-propanol, n-butanol, isobutanol, tert-butanol, sec-butanol, 3-pentanol, octyl alcohol, 3-methyl-3-methoxybutanol and tert-amyl alcohol;

cyclic ethers such as tetrahydrofuran, tetrahydropyran and dioxane; amides such as N,N-dimethylformamide and N,N-dimethylacetamide;

ether alcohols such as methyl cellosolve, cellosolve, iso-propyl cellosolve, butyl cellosolve and diethylene glycol monomethyl ether;

1,1,2-trichloro-1,2,2-trifluoroethane, 1,2-dichloro-1,1,2,2-tetrafluoroethane, dimethyl sulfoxide, and the like. Also, there are solvent mixtures of two or more thereof.

Examples of the fluorine-containing solvent include the following solvents:

for example, $CH_3CCl_2F$ (HCFC-141b), $CF_3CF_2CHCl_2$/$CClF_2CF_2CHClF$ mixture (HCFC-225), perfluorohexane, perfluoro(2-butyltetrahydrofuran), methoxy-nonafluorobutane, 1,3-bistrifluoromethylbenzene, and in addition, fluorine-containing alcohols such as $H(CF_{2c}F_2)_nCH_2OH$ (n: an integer of 1-3), $F(CF_2)_nCH_2OH$ (n: an integer of 1-5), $CF_3CH(CF_3)OH$; benzotrifluoride, perfluorobenzene, perfluoro(tributylamine), $C_1CF_2CFClCF_2CFCl_2$, and the like.

The fluorine-containing solvent may be single, or a mixed solvent of the fluorine-containing solvents or a fluorine-free solvent and one or more fluorine-containing solvents.

Among them, alcohol and ketone, butyl acetate, N,N-dimethylformamide, N,N-dimethylacetamide, or dimethyl sulfoxide is preferable, furthermore iso-propanol and methyl ethyl ketone, methyl isobutyl ketone, N,N-dimethylformamide, N,N-dimethylacetamide, dimethylsulfoxide is most preferable. When the compound of the present invention contains the organic solvent, the compound preferably contains the above-mentioned fluorine-containing solvent at 5-60% by mass. Applying of hydrophilizing agent is able to be performed by a known method, for example, a spin coating method, a bar code method, a casting method, a spray method, an electrospinning method, or the like. The compound of the present invention may further contain additives usually used in paints, such as curing agents, curing accelerators, pigments, dispersants, thickeners, preservatives, ultraviolet absorbers, antifoaming agents, conventional additives, leveling agents, or the like.

The porous polymer membrane is suitable for drinking water production, water treatment, a microfiltration membrane or ultrafiltration membrane used in water treatment of waste water treatment and the like. The porous polymer membrane is particularly preferably a porous polymer membrane for the water treatment.

In addition, the p porous polymer membrane is suitably used also in the food field, battery field, or the like.

In the food field, the porous polymer membrane can be used for the purpose of separation of yeast used in the fermentation, or concentration of liquid.

In the battery field, the porous polymer membrane can be used as a battery separator to which electrolytes can permeate and products generated in cell reaction cannot permeate.

In one embodiment, the composition of the present invention is a surface treatment agent.

The surface treatment agent of the present invention comprises at least one polymer having a group of the formula (Ib) at the terminal of the main chain of the present invention as a main ingredient or an active ingredient, and can form surface-treating layer having water-repellency, oil-repellency, antifouling property, friction durability, surface slip property, water-proof property or the like, thus is used as an antifouling coating agent or a water-proof coating agent. The "main ingredient" means an ingredient whose contents is more than 50% in the surface treatment agent, and the "active ingredient" means an ingredient which remains on a material to be surface-treated to form a surface-treating layer, thereby exhibiting some function (water-repellency, oil-repellency, antifouling property, surface slip property, friction durability, etc.).

The surface treatment agent of the present invention has an advantageous than a surface treatment agent containing a fluorine-containing silane compound which is suitably applied mainly to a glass material, and a surface treatment agent containing a compound having a curable moiety (for example, double bond) which is suitably applied mainly to a resin material in point that it can be suitably applied to any base material as long as it is reactive with a nitrileoxide group.

The composition of the surface treatment agent of the present invention may be selected depending on a function which is desired in the surface-treating layer.

For example, the surface treatment agent may comprise a fluoropolyether compound which may be also understood as a fluorine-containing oil, preferably a perfluoro(poly)ether compound (hereinafter, referred to as a "fluorine-containing oil") in addition to the polymer having a group of the formula (Ib) at the terminal of the main chain of the present invention. The fluorine-containing oil contributes to increasing of surface slip property of the surface-treating layer.

The fluorine-containing oil may be contained in the surface-treating agent of the present invention, for example, at 0-300 parts by mass, preferably 50-200 parts by mass with respect to 100 parts by mass of the polymer having a group of the formula (Ib) at the terminal of the main chain of the present invention (as the total mass when two or more compounds are used; hereinafter the same shall apply).

Examples of the above-mentioned fluorine-containing oil include, but are not particularly limited to, for example, a compound (a perfluoropolyether compound) of the following general formula (A).

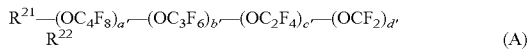

(A)

In the formula, $R^{21}$ represents an alkyl group having 1-16 carbon atoms which may be substituted by one or more fluorine atoms, preferably an alkyl group having 1-3 carbon atoms which may be substituted by one or more fluorine atoms. Preferably, the alkyl which may be substituted by one or more fluorine atoms is a fluoroalkyl group in which a terminal carbon atom is $CF_2H$— and the other carbon atoms are fully substituted by a fluorine atom, or a perfluoroalkyl group, more preferably a perfluoroalkyl group.

$R^{22}$ represents a hydrogen atom, a fluorine atom, or an alkyl group having 1-16 carbon atoms which may be substituted by one or more fluorine atoms, preferably an alkyl group having 1-3 carbon atoms which may be substituted by one or more fluorine atoms. Preferably, the alkyl which may be substituted by one or more fluorine atoms is a fluoroalkyl group in which a terminal carbon atom is $CF_2H$— and the other carbon atoms are fully substituted by a fluorine atom, or a perfluoroalkyl group, more preferably a perfluoroalkyl group.

Subscripts a', b', c' and d' represent the repeating number of each of three repeating units of perfluoropolyether which constitute a main backbone of the polymer, and are each independently an integer of 0 or more and 300 or less, and the sum of a', b', c' and d' is at least 1, preferably 1-100. The occurrence order of the respective repeating units in parentheses with the subscript a', b', c' or d' is not limited in the formula. Among these repeating units, the —$(OC_4F_8)$— group may be any of —$(OCF_2CF_2CF_2CF_2)$—, —$(OCF(CF_3)CF_2CF_2)$—, —$(OCF_2CF(CF_3)CF_2)$—, —$(OCF_2CF_2CF(CF_3))$—, —$(OC(CF_3)_2CF_2)$—, —$(OCF_2C(CF_3)_2)$—, —$(OCF(CF_3)CF(CF_3))$—, —$(OCF(C_2F_5)CF_2)$— and —$(OCF_2CF(C_2F_5))$—, preferably —$(OCF_2CF_2CF_2CF_2)$. The —$(OC_3F_6)$— group may be any of —$(OCF_2CF_2CF_2)$—, —$(OCF(CF_3)CF_2)$— and —$(OCF_2CF(CF_3))$—, preferably —$(OCF_2CF_2CF_2)$—. The —$(OC_2F_4)$— group may be any of —$(OCF_2CF_2)$— and —$(OCF(CF_3))$—, preferably —$(OCF_2CF_2)$—.

Examples of the perfluoropolyether compound of the above general formula (A) include a compound of any of the following general formulae (A1) and (A2) (may be one compound or a mixture of two or more compounds).

(A1)

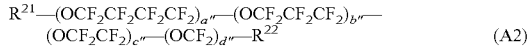

(A2)

In these formulae:

$R^{21}$ and $R^{22}$ are as defined above; in the formula (A1), b" is an integer of 1 or more and 100 or less; and in the formula (A2), a" and b" are each independently an integer of 1 or more and 30 or less, and c" and d" are each independently an integer of 1 or more and 300 or less. The occurrence order of the respective repeating units in parentheses with the subscript a", b", c" or d" is not limited in the formulae.

The compound of the general formula (A1) and the compound of the general formula (A2) may be used alone or in combination.

When the polymer having a group of the formula (Ib) at the terminal of the main chain of the present invention contains a perfluoroalkyl group, the fluorine-containing oil may be a compound of the general formula $Rf^1$—F wherein $Rf^1$ is a perfluoroalkyl group contained in the polymer of the present invention. In this case, the compound of $Rf^1$—F is preferable because the compound has high affinity for the polymer of the present invention.

The surface treatment agent may comprise a silicone compound which may be also understood as a silicone oil (hereinafter referred to as a "silicone oil") in addition to the polymer having a group of the formula (Ib) at the terminal of the main chain of the present invention. The silicone oil contributes to increasing of surface slip property of the surface-treating layer.

The silicone oil may be contained in the surface treatment agent, for example, at 0-300 parts by mass, preferably 50-200 parts by mass with respect to 100 parts by mass of the polymer having a group of the formula (Ib) at the terminal of the main chain of the present invention.

Examples of the above-mentioned silicone oil include, for example, a liner or cyclic silicone oil having 2,000 or less siloxane bonds. The liner silicone oil may be so-called a straight silicone oil and a modified silicon oil. Examples of the straight silicone oil include dimethylsilicone oil, methylphenylsilicone oil, and methylhydrogensilicone oil. Examples of the modified silicone oil include that which is obtained by modifying a straight silicone oil with alkyl, aralkyl, polyether, higher fatty acid ester, fluoroalkyl, amino, epoxy, carboxyl, alcohol, or the like. Examples of the cyclic silicone oil include, for example, cyclic dimethylsiloxane oil.

The present invention also provides an article comprising a base material and a layer (a surface-treating layer) which is formed from the polymer having a group of the formula (Ib) at the terminal of the main chain of the present invention or the surface treatment agent (hereinafter, representatively referred to as a "surface-treating composition") on the surface of the base material. This article can be produced, for example, as follows.

Firstly, the base material is provided. As mentioned above, the surface treatment agent of the present invention can be suitably applied to any base material as long as it has reactivity with a nitrileoxide group. The base material usable in the present invention may be composed of any suitable material such as a glass, a resin (may be a natural or synthetic resin such as a common plastic material, and may be in form of a plate, a film, or others), a metal (may be a simple substance of a metal such as aluminum, copper, or iron, or a complex such as alloy or the like), a ceramic, a semiconductor (silicon, germanium, or the like), a fiber (a fabric, a non-woven fabric, or the like), a fur, a leather, a wood, a pottery, a stone, or the like.

For example, when an article to be produced is an optical member, a material constituting the surface of the base material may be a material for an optical member, for example, a glass or a transparent plastic. For example, when an article to be produced is an optical member, any layer (or film) such as a hard coating layer or an antireflection layer may be formed on the surface (outermost layer) of the base material. As the antireflection layer, either a single antireflection layer or a multi antireflection layer may be used.

Examples of an inorganic material usable in the antireflection layer include $SiO_2$, $SiO$, $ZrO_2$, $TiO_2$, $TiO$, $Ti_2O_3$, $Ti_2O_5$, $Al_2O_3$, $Ta_2O_5$, $CeO_2$, $MgO$, $Y_2O_3$, $SnO_2$, $MgF_2$, $WO_3$, and the like. These inorganic materials may be used alone or in combination with two or more (for example, as a mixture). Furthermore, the base material may have an insulating layer, an adhesive layer, a protecting layer, a decorated frame layer (I—CON), an atomizing layer, a hard coating layer, a polarizing film, a phase difference film, a liquid crystal display module, and the like, depending on its specific specification.

The shape of the base material is not particularly limited. The region of the surface of the base material on which the surface-treating layer should be formed may be at least a part of the surface of the base material, and may be appropriately determined depending on use, the specific specification, and the like of the article to be produced.

The base material may be that of which at least the surface consists of a material originally having a group reactive with a nitrileoxide group. On the other hand, by pre-treating the base material, the group reactive with a nitrileoxide group may be introduced to the base material. For example, when the base material is a glass, the group reactive with a nitrileoxide group can be introduced to the base material by treating the base material with a piranha solution to express a hydroxyl group, and reacting this hydroxyl group for example with allyltrichlorosilane.

Next, the film of the above surface-treating agent of the present invention is formed on the surface of the base material, and the film is post-treated, as necessary, and thereby the surface-treating layer is formed from the surface-treating agent.

The formation of the film of the surface-treating agent of the present invention can be performed by applying the above surface-treating agent on the surface of the base material such that the surface-treating agent coats the surface. The method of coating is not particularly limited. For example, a wet coating method or a dry coating method can be used.

Examples of the wet coating method include dip coating, spin coating, flow coating, spray coating, roll coating, gravure coating, micro-gravure coating, bar coating, die coating, and a similar method.

Examples of the dry coating method include vacuum deposition, sputtering, CVD and a similar method. The specific examples of the vacuum deposition include resistance heating, electron beam, high-frequency heating, ion beam, and a similar method. The specific examples of the CVD method include plasma-CVD, optical CVD, thermal CVD and a similar method.

Additionally, coating can be performed by an atmospheric pressure plasma method.

When the wet coating method is used, the surface-treating agent of the present invention is diluted with a solvent, and then it is applied to the surface of the base material. In view of stability of the fluorine-containing compound or the composition and volatile property of the solvent, the following solvents are preferably used: an aliphatic perfluorohydrocarbon having 5-12 carbon atoms (for example, perfluorohexane, perfluoromethylcyclohexane and perfluoro-1, 3-dimethylcyclohexane); an aromatic polyfluorohydrocarbon (for example, bis(trifluoromethyl) benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF$ ($OCH_3$)$C_3F_7$) (the perfluoroalkyl group and the alkyl group may be liner or branched)), and the like. These solvents may be used alone or as a mixture of 2 or more compound. Among them, the hydrofluoroether is preferable, perfluorobutyl methyl ether ($C_4F_9OCH_3$) and/or perfluorobutyl ethyl ether ($C_4F_9OC_2H_5$) are particularly preferable.

After forming the film of the surface treatment agent by using the above method, if necessary, post-treatment may be performed. Examples of the post-treatment include, but are not particularly limited to, for example heating to 40-150° C., for example 60-100° C.

As described above, the surface-treating layer derived from the film of the surface-treating agent of the present invention is formed on the surface of the base material to produce the article of the present invention.

Therefore, the surface treatment agent can be suitably used to form the surface-treating layer on an outermost layer of an optical material. Examples of the optical material include preferably a variety of optical materials: for example, displays such as a cathode ray tube (CRT; for example, TV, personal computer monitor), a liquid crystal display, a plasma display, an organic EL display, an inorganic thin-film EL dot matrix display, a rear projection display, a vacuum fluorescent display (VFD), a field emission display (FED; Field Emission Display), or a protective plate of such displays, or that in which these displays and protective plates have been subjected to antireflection treatment on their surface.

The article having the surface-treating layer obtained according to the present invention is not specifically limited to, but may be an optical member. Examples of the optical member include the followings: lens of glasses, or the like; a front surface protective plate, an antireflection plate, a polarizing plate, or an anti-glare plate on a display such as PDP and LCD; a touch panel sheet of an instrument such as a mobile phone or a personal digital assistance; a disk surface of an optical disk such as a Blu-ray disk, a DVD disk, a CD-R or MO; an optical fiber, and the like.

The thickness of the surface-treating layer is not specifically limited. For the optical member, the thickness of the surface-treating layer is within the range of 0.1-30 μm, preferably 0.5-20 μm, in view of optical performance, friction durability and antifouling property.

The surface-treating layer formed from the surface treatment agent of the present invention may have water-repellency, oil-repellency, antifouling property, surface slip property, water-proof property and/or high friction durability, thus may be suitably used as a functional thin film.

In one embodiment, the composition of the present invention is a modifying agent.

The modifying agent of the present invention comprises at least one polymer having a group of the formula (Ib) at the terminal of the main chain of the present invention described above and can modify solubility in an organic solvent of a base material, for example, a polymer material.

Thought, the modifying agent of the present invention can exhibit a function even when it contains only the polymer having a group of the formula (Ib) at the terminal of the main chain of the present invention, the modifying agent may further contain a solvent.

Examples of the solvents described above are not particularly limited as long as it can dissolve the polymer having a group of the formula (Ib) at the terminal of the main chain of the present invention or can be compatible with the polymer having a group of the formula (Ib) at the terminal of the main chain of the present invention, and include, for example, a fluorine-containing aliphatic or aromatic hydrocarbons, and the like, in particular, perfluorohexane, bis(trifluoromethyl)benzene, and the like.

The modifying agent of the present invention can be suitably applied to any base material (for example, polymer material) as long as it has reactivity with a nitrileoxide group.

Examples of the polymer materials include, but are not particularly limited to, PAN (polyacrylonitrile) having a nitrile group (CN) in the molecular, NR (natural rubber) having a carbon-carbon double bond (C=C) in the molecular, EPDM (ethylene-propylene-diene copolymer rubber), polynorbornene, NBR (nitrile rubber) having a nitrile group and a carbon-carbon double bond in the molecular, and the like.

Modifying treatment using the modifying agent of the present invention can be carried out by contacting the polymer having a group of the formula (Ib) at the terminal of the main chain of the present invention with a polymer material in an organic solvent or without a solvent, although the present invention is not particularly limited thereto.

The solvents described above are, but not particularly limited to, preferably a solvent in which both the polymer material and the polymer having a group of the formula (Ib) at the terminal of the main chain of the present invention are easily dissolved. Specifically, it includes chloroform, DMF (N,N-dimethylformamide), and the like.

When the treatment is carried out in the absence of a solvent, the treatment may be carried out under air or an atmosphere where inert gas is filled.

Examples of the inert gases include, but are not particularly limited to, argon, nitrogen, and the like.

When the modifying treatment is carried out in the absence of a solvent, the modifying treatment is preferably carried out in a kneader.

Examples of the kneader include, but are not particularly limited to, kneaders such as a biaxial kneader, an internal mixer, and a Banbury mixer, or extruders such as a twin-screw extruder, a single screw extruder and a multi-screw extruder, and the like.

A temperature of the modifying treatment is not particularly limited as long as the polymer having a group of the formula (Ib) at the terminal of the main chain of the present invention can be reacted with the polymer material at the temperature, is preferably 0-150° C. since the chemical reaction is facilitated at higher temperature, on the other hand, a management of the manufacturing process is easy if a temperature control such as heating is not performed. Furthermore, the temperature is more preferably 20-100° C. when the polymer material is a polymer which has at least carbon-carbon double bond as a multiple bond, for example, NBR, NR, EPDM, or the like, and the temperature is more preferably 60-150° C. when the polymer material is a polymer which has only carbon-carbon triple bond as a multiple bond, for example, PAN or the like.

Additionally, the present invention provides a modified material, for example a modified polymer material, treated with the modifying agent described above.

In the modified polymer material treated with the modifying agent of the present invention, its solubility in various organic solvent is varied, and its resistance to sunlight and ozone is improved, as a result of which its durability is improved.

In one embodiment, the composition of the present invention is a filler modifier.

The filler modifier of the present invention comprises at least one polymer having a group of the formula (Ib) at the terminal of the main chain of the present invention.

Examples of the filler to which the filler modifier of the present invention is applied include a filler having a group reactive with a nitrileoxide group on its surface, for example, but are not particularly limited to, silica particles, alumina, titanium oxide, barium oxide and calcium oxide in which a group having an unsaturated bond such as a vinyl group, an allyl group, and a nitrile group is introduced on its surface.

The method for introducing the group having an unsaturated bond such as a vinyl group, an allyl group, and a nitrile group to the surface of silica particles is well known by those skilled in the art. For example, introduction of a vinyl group to the surface of the silica particles can be carried out by treating the silica particles with a vinyl-based silane coupling agent (e.g. vinylethoxysilane, or the like).

The modification treatment using the filler modifier can be carried out simply by mixing the filler modifier with the filler. The modification treatment is carried out in a solvent.

Examples of the solvent are not particularly limited as long as it is inert to the compound of the present invention and the filler, and include, for example, water, an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), methyl ether ($C_2F_5CF(OCH_2)C_2F_7$) (the perfluoroalkyl group and the alkyl group may be liner or branched)), and the like.

The present invention also provides a filler which is treated with the filler modifier, for example silica particles.

The filler which is treated with the filler modifier has effects, for example when it is used as a filler for a fluorine rubber, a perfluoro rubber or a fluororesin, dispersibility is improved or a reaction of a reactive group on the surface of the filler (for example, $SiO_2$ in silica) with a fluorine-containing polymer can be suppressed in comparison with an untreated filler.

In one embodiment, the composition of the present invention is a reactive compatibilizing agent.

The reactive compatibilizing agent of the present invention comprises any of at least one polymer having a monomer unit of the formula (Ia), at least one polymer having a monomer unit of the formula (IIa), at least one polymer having a group of the formula (Ib) at the terminal, of the present invention, and can improve compatibility between two or more materials (compounds). For example, the reactive compatibilizing agent of the present invention can improve compatibility (i) between a (non-fluorine-containing) general-purpose polymer reactive with a nitrileoxide group and a fluorine-containing polymer or (ii) between a general-purpose polymer and a fluorine-containing polymer reactive with a nitrileoxide group.

Since it is possible to introduce various groups into the polymer of the present invention depending to a compound to be compatibilized, the reactive compatibilizing agent of the present invention is able to compatibilize various compounds. For example, for compatibilizing (i) between a (non-fluorine-containing) general-purpose polymer reactive with a nitrileoxide group and a fluorine-containing polymer, the reactive compatibilizing agent of the present invention is able to be suitably used in any combinations as long as these are a combination of a compound which has a fluorine-containing group and is reactive with a nitrileoxide group and a fluorine-containing compound. For compatibilizing (ii) between a fluorine-containing polymer reactive with a nitrileoxide group and a general-purpose polymer, the reactive compatibilizing agent of the present invention is able to be suitably used in any combinations as long as these are a combination of a fluorine-containing polymer which has a non-fluorine-containing group and is reactive with a nitrileoxide group and a general-purpose polymer. In addition, a combination of compounds to be compatibilized (be complexed) may be a combination of three or more compounds, for example, one compound reactive with a nitrileoxide group and two fluorine-containing compounds.

The compound having reactivity with the nitrileoxide group is not limited as long as the compound is a polymer having a moiety reactive with the nitrileoxide group (preferably, C=C, C≡N) in the molecule described above. The moiety reactive with the nitrileoxide group may be in the backbone itself of the polymer described below, or when the moiety is absent, a substituent having moiety reactive with the nitrileoxide group may be introduced into the polymer.

Examples of the general-purpose polymers include, for example, polymers containing an aromatic ring in the main chain or the side chain (polystyrene, polyamide, polyimide, polycarbonate, polyphenylene ether, polyalkylene terephthalates, polysulfones, polyphenylene sulfide, polyaryl ether ketone, etc.), polypropylene, polyethylene etc., or natural rubber, NBR (nitrile rubber), EPDM (ethylene-propylene-diene copolymer rubber), PAN (polyacrylonitrile), polynorbornene, $H_2C=C(R)-(CH_2-CHR)_n-CH_2-CR=CH_2$ (wherein R is each independently a hydrogen atom, a methyl group, an ethyl group or an isobutyl group, and n is an integer from 10 to 1000), and the like.

Examples of the fluorine-containing compound include, but are not particularly limited to, a fluororesin, a fluorine rubber, and the like.

Examples of the fluororesin include a non-melt processable fluororesin, for example, polytetrafluoroethylene (PTFE), and a melt processable fluororesin, and the like.

The PTFE may be a homopolymer of tetrafluoroethylene (TFE), or a modified polytetrafluoroethylene (modified PTFE). In the present specification, "modified PTFE" means a polymer obtained by co-polymerizing TFE with a co-monomer in such a small amount as not to provide melt processability to the resulting copolymer. Examples of the small amount of co-monomer include, but are not limited to, for example, hexafluoropropylene (HFP), chlorotrifluoroethylene (CTFE), trifluoroethylene (TrFE), a perfluoro(alkyl vinyl ether) (PAVE), a perfluoro(alkoxyalkyl vinyl ether), a (perfluoroalkyl)ethylene, and the like. The small amount of co-monomer can be used alone or two or more.

Examples of the PAVE include perfluoro(methylvinyl ether), perfluoro(ethylvinyl ether), perfluoro(propylvinyl ether), and the like.

A ratio of the small amount of co-monomer added to the modified PTFE is, when PAVE, a perfluoro(alkoxyalkyl vinyl ether), or the like is used, usually 0.001-1% by mass with respect to the total mass of TFE and the small amount of copolymer, but it is difficult depending on the type.

Examples of the melt processable fluororesin include a tetrafluoroethylene (TFE)/hexafluoropropylene (HFP) copolymer, a TFE/HFP/perfluoro(alkyl vinyl ether) (PAVE) copolymer, a TFE/PAVE copolymer (tetrafluoroethylene-perfluoroalkyl vinyl ether copolymer (PFA) and a tetrafluoroethylene-perfluoro methyl vinyl ether copolymer (MFA)), an ethylene (Et)/TFE copolymer, an Et/TFE/HFP copolymer, polychlorotrifluoroethylene (PCTFE), a chlorotrifluoroethylene (CTFE)/TFE copolymer, an Et/CTFE copolymer, a TFE/vinylidene fluoride (VDF) copolymer, a VDF/HFP/TFE copolymer, a VDF/HFP copolymer, and the like.

Examples of the fluororesin further include a hydroxyl group containing and fluorine containing copolymer containing a fluoroolefin unit and a hydroxyl group-containing radical polymerizable unsaturated monomer unit.

Examples of the fluoroolefin unit include one or more of a tetrafluoroethylene (TFE) unit, a chlorotrifluoroethylene (CTFE) unit, a vinyl fluoride (VF) unit, a vinylidene fluoride (VDF) unit, a hexafluoropropylene (HFP) unit, a trifluoroethylene (TrFE) unit, a perfluoro(alkyl vinyl ether) (PAVE) unit. Examples of the PAVE unit include a perfluoromethyl vinyl ether unit and a perfluoropropylvinyl ether unit.

Examples of the combination of two or more units comprising the TFE unit include a TFE/HFP unit, a TFE/PAVE unit, a TFE/ethylene unit, a TFE/vinyl ether unit, a TFE/vinyl ester unit, a TFE/vinyl ester/vinyl ether unit, a TFE/vinyl ether/allyl ether unit, and the like. Among them, in view of readily mixing with an ethylenically unsaturated group-containing monomer, the TFE/ethylene unit, the TFE/vinyl ether unit, the TFE/vinyl ester unit, the TFE/vinyl ester/vinyl ether unit, the TFE/vinyl ether/allyl ether unit, or the like is preferable.

Examples of the combination of two or more units comprising the CTFE unit include a CTFE/HFP unit, a CTFE/PAVE unit, a CTFE/ethylene unit, a CTFE/vinyl ether unit, a CTFE/vinyl ester unit, a CTFE/vinyl ester/vinyl ether unit, a CTFE/vinyl ether/allyl ether unit, and the like. Among them, in view of readily mixing with an ethylenically unsaturated group-containing monomer, the CTFE/ethylene unit, the CTFE/vinyl ether unit, the CTFE/vinyl ester unit, the CTFE/vinyl ester/vinyl ether unit, the CTFE/vinyl ether/allyl ether unit, or the like is preferable.

Examples of the combination of two or more units comprising the HFP unit include a CTFE/HFP unit, a TFE/HFP unit, a HFP/vinyl ether unit, a HFP/vinyl ester unit, a HFP/vinyl ester/vinyl ether unit, a HFP/vinyl ether/allyl ether unit, and the like. Among them, in view of readily mixing with an ethylenically unsaturated group-containing monomer, the HFP/vinyl ether unit, the HFP/vinyl ester unit, the HFP/vinyl ester/vinyl ether unit, the HFP/vinyl ether/allyl ether unit, or the like is preferable.

Examples of the combination of two or more units comprising the VDF unit include a VDF/TFE unit, a VDF/HFP unit, a VDF/TFE/HFP unit, a VDF/CTFE unit, a VDF/TFE/PAVE unit, a VDF/CTFE/TFE unit, a VDF/CTFE/HFP unit, and the like. Among them, in view of readily mixing with an ethylenically unsaturated group-containing monomer, it is preferable that the VDF unit is contained in the polymer at 50 mol % or more.

Specific examples of the hydroxyl group-containing radical polymerizable unsaturated monomer unit of the hydroxyl group containing and fluorine containing copolymer include, for example, a hydroxyalkyl vinyl ether or a hydroxyalkyl allyl ether of the formula:

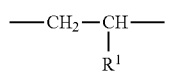

wherein $R^1$ is $-OR^2$ or $-CH_2OR^2$ (wherein $R^2$ is an alkyl group having a hydroxyl group). $R^2$ is, for example, a group which 1-3 hydroxyl groups, preferably one hydroxyl group is linked to a straight or branched alkyl group having 1-8 carbon atoms. Examples of them include, for example, a 2-hydroxyethylvinyl ether unit, a 3-hydroxypropylvinyl ether unit, a 2-hydroxypropylvinyl ether unit, a 2-hydroxy-2-methylpropylvinyl ether unit, a 4-hydroxybutylvinyl ether unit, a 4-hydroxy-2-methylbutylvinyl ether unit, a 5-hydroxypentylvinyl ether unit, 6-hydroxyhexylvinyl ether unit, a 2-hydroxyethylallyl ether unit, a 4-hydroxybutylallyl ether unit, an ethylene glycol monoallyl ether unit, a diethylene glycol monoallyl ether unit, a triethylene glycol monoallyl ether unit, a glycerin monoallyl ether unit, and the like. Among them, a hydroxyalkyl vinyl ether having 1-3 carbon atoms is particularly preferable, and a 4-hydroxybutylvinyl ether unit or a 2-hydroxyethylvinyl ether unit is more preferable in view of easy polymerization.

The hydroxyl group containing and fluorine containing copolymer may further comprise a hydroxyl-free and fluorine-free vinyl ether unit and/or a fluorine-free vinyl ester unit Specific examples of the hydroxyl group-free and fluorine-free vinyl ether unit and/or the fluorine-free vinyl ester unit in the hydroxyl group containing and fluorine containing copolymer include, for example, an alkyl vinyl ether or an alkyl allyl ether of the formula:

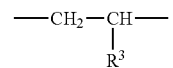

wherein $R^3$ is $-OR^4$, $-COOR^4$ or $-OCOR^4$ (wherein $R^4$ is an alkyl group). $R^4$ is, for example, a straight, branched or cyclic alkyl group having 1-8 carbon atoms. As examples of them, for example, a cyclohexylvinyl ether unit, a methylvinyl ether unit, an ethylvinyl ether unit, a propylvinyl ether unit, an n-butylvinyl ether unit, an isobutylvinyl ether unit, a vinyl acetate unit, a vinyl propionate unit, a vinyl butyrate unit, a vinyl isobutyrate unit, a vinyl pivalate unit, a vinyl caproate unit, a vinyl versatate unit, a vinyl laurate unit, a vinyl stearate unit or a vinyl cyclohexyl carboxylate unit is preferable. Furthermore, in view of excellent weather resistance, solubility and low-cost, vinyl versatate, vinyl laurate, vinyl stearate, a vinyl cyclohexyl carboxylate, or vinyl acetate is preferable. Among them, in view of chemical resistance, a non-aromatic vinyl carboxylate ester, in particular a carboxylic acid vinyl ester having 6 or more carbon atoms in carboxylic acid is preferable, and a carboxylic acid vinyl ester having 9 or more carbon atoms in carboxylic acid is more preferable. The upper limit of carbon atoms of carboxylic acid in the carboxylic acid vinyl ester is preferably 20 or less, more preferably 15 or more. As a specific example, vinyl versatate is most preferably.

The hydroxyl group containing and fluorine containing copolymer may contain a carboxyl group-containing monomer unit.

The carboxyl group-containing monomer unit contains a carboxyl group and does not contain a hydroxyl group and an aromatic group, and in this point, it differs from the other units.

Examples of the carboxyl group-containing monomer unit include, for example, a carboxyl group-containing vinyl monomer of the formula:

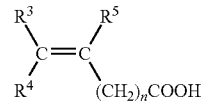

wherein $R^3$, $R^4$ and $R^5$ is same or different, and are a hydrogen atom, an alkyl group, a carboxyl group or an ester group, and n is 0 or 1 or the formula:

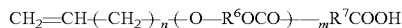

wherein $R^6$ and $R^7$ are same or different, and are a saturated or unsaturated straight or cyclic alkyl group, n is 0 or 1, and m is 0 or 1.

Specific examples of the carboxyl group-containing monomer unit include, for example, one or more selected from acrylic acid, methacrylic acid, vinyl acetate, crotonic acid, cinnamic acid, 3-allyloxy propionic acid, itaconic acid, itaconic acid monoester, maleic acid, maleic acid monoester, maleic anhydride, fumaric acid, fumaric acid monoester, vinyl phthalate and vinyl pyromellitate. Among them, crotonic acid, itaconic acid, maleic acid, maleic acid monoester, fumaric acid, fumaric acid monoester, and 3-allyloxy propionic acid which have low homopolymerizality are preferable.

The lower limit of the ratio of carboxyl group-containing monomer unit is 0.1 mol %, preferably 0.4 mol %, and the upper limit is 2.0 mol %, preferably 1.5 mol %.

Specific examples of the hydroxyl group containing and fluorine containing copolymer include, for example, following compounds:

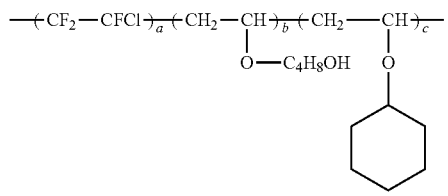

(wherein the formula, the ratio by mole of a, b, and c is a:b:c=40 to 60:3 to 15:5 to 45);

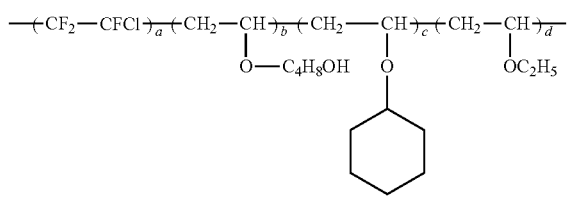

(wherein the formula, the ratio by mole of a, b, and c is a:b:c=40 to 60:3 to 15:5 to 45:5 to 45);

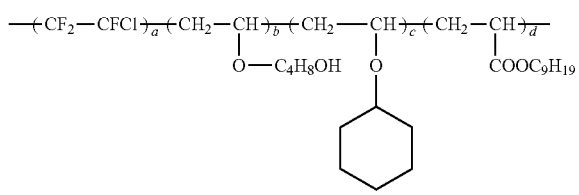

(wherein the formula, the ratio by mole of a, b, c and d is a:b:c:d=40 to 60:3 to 15:5 to 45:5 to 45);

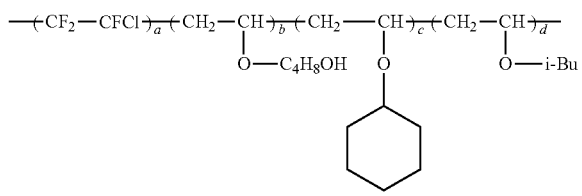

(wherein the formula, the ratio by mole of a, b, c and d is a:b:c:d=40 to 60:3 to 15:5 to 45:5 to 45, and i-Bu represents an isobutyl group);

tetrafluoroethylene/vinyl versatate/hydroxybutyl vinyl ether; tetrafluoroethylene/vinyl versatate/hydroxyethyl vinyl ether/tert-butyl vinyl benzoate; tetrafluoroethylene/vinyl versatate/hydroxybutyl vinyl ether/crotonic acid; and tetrafluoroethylene/vinyl versatate/hydroxyethyl vinyl ether/vinyl benzoate/crotonic acid.

Examples of the fluorine rubber include a non-perfluoro fluorine rubber and a perfluoro fluorine rubber.

Examples of the non-perfluoro fluorine rubber include a vinylidene fluoride (VDF) fluorine rubber, tetrafluoroethylene (TFE)/propylene (Pr) fluorine rubber, tetrafluoroethylene (TFE)/propylene/vinylidene fluoride (VDF) fluorine rubber, ethylene/hexafluoropropylene (HFP) fluorine rubber, ethylene/hexafluoropropylene (HFP)/vinylidene fluoride (VdF) fluorine rubber, ethylene/hexafluoropropylene (HFP)/tetrafluoroethylene (TFE) fluorine rubber, fluorosilicone fluorine rubber and fluorophosphazene fluorine rubber. They can be used alone or can be used in arbitrary combinations, as long as the effects of the present invention are not lost. Among them, a vinylidene fluoride fluorine rubber and a tetrafluoroethylene/propylene fluorine rubber are preferable.

The vinylidene fluoride fluorine rubber means a fluorine-containing elastomeric copolymer comprising 45 to 85 mol % of vinylidene fluoride and 55 to 15 mol % of at least one other monomer copolymerizable with vinylidene fluoride. It is preferably referred to fluorine-containing copolymer comprising 50 to 80 mol % of vinylidene fluoride and 50 to 20 mol % of at least one monomer copolymerizable with vinylidene fluoride.

Examples of the at least one other monomer copolymerizable with vinylidene fluoride include, for example, fluorine-containing monomers such as tetrafluoroethylene (TFE), chlorotrifluoroethylene (CTFE), trifluoroethylene, hexafluoropropylene (HFP), trifluoropropylene, tetrafluoropropylene, pentafluoropropylene, trifluorobutene, tetrafluoroisobutene, perfluoro(alkyl vinyl ether) (PAVE), vinyl fluoride, and the like, and fluorine-free monomers such as ethylene, propylene, and alkyl vinyl ether. They can be used alone or in arbitrarily combinations. Among them, tetrafluoroethylene, hexafluoropropylene, and perfluoro (alkyl vinyl ether) are preferable.

In this case, examples of the perfluoro(alkyl vinyl ether) include, for example, perfluoro(methylvinyl ether), perfluoro(propylvinyl ether), and the like. They can be used alone or in arbitrary combinations, as long as the effects of the present invention are not lost.

Examples of the vinylidene fluoride fluorine rubber include a VDF-HFP rubber, a VDF-HFP-TFE rubber, a VDF-CTFE rubber, a VDF-CTFE-TFE rubber, and the like.

The tetrafluoroethylene/propylene fluorine rubber means a fluorine-containing elastomer copolymer comprising 45 to 70 mol % of tetrafluoroethylene, 55 to 30 mol % of propylene, and 0 to 5 mol % of a monomer providing a cross-linking site.

Examples of the monomer providing a cross-linking site include, for example, iodine-containing monomers such as perfluoro(6,6-dihydro-6-iodo-3-oxa-1-hexene) and perfluoro(5-iodo-3-oxa-1-pentene) described in JP 05-63482 B and JP 07-316234 A, bromine-containing monomers described in JP 04-505341 A, cyano group-containing monomers, carboxyl group-containing monomers and alkoxycarbonyl group-containing monomers described in JP 04-505345 A and JP 05-500070 A.

Examples of the perfluoro fluorine rubber include a perfluoro rubber containing TFE, for example, a fluorine-containing elastomer copolymer consisting of TFE/perfluoro(alkyl vinyl ether) (PAVE)/a monomer providing a cross-linking site. The composition is preferably 45 to 90/10 to 50/0 to 5 (mol %), more preferably, 45 to 80/20 to 50/0 to 5, further preferably, 53 to 70/30 to 45/0 to 2. If the composition is out of this range, property as a rubber elastomer is tend to be lost and become property close to a resin property.

In this case, examples of the PAVE include, for example, perfluoro(methylvinyl ether) (PMVE), perfluoro(propylvinyl ether) (PPVE), and the like. They can be used alone or in arbitrary combinations, as long as the effects of the present invention are not lost.

Examples of the monomer providing a cross-linking site include, for example, an iodine-containing monomer of the following formula:

$$CX_2=CX-R_fCHRI$$

wherein X is H, F or $CH_3$, $R_f$ is a fluoroalkylene group, a perfluoroalkylene group, a fluoropolyoxyalkylene group or a perfluoropolyoxyalkylene group, and R is H or $CH_3$, and a monomer of the following formula:

$$CF_2=CFO(CF_2CF(CF_3))_m-O-(CF_2)_n-Y$$

wherein m is an integer of 0-5, n is an integer of 1-3, Y is a nitrile group, a carboxyl group, an alkoxycarbonyl group or a bromine atom). They can be used alone or in arbitrary combinations, as long as the effects of the present invention are not lost. The iodine atom, the nitrile group, the carboxyl group, the alkoxycarbonyl group, and the bromine atom function as the cross-linking site.

Specific examples of the perfluoro fluorine rubber include a fluorine rubber and the like described in WO 97/24381, JP 61-57324 B, JP 04-81608 B, and JP 05-13961 B.

Examples of the other fluorine-containing polymer include homopolymer such as PVDF (polyvinylidene fluoride), PVF (polyvinyl fluoride).

The reactive compatibilizing agent of the present invention can exert its function simply by mixing the reactive compatibilizing agent containing the compound of the present invention with the compound reactive with a nitrileoxide group and the fluorine containing compound in a step of mixing the compound reactive with a nitrileoxide group and the fluorine containing compound under an atmosphere pressure in a mixing equipment (a kneader, a brabender, an extruder, etc.). In this mixing step, the compound of the present invention click-reacts with a reactive site of the compound reactive with a nitrileoxide group, thereby a fluorine-containing group can be introduced to the compound reactive with a nitrileoxide group. This introduced fluorine-containing group has an affinity for the fluorine-containing compound, thereby enabling compatibilization (complexation) of the both compounds.

The above mixing step is usually carried out at a temperature at which the compound reactive with a nitrileoxide group and the fluorine-containing compound melts, for example, about 150-250° C. For example, when NBR as the compound reactive with a nitrileoxide group is used, and PVDF as the fluorine-containing compound is used, the step is carried out at about 170° C. or more, for example, about 180-210° C. Since the compound of the present invention has a high thermal stability, such treatment at the high temperature can be carried out.

The above mixing step can be carried out usually without a solvent, additives, etc. However, the solvent or additives may be added depending on a purpose, for example in order to accelerate the reaction. Those skilled in the art can select the solvent and the additives depending on a purpose.

Examples of a conventional general compatibilizing agent are a block polymer and a graft polymer which have both backbones of two components to be complexed. The compound of the present invention is advantageous in that the preparation is easy in comparison with the conventional polymer. In addition, the reactive compatibilizing agent of the present invention has an advantage in that it can compatibilize components to be compatibilized simply by mixing the reactive compatibilizing agent with the mixture of the components.

In addition, the present invention provides a composite of two or more compounds treated with the reactive compatibilizing agent of the present invention.

In one embodiment, the composition of the present invention is a fiber treatment agent.

The fiber treatment agent of the present invention contains any of at least one polymer having a monomer unit of the formula (Ia), at least one polymer having a monomer unit of the formula (IIa), at least one polymer having a group of the formula (Ib) at the terminal, of the present invention, and can improve water-repellency and oil-repellency of a fiber having a group reactive with a nitrileoxide group, for example, an acrylate fiber.

The fiber treatment agent of the present invention can be suitably used for any fiber as long as it has the group reactive with a nitrileoxide group.

Examples of the fiber include an acrylate fiber, or a polyester fiber or a polyvinyl alcohol fiber obtained by copolymerizing a monomer having a nitrile group in its side chain. In addition, even a fiber having no group reactive with a nitrileoxide group become to be able to be treated with the fiber treatment agent of the present invention by introducing the group reactive with a nitrileoxide group thereto. For example, a polyester fiber or a polyvinyl alcohol fiber obtained by copolymerizing a monomer having a hydroxyl group or an amino group in its side chain become to be able to be treated with the fiber treatment agent of the present invention by dehydration-condensation with a carbonic acid or sulfonic acid compound reactive with a nitrileoxide group.

The fiber treatment agent of the present invention may contain, additives, for example, an emulsifying agent (polyethylene glycol-based, cationic, ammonium, nonionic, anionic), an antifoaming agent, a wetting agent, a paraffin hydrocarbon, and the like in addition to any of at least one polymer having a monomer unit of the formula (Ia), at least one polymer having a monomer unit of the formula (IIa), at least one polymer having a group of the formula (Ib) at the terminal of the present invention.

The fiber treatment agent of the present invention may be diluted with a solvent before being applied to the fiber. Examples of the solvent include, for example, an aliphatic perfluorohydrocarbon having 5-12 carbon atoms (for example, perfluorohexane, perfluoromethylcyclohexane and perfluoro-1,3-dimethylcyclohexane); an aromatic polyfluorohydrocarbon (for example, bis(trifluoromethyl)benzene); an aliphatic polyfluorohydrocarbon; a hydrofluoroether (HFE) (for example, an alkyl perfluoroalkyl ether such as perfluoropropyl methyl ether ($C_3F_7OCH_3$), perfluorobutyl methyl ether ($C_4F_9OCH_3$), perfluorobutyl ethyl ether ($C_4F_9OC_2H_5$), and perfluorohexyl methyl ether ($C_2F_5CF(OCH_3)C_3F_7$) (the perfluoroalkyl group and the alkyl group may be liner or branched)), other fluorine solvents, hydrocarbon solvents such as a mineral oil, alcohol, MIBK (methyl isobutyl ketone), glycol-based solvents (ethylene glycol, propylene glycol etc.), and the like.

A method for applying the fiber treatment agent of the present invention to the fiber is not particularly limited as long as it can attach the desired amount of the agent of the fiber to be treated, and various methods can be used. the fiber treatment method includes, be a continuous method or a batch method.

As the continuous method, first, the fiber treatment agent is diluted with a solvent to prepare a treating liquid. Then, an object to be treated is continuously supplied to an impregnation apparatus filled with the treating liquid to impregnate the object to be treated with the treating liquid, and then unnecessary treating liquid is removed. The impregnation apparatus is not particularly limited, and is preferably a padder impregnation apparatus, a kiss roller impregnation apparatus, a gravure coater impregnation apparatus, a spray impregnation apparatus, a foam impregnation apparatus, a coating impregnation apparatus or the like, particularly preferably a padder impregnation apparatus. Then, an operation of removing the solvent remaining in the object is carried out by using a dryer. The dryer is not particularly limited, and is preferably an expansion dryer such as a tenter or a hot flue. This continuous method is employed preferably in a case where the object to be treated is cloth such as woven cloth.

The batch method comprises a step of immersing the object to be treated with a treating liquid, and a step of removing the solvent remaining in the treated object. The batch method is employed preferably in a case where the object to be treated is not cloth, such as a case where it is bulk fiber, top, sliver, hank, tow or thread, or in a case where it is not suitable for the continuous method such as a case where it is knitted fabric. In the immersion step, it is preferred to use, for example, a cotton dyeing machine, a cheese dyeing machine, a jet dyeing machine, an industrial washing machine or a beam dyeing machine. In operation of removing the solvent, it is preferred to use a hot air dryer such as a cheese dryer, a beam dryer or a tumble dryer, or a microwave dryer The treated object to which the fiber treatment agent of the present invention is attached is preferably subjected to a dry heat treatment. When the dry heat treatment is carried out, active ingredients in the fiber treatment agent of the present invention will more firmly attach to the object to be treated. The temperature for the dry heat treatment is preferably from 120 to 180° C., more preferably from 160 to 180° C. The dry heat treatment time is preferably from 10 seconds to 3 minutes, more preferably from 1 to 2 minutes. The method of the dry heat treatment is not particularly limited, and it is preferred to use a tenter in a case where the object to be treated is cloth.

In addition, the present invention provides a fiber treated with the fiber treatment agent.

The fiber treated with the fiber treatment agent of the present invention has improved water and oil repellency, weather resistance and/or thermal resistance, or the like depending on the compound of the present invention used. In addition, since the compound of the present invention is chemically bonded to the fiber by click-reaction, the above functions are less likely to deteriorate by friction, etc., and can maintain the function for a long time.

In one embodiment, the composition of the present invention is a cross-linking agent.

The cross-linking agent of the present invention contains at least one any of at least one polymer of the formula (Ia), at least one polymer having a monomer unit of the formula (IIa), at least one polymer having a group of the formula (Ib) at the terminal, or the present invention, and can react with two functional groups reactive with a nitrileoxide group and cross-link between these functional groups. It is noted that the two functional groups may be present in same molecular or in different molecular, respectively.

Since any of at least one nitrileoxide polymer of the formula (Ia), at least one polymer having a monomer unit of the formula (IIa), at least one polymer having a group of the formula (Ib) at the terminal of the present invention has higher thermal resistance in comparison with the conventional aromatic multifunctional nitrileoxide, it can be used under a high temperature condition. Therefore, even when a compound to be cross-linked is a polymer having a small amount of reaction sites (that is, unsaturated sites) or a polymer whose back bone is rigid and has poor molecular mobility, these compounds can be cross-linked by subjecting these compounds a treatment under the high temperature condition. Specifically, even a polymer containing tetrafluoroethylene such as a base polymer of the fluorine rubber, a base polymer of the perfluoro rubber, or the like as a main ingredient can be suitably cross-linked.

The compound to be cross-linked is not particularly limited as long as it has a moiety reactive with a nitrileoxide group, and may be, for example, a polymer having a moiety reactive with a nitrileoxide group, for example, a general-purpose rubber, a natural rubber, polynorbornene, a fluoropolymer (preferably, that obtained by polymerizing fluoroolefins or fluorine-containing (metha)acrylates, particularly preferably, a fluorine rubber).

Examples of the general-purpose rubber include, for example, NBR (nitrile rubber), EPDM (ethylene-propylene-diene copolymer rubber), PAN (polyacrylonitrile), $H_2C=C(R)-(CH_2-CHR)_n-CH_2-CR=CH_2$ (wherein R is each independently a hydrogen atom, a methyl group, an ethyl group, or an isobutyl group, and n is an integer of 10-1000).

The natural rubber is a rubbery polymer naturally occurring in normal, and usually has a polyisoprene structure, although is not limited thereto.

The fluorine-containing (meth) acrylates are a compound of $H_2C=C(X)-CO-O-Y$, wherein X is a hydrogen atom, a methyl group, an ethyl group, a trifluoromethyl group, a fluorine atom, or a chlorine atom, and Y is a linear or branched alkyl group having at least one a fluoro group, preferably an alkyl group comprising a skeleton of a perfluoroalkylene group or a perfluoroalkyl group, particularly preferably, $-CH_2(CF_2)_nH$, $-CH_2CH_2(CF_2)_nF$.

The fluorine rubber may be either a non-perfluoro fluorine rubber or a perfluoro fluorine rubber, for example, and preferably has a structural unit derived from at least one monomer selected from the group consisting of tetrafluoroethylene (TFE), vinylidene fluoride (VdF) and a perfluoroethylenically unsaturated compound (for example, hexafluoropropylene (HFP), perfluoro(alkyl vinyl ether) (PAVE), and the like) of the following formula (a):

$$CF_2=CF-Rf^a \quad (a)$$

wherein $Rf^a$ represents $-CF_3$ or $ORf^b$ wherein $Rf^b$ represents a perfluoroalkyl group having 1-5 carbon atoms.

Examples of the non-perfluoro fluorine rubber include a vinylidene fluoride (VdF) fluorine rubber, tetrafluoroethylene (TFE)/propylene (Pr) fluorine rubber, tetrafluoroethylene (TFE)/propylene (Pr)/vinylidene fluoride (VdF) fluorine rubber, ethylene (Et)/hexafluoropropylene (HFP) fluorine rubber, ethylene (Et)/hexafluoropropylene (HFP)/vinylidene fluoride (VdF) fluorine rubber, ethylene (Et)/hexafluoropropylene (HFP)/tetrafluoroethylene (TFE) fluorine rubber, fluorosilicone fluorine rubber and fluorophosphazene fluorine rubber. They can be used alone or in combinations. In addition, these fluorine rubbers may be a copolymer with co-monomer.

The co-monomer is not particularly limited as long as it can copolymerize with other monomer, and include, for example, TFE, HFP, PAVE, chlorotrifluoroethylene (CTFE), trifluoroethylene, trifluoropropylene, tetrafluoropropylene, pentafluoropropylene, trifluorobutene, tetrafluoroisobutene, hexafluoroisobutene, vinyl fluoride, an iodine-containing and fluorine-containing vinyl ether, perfluorovinyl ether such as a fluorine-containing monomer of the formula (b):

$$CH_2=CFRf^b \quad (b)$$

wherein $Rf^b$ is a straight or branched fluoroalkyl group having 1-12 carbon atoms;
a fluorine-containing monomer (c);

$$CF_2=CFOCF_2ORf^c \quad (c)$$

wherein $Rf^c$ is a straight or branched perfluoroalkyl group having 1-6 carbon atoms, a cyclic perfluoroalkyl group having 5-6 carbon atoms or a straight or branched perfluorooxyalkyl group having 1-3 oxygen atoms and 2-6 carbon atoms; a fluorine-free monomer such as ethylene (Et), propylene (Pr), alkyl vinyl ether; and, a reactive emulsifier. They can be used alone or in combination with two or more.

Examples of the copolymer include, but are not particularly limited to, for example, at least one copolymer selected from the group consisting of a VdF/HFP copolymer, a VdF/TFE/HFP copolymer, a VdF/CTFE copolymer, a VdF/CTFE/TFE copolymer, a VdF/PAVE copolymer, a VdF/TFE/PAVE copolymer, a VdF/HFP/PAVE copolymer, a VdF/HFP/TFE/PAVE copolymer, a VdF/TFE/propylene(Pr) copolymer, a VdF/ethylene(Et)/HFP copolymer and a copolymer of VdF/the fluorine-containing monomer (b) of the formula (b).

The reactive site with a nitrileoxide group in the fluorine rubber may be derived from a monomer having the reactive site or may be introduced by modifying a fluorine rubber having no reactive site.

Examples of the monomer having a reactive site with a nitrileoxide group include, for example, a bisolefin compound of the formula:

$$R^{22}R^{23}C=CR^{24}-Z-CR^{25}=CR^{26}R^{27}$$

wherein $R^{22}$, $R^{23}$, $R^{24}$, $R^{25}$, $R^{26}$ and $R^{27}$ are same or difference, and are independently represent a hydrogen atom or an alkyl group having 1-5 carbon atoms; and
Z represents a straight or branched alkylene or an cycloalkylene group having 1-18 carbon atoms which may have an oxygen atom and preferably fluorinated at least partially, or a (per) fluoropolyoxyalkylene group.

Other examples of the monomer having a reactive site with a nitrileoxide group include an olefin compound having a nitrile group, for example, a compound of the formula:

$$R^{28}R^{29}C=CR^{30}-Z-CN$$

wherein $R^{28}$, $R^{29}$ wherein and $R^{30}$ are same or different, and independently represent a hydrogen atom or an alkyl group having 1-5 carbon atoms; and
Z represents a straight or branched alkylene or an cycloalkylene group having 1-18 carbon atoms which may have an oxygen atom and preferably fluorinated at least partially or a (per) fluoropolyoxyalkylene group, representatively, $CF_2=CFOCF_2CF(CF_3)OCF_2CF_2CN$.

Another examples of the monomer having a reactive site with a nitrileoxide group include acrylonitrile, 5-ethylidene-2-norbornene, and a styrene derivative having a nitrile group on the aromatic ring.

In one embodiment, the composition of the present invention can also function as a filler.

The filler of the present invention comprise at least one polymers comprising one or more monomer units of the formula (Ia), and at least one polymers comprising a monomer unit of the formula (IIa) and a group of the formula (Ib) at the terminal. Since the filler contains a nitrileoxide group, the filler is filled while efficiently forming the bond with a material to be mixed.

The material to be mixed with the composition of the present invention is not limited as long as it is a polymer material, and examples of the material include, for example, a fluorine-containing polymer such as a fluorine resin, a fluorine rubber, or the like.

With respect to the function as a filler, the composition of the present invention may have a desired function by designing a structure of the composition depending on the purpose, and may have, for example, a function to provide the material to be mixed with properties such as mechanical strength, antimicrobial, gas barrier property, conductivity, flame retardancy, weather resistance, water absorption property, or the like. Although the present invention is not limited to the below, for example, when a crosslinkable filler having a polyamide type structure is used as the polymer of the formula (Ia), the mechanical strength of the material to be mixed can be enhanced. The crosslinkable filler acts also as a crosslinking agent, and since the crosslinkable filler can form a chemical bond with the material to be mixed, the crosslinkable filler provides the higher effect to increase than a usual filler which is not crosslinkable. As mentioned above, when the polyamide structure having high mechanical strength is used as a polymer of the formula (Ia), the polymer can provide a mechanical reinforcing effect, in addition, by using a polymer backbone having desired properties as the composition of the present invention, the desired properties can be provided to the material to be mixed. As noted above, the polymer represented by formula (Ia), in case of adopting the polyamide backbone having a high mechanical strength is mechanical reinforcing effect is obtained, the desired as a composition of the present invention by employing a polymer backbone having the characteristics, it is possible to impart desired properties to the kneading mating member.

The size of the filler is, but is not particularly limited to, usually about 100 nm to 10 nm.

The shape of the filler may be, but is not particularly limited to, for example, spherical, completely spherical, granular, fibrous, plate, or the like.

Examples of a method of mixing the composition of the present invention to the material includes, but are not particularly limited to, usually, the kneading by human power in a mortar, the kneading by using an apparatus such as a roll, a kneader, an extruder, and the kneading in the apparatus providing a supercritical condition environment.

When the composition is mixed with the material, if necessary, a pretreatment may be performed. The pretreatment provides, for example, the effect to facilitate dispersion of the particles, the effect of preventing aggregation, the effect of improving the workability, the effect to increase the wettability to the material to which the composition is added.

In one embodiment, the composition of the present invention is used as a raw material of a low-temperature property rubber.

The low-temperature property rubber can be produced by producing a fluorine rubber or a perfluororubber by the composition of the present invention.

The fluorine rubber and the perfluororubber are not limited as long as having the reactivity with the nitrileoxide group, and include, for example, the non-perfluoro fluorine rubber and the perfluoro fluorine rubber described above.

In the production of the low-temperature property rubber, the composition of the present invention is used as follows, although the present invention is not particularly limited thereto.

The compositions of the present invention is added and mixed at the same timing as adding and mixing of a crosslinking agent and/or a filler which is added as necessary in a kneading process (roll kneading, Banbury mixing, etc.) after preparing a base polymer of the fluorine-containing rubber by general polymerization. The base polymer in which the compound is sufficiently dispersed in this way is subjected to the press (first vulcanization), and oven heating (second vulcanization), as a result, clicks reaction of the compound of the present invention with unsaturated bonds in the fluorine-containing polymer occurs, thereby obtaining the low temperature properties rubber.

The above process is usually performed in the absence of a solvent. If necessary, for example, in order to improve the dispersibility of the compound of the present invention, a solvent may be used. The solvent is appropriately selected depending on the type of the raw material to be used and the low-temperature property rubber of interest, for example, the solvent includes a fluorine-containing solvent.

Since an untreated fluorine-containing rubber generally has a skeleton in which the molecular backbone is rigid, the untreated fluorine-containing rubber has insufficient molecular movement in a low temperature environment, as a result of which, sufficient elasticity cannot be obtained. However, by treating the fluorine-containing rubber with the compound of the present invention, the elasticity in the low temperature environment can be increased while maintaining other properties such as chemical resistance and heat resistance, it can be improved elasticity at low temperature environment. Although the present invention is not limited by theory, the reason for improving of elasticity property in the low temperature environment by treating the fluorine-containing rubber with the compound of the present invention may be considered as follows. The compound of the present invention may have a group having high molecular mobility and a flexible skeleton as a substituent, for example, a perfluoropolyalkylether group. By reacting the compound with the moiety (for example, double bond, triple bond) reactive with the fluorine-containing rubber and grafting them, the molecular mobility of fluorine rubber itself is increased, as a result, sufficient elasticity can be achieved in the low temperature environment. In addition, by applying a group having excellent chemical resistance and heat resistance as the substituent which the compound of the present invention, for example by applying a perfluoroalkylether group, the chemical resistance and heat resistance of the fluorine-containing rubber can be maintained.

The present invention provides a low temperature property rubber prepared by using the composition of the present invention.

In one embodiment, the composition of the present invention is used as a raw material of a liquid rubber.

The composition of the present invention used as the raw material of a liquid rubber (hereinafter, referred to as "Liquid rubber raw composition 1") contains at least one polymer having a group of the formula (Ib) at the terminal of the main chain of the present invention.

By mixing Liquid rubber raw composition 1 with a composition containing a compound having an unsaturated bond (hereinafter, "Liquid rubber raw composition 2"), a click-reaction between the nitrileoxide group contained in the compound of the present invention and the unsaturated bond contained in the compound in Liquid rubber raw composition 2 occurs to produce a gel-like production (that is, a liquid rubber).

Examples of the compound having an unsaturated bond in contained in Liquid rubber raw composition 2 include, but are not limited to, one or more compounds of the formula:

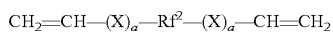

wherein:
X is each independently —CH$_2$—, —CH$_2$O—, —CH$_2$OCH$_2$—, or —CH$_2$—NR$^1$—CO—;
Y is —CH$_2$—;
Rf$^1$ is a di-valent perfluoroalkylene group; and
a is each independently an integer of 0 or 1;
and
one or more compounds of the formula:

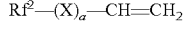

wherein:
X is each independently —CH$_2$—, —CH$_2$O—, —CH$_2$OCH$_2$— or —CH$_2$—NR$^1$—CO—;
Y is —CH$_2$—:
Rf$^2$ is a perfluoropolyalkyl group; and
a is each independently an integer of 0 or 1.

Specific examples of the compound having an unsaturated bond contained in Liquid rubber raw composition 2 include, for example, triallyl isocyanurate (TAIC), triallyl trimellitate, diallyl phthalate, triallyl phosphite, N,N-diallyl acrylamide, 1,6-vinyl dodecafluorohexane, bismaleimide, triallyl phosphate, and the like.

In the conventional producing of a liquid rubber, a metal catalyst such as a platinum compound was essential. However, the present invention has an advantage to be able to produce a liquid rubber simply by mixing Liquid rubber raw composition 1 and Liquid rubber raw composition 2. By using the composition of the present invention, a catalyst-free liquid rubber can be produced. For example, such liquid rubber can be suitably used in the semiconductor manufacturing process on which the presence of the metal can adversely affect.

In the conventional producing of a liquid rubber, a curing reaction is performed by hydrosililation, and a liquid rubber obtained by this method contains Si atom. This backbone containing Si atom has low resistance against a fluorine active species (a fluorine gas, a fluorine plasma, a fluorine radical) and is not suitable for use in a step in which the active species is generated in the semiconductor manufacturing process. Since the liquid rubber obtained by using the composition of the present invention is produced without using a backbone containing Si atom, the liquid rubber containing no Si atom can be easily produced if necessary. In this point, the present invention is advantageous.

In addition, the present invention provides a liquid rubber produced by using the composition of the present invention.

In one embodiment, the composition of the present invention is used as a raw material of a thermosetting polymer material (a resin or a rubber).

The composition (hereinafter, also referred to as "a "thermosetting polymer material raw material composition 1") used as a thermosetting polymer material contains any of at least one polymer of the formula (Ia), at least one polymer having a monomer unit of the formula (IIa), at least one polymer having a group of the formula (Ib) at the terminal of the present invention. In a preferable embodiment, the compound of the present invention used herein is a material having both a group which is reactive with a nitrileoxide group under high temperature (for example, C=C bond, CN bond, CC) and a nitrileoxide group in the skeleton.

The thermosetting polymer material raw material composition 1 may be a composition comprising at least one material reactive with a nitrileoxide group. The material having reactivity with the nitrileoxide group is not limited as long as the material is a polymer having a moiety reactive with the nitrileoxide group (preferably, C=C, C≡N). The moiety reactive with the nitrileoxide group may be in the backbone itself of the polymer, or when the moiety is absent, a substituent having moiety reactive with the nitrileoxide group may be introduced into the polymer.

The material having reactivity with the nitrileoxide group is not particularly limited, and may be for example, a polymer having a moiety reactive with a nitrileoxide group, for example, a general-purpose rubber, a natural rubber, a polynorbornene, a fluoropolymer (preferably, that obtained by polymerizing fluoroolefins or fluorine-containing (metha)acrylates, particularly preferably, a fluorine rubber).

Examples of the general-purpose rubber include, for example, NBR (nitrile rubber), EPDM (ethylene-propylene-diene copolymer rubber), PAN (polyacrylonitrile), $H_2C=C(R)-(CH_2-CHR)_n-CH_2-CR=CH_2$ (wherein R is each independently a hydrogen atom, a methyl group, an ethyl group, or an isobutyl group, and n is an integer of 10-1000).

The natural rubber is a rubbery polymer naturally occurring in normal, and usually has a polyisoprene structure, although is not limited thereto.

The fluorine-containing (meth) acrylates are a compound of $H_2C=C(X)-CO-O-Y$, wherein X is a hydrogen atom, a methyl group, an ethyl group, a trifluoromethyl group, a fluorine atom, or a chlorine atom, and Y is a linear or branched alkyl group having at least one a fluoro group, preferably an alkyl group comprising a skeleton of a perfluoroalkylene group or a perfluoroalkyl group, particularly preferably, $-CH_2(CF_2)_nH$, $-CH_2CH_2(CF_2)_nF$.

The fluorine rubber may be either a non-perfluoro fluorine rubber or a perfluoro fluorine rubber, for example, and preferably has a structural unit derived from at least one monomer selected from the group consisting of tetrafluoroethylene (TFE), vinylidene fluoride (VdF) and a perfluoroethylenically unsaturated compound (for example, hexafluoropropylene (HFP), perfluoro(alkyl vinyl ether) (PAVE), and the like) of the following formula (a):

$$CF_2=CF-Rf^a \quad (a)$$

wherein $Rf^a$ represents $-CF_3$ or $ORf^b$ wherein $Rf^b$ represents a perfluoroalkyl group having 1-5 carbon atoms.

Examples of the non-perfluoro fluorine rubber include a vinylidene fluoride (VdF) fluorine rubber, tetrafluoroethylene (TFE)/propylene (Pr) fluorine rubber, tetrafluoroethylene (TFE)/propylene (Pr)/vinylidene fluoride (VdF) fluorine rubber, ethylene (Et)/hexafluoropropylene (HFP) fluorine rubber, ethylene (Et)/hexafluoropropylene (HFP)/vinylidene fluoride (VdF) fluorine rubber, ethylene (Et)/hexafluoropropylene (HFP)/tetrafluoroethylene (TFE) fluorine rubber, fluorosilicone fluorine rubber and fluorophosphazene fluorine rubber. They can be used alone or in combinations. In addition, these fluorine rubbers may be a copolymer with co-monomer.

The co-monomer is not particularly limited as long as it can copolymerize with other monomer, and include, for example, TFE, HFP, PAVE, chlorotrifluoroethylene (CTFE), trifluoroethylene, trifluoropropylene, tetrafluoropropylene, pentafluoropropylene, trifluorobutene, tetrafluoroisobutene, hexafluoroisobutene, vinyl fluoride, an iodine-containing and fluorine-containing vinyl ether, perfluorovinyl ether such as a fluorine-containing monomer of the formula (b):

$$CH_2=CFRf^b \quad (b)$$

wherein $Rf^b$ is a straight or branched fluoroalkyl group having 1-12 carbon atoms;
a fluorine-containing monomer (c);

$$CF_2=CFOCF_2ORf^c \quad (c)$$

wherein $Rf^c$ is a straight or branched perfluoroalkyl group having 1-6 carbon atoms, a cyclic perfluoroalkyl group having 5-6 carbon atoms or a straight or branched perfluorooxyalkyl group having 1-3 oxygen atoms and 2-6 carbon atoms; a fluorine-free monomer such as ethylene (Et), propylene (Pr), alkyl vinyl ether; and, a reactive emulsifier. They can be used alone or in combination with two or more.

Examples of the copolymer include, but are not particularly limited to, for example, at least one copolymer selected from the group consisting of a VdF/HFP copolymer, a VdF/TFE/HFP copolymer, a VdF/CTFE copolymer, a VdF/CTFE/TFE copolymer, a VdF/PAVE copolymer, a VdF/TFE/PAVE copolymer, a VdF/HFP/PAVE copolymer, a VdF/HFP/TFE/PAVE copolymer, a VdF/TFE/propylene(Pr) copolymer, a VdF/ethylene(Et)/HFP copolymer and a copolymer of VdF/the fluorine-containing monomer (b) of the formula (b).

The reactive site with a nitrileoxide group in the fluorine rubber may be derived from a monomer having the reactive site or may be introduced by modifying a fluorine rubber having no reactive site.

Examples of the monomer having a reactive site with a nitrileoxide group include, for example, a bisolefin compound of the formula:

$$R^{22}R^{23}C=CR^{24}-Z-CR^{25}=CR^{26}R^{27}$$

wherein $R^{22}$, $R^{23}$, $R^{24}$, $R^{25}$, $R^{26}$ and $R^{27}$ are same or difference, and are independently represent a hydrogen atom or an alkyl group having 1-5 carbon atoms; and Z represents a straight or branched alkylene or an cycloalkylene group having 1-18 carbon atoms which may have an oxygen atom and preferably fluorinated at least partially, or a (per) fluoropolyoxyalkylene group.

Other examples of the monomer having a reactive site with a nitrileoxide group include an olefin compound having a nitrile group, for example, a compound of the formula:

$$R^{28}R^{29}C=CR^{30}-Z-CN$$

wherein $R^{28}$, $R^{29}$ wherein and $R^{30}$ are same or different, and independently represent a hydrogen atom or an alkyl group having 1-5 carbon atoms; and Z represents a straight or branched alkylene or an cycloalkylene group having 1-18 carbon atoms which may have an oxygen atom and preferably fluorinated at least partially or a (per) fluoropolyoxyalkylene group, representatively, $CF_2=CFOCF_2CF(CF_3)OCF_2CF_2CN$.

Another examples of the monomer having a reactive site with a nitrileoxide group include acrylonitrile, 5-ethylidene-2-norbornene, and a styrene derivative having a nitrile group on the aromatic ring.

The thermosetting polymer material raw material composition 1 can be used in the form containing a solvent, but can be usually used in the form containing no solvent.

The thermosetting polymer material raw material composition 1 causes a curing reaction by the increasing of the temperature. The environment of the curing reaction is not limited as long as the temperature can be increased, and, the curing reaction is performed, for example, in a mold, in a molding machine, in an oven, on a hot stage, in a mortar, or the like.

The reaction temperature for causing a curing reaction is not particularly limited, and is preferably a temperature higher than the glass transition temperature, more preferably the melting point of at least one of the polymeric materials forming the thermosetting polymer material raw material composition 1.

The thermosetting polymer material raw material composition 1 can have a design to provide a material having higher thermal and chemical resistance than those of a conventional thermosetting polymer, as needed. This is due to the fact that the nitrileoxide groups crosslink while forming a chemically robust bond.

The curing reaction of the thermosetting polymer material raw material composition 1 can be also caused in the presence of additives or reagents for advancing and facilitating the reaction, or can be also caused in the absence of the additives or reagents.

Hereinbefore, the present invention is described in detail, although the present is not limited to these compounds and uses.

EXAMPLE

Example 1: Preparation of dihydroxydiphenyl nitrileoxide

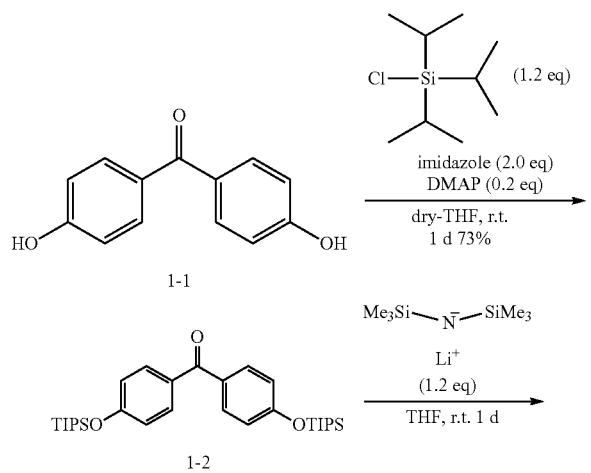

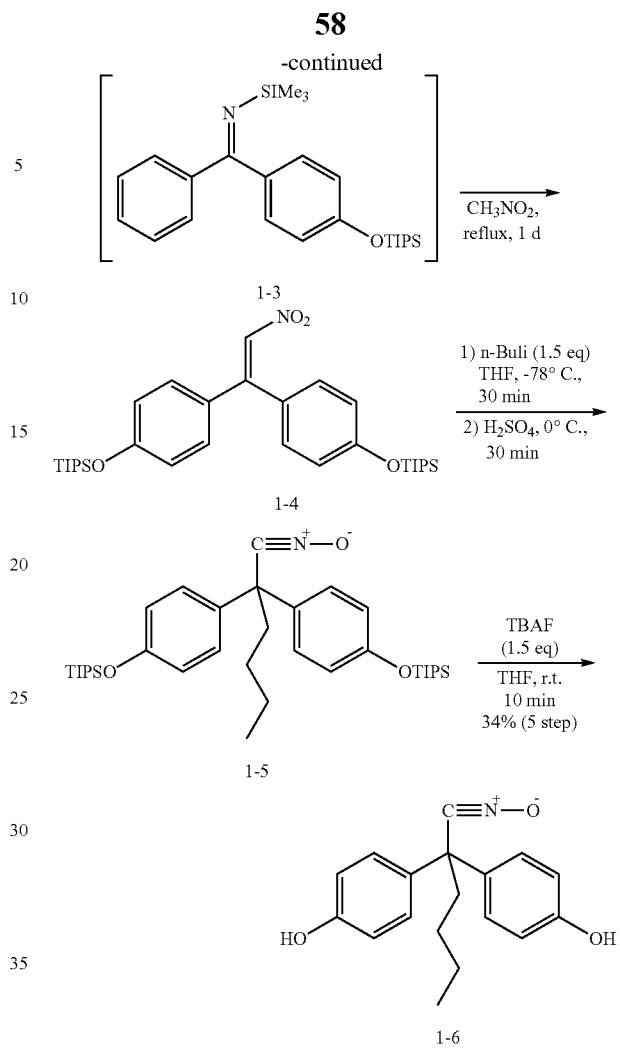

Preparation of triisopropylsilyl(TIPS) benzophenone 1-2

Dihydroxybenzophenone 1-1 (17 g, 78 mmol), imidazole (20 g, 300 mmol), and N,N-dimethyl-4-aminopyridine (DMAP: 4.1 g, 32 mmol) were dissolved in anhydrous tetrahydrofuran (THF: 400 mL), and triisopropylsilyl chloride (33 g, 170 mmol) was added at 0° C. Then, the reaction mixture was stood for 1 day at a room temperature. The solvent was evaporated under reduced pressure, and dichloromethane was added. The mixture was separated with water, and dried. The solvent was evaporated under reduced pressure, and the residue was purified a silica gel column chromatography (ethyl acetate:hexane=1:50) to obtain a colorless transparent oil (30 g, 60 mmol, 73%).

$^1$H NMR (400 MHz, 298 K, $CDCl_3$): δ 7.74-7.71 (d, J=8.0 Hz, 4H), 6.94-6.92 (d, J=8.0 Hz, 4H), 1.32-1.26 (m, 6H), 1.13-1.11 (d, J=8.0 Hz, 36H) ppm Preparation of TIPS diphenylnitroethene 1-4

TIPS benzophenone 1-2 (21 g, 40 mmol) was added to THF (40 mL), and cooled to 0° C. under Ar atmosphere. Lithium bis(trimethylsilyl)amide (48 mL, 48 mmol) was added, and stirred for one day at a room temperature. The solvent was evaporated under reduced pressure, and ethyl acetate was added. The reaction mixture was separated with water, saturated saline solution. The solvent was evaporated under reduced pressure, and nitromethane (40 mL) was added. The mixture was refluxed at 115° C. for one day. The solvent was distilled off to obtain a brown oil. This compound was purified by a flash column chromatography to an orange oil. This was used in the next reaction.

Preparation of TIPS diphenyl nitrileoxide 1-5

The crude TIPSdiphenylnitroethene 1-4 was added to anhydrous THF (400 mL), and cooled to −78° C. under Ar atmosphere. n-BuLi (38 mL, 60 mmol) was added, and stirred for 30 minutes. A concentrated sulfuric acid (>95%, 20 mL, 400 mmol) was added, and stirred as 0° C. for 30 minutes. The mixture was separated with water, and dried. The solvent was removed under a reduced pressure to obtain an orange oil. This was used in the next reaction.

Preparation of dihydroxydiphenyl nitrileoxide 1-6

The crude TIPS diphenyl nitrileoxide 1-5 was dissolved in THF (480 mL), and tetra-n-butylammonium fluoride (TBAF: 73 mL, mmol) was added and stirred for 10 minutes. Dichloromethane was added at an appropriate amount, separated with water and saturated saline solution, and dried. The solvent was evaporated under reduced pressure, and the residue was purified by a silica gel column chromatography (hexane→hexane:ethyl acetate=8:1→4:1→2:1) to obtain a yellow oil (4.1 g, 14 mmol, 34%).

$^1$H NMR (400 MHz, 298 K, CDCl$_3$): δ 7.05-7.03 (d, J=8.0 Hz, 4H), 6.77-6.75 (d, J=8.0 Hz, 4H), 2.28-2.25 (t, J=7.0 Hz, 4H), 1.28 (m, 4H), 0.86-0.83 (t, J=7.0 Hz, 3H) ppm Example 2: Condensation Polymerizing Reaction Using Dihydroxydiphenyl Nitrileoxide

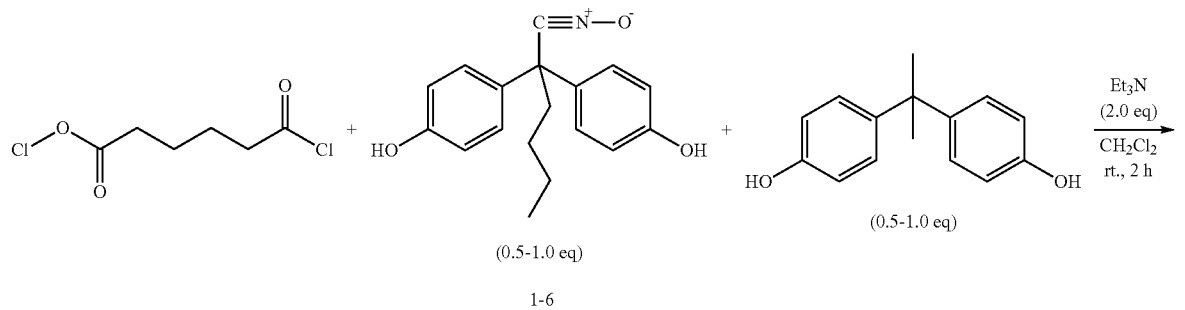

1-6

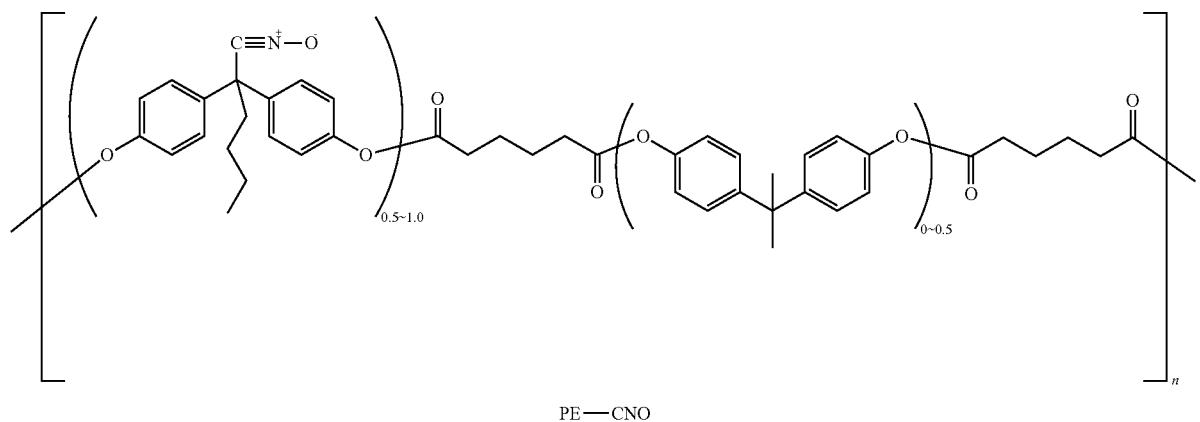

PE—CNO

Preparation of PE-CNO-5

Dihydroxydiphenyl nitrileoxide 1-6 (0.15 g, 0.50 mmol) and bisphenol A (0.11 g, 0.50 mmol) was added to dehydrated dichloromethane (1.0 mL), and triethylamine (0.44 mL, 4.0 mmol) was added while stirring at 0° C. Then, a solution which adipoyl chloride (0.18 g, 0.1 mmol) was dissolved in chloroform (1 mL) was added slowly, and then stirred for 2 hours at a room temperature. The product was reprecipitated in methanol, and ether. The resulting pale yellow solid was dissolved in chloroform, separated with water, and dried. The solvent was evaporated under reduced pressure to obtain a pale yellow solid (200 mg, 47%).

Yield, 39%
Number average molecular weight (GPC), 14,000
$M_w/M_n$ (GPC), 2.5
Copolymerization Ratio ($^1$H NMR), 1:1
$^1$H NMR (400 MHz, 298 K, CDCl$_3$): δ 7.29-7.27 (d, J=8.4 Hz, 4H, Ph-), 7.21-7.20 (d, J=8.4 Hz, 4H, Ph-), 7.08-7.06 (d, J=8.4 Hz, 4H, Ph-), 6.98-6.96 (d, J=8.4 Hz, 4H, Ph-), 2.61 (m, 8H, —C$\underline{H_2}$CH$_2$CH$_2$C$\underline{H_2}$—), 2.34 (m, 2H, —C$\underline{H_2}$CH$_2$CH$_2$CH$_3$), 1.86 (m, 8H, —CH$_2$C$\underline{H_2}$C$\underline{H_2}$CH$_2$—), 1.65 (m, 6H, C(C$\underline{H_3}$)$_2$), 1.34 (m, 4H, —CH$_2$C$\underline{H_2}$C$\underline{H_2}$CH$_3$), 0.88 (m, 3H, —CH$_2$CH$_2$CH$_2$C$\underline{H_3}$) ppm

Preparation of PE-CNO-10

Dihydroxydiphenyl nitrileoxide 1-6 (0.30 g, 1.00 mmol) was added to dehydrated dichloromethane (1.0 mL), and triethylamine (0.44 mL, 4.0 mmol) was added while stirring at 0° C. Then, a solution which adipoyl chloride (0.18 g, 0.1 mmol) was dissolved in chloroform (1 mL) was added slowly, and then stirred for 2 hours at a room temperature. The product was reprecipitated in methanol, and ether. The resulting pale yellow solid was dissolved in chloroform, separated with water, and dried. The solvent was evaporated under reduced pressure to obtain a pale yellow solid (200 mg, 47%).

Yield, 47%
Number average molecular weight (GPC), 15000
$M_w/M_n$, 3.4
$^1$H NMR (400 MHz, 298 K, CDCl$_3$): δ 7.30-7.28 (d, J=7.8 Hz, 4H, Ph-), 7.09-7.07 (d, J=7.8 Hz, 4H, Ph-), 2.63 (m, 4H, —C$\underline{H_2}$CH$_2$CH$_2$C$\underline{H_2}$—), 2.34 (m, 2H, —C$\underline{H_2}$CH$_2$CH$_2$CH$_3$), 1.77 (m, 4H —CH$_2$C$\underline{H_2}$C$\underline{H_2}$CH$_2$—), 1.34 (m, 4H, —CH$_2$C$\underline{H_2}$C$\underline{H_2}$CH$_3$), 0.89 (m, 3H, —CH$_2$CH$_2$CH$_2$C$\underline{H_3}$) ppm

Example 3: Click Reaction of PE-CNO and allyl Trimethylsilane

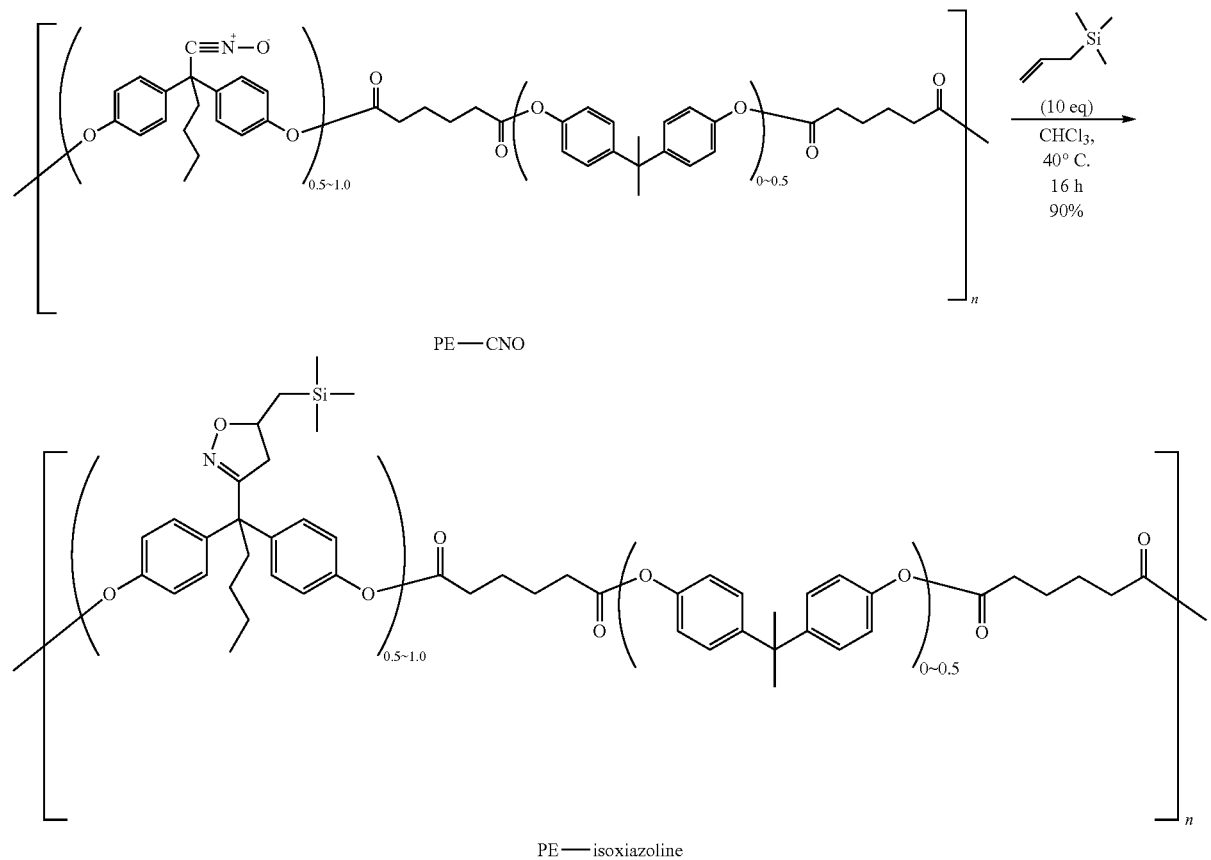

Preparation of PE-isoxazoline-5

PE-CNO-10 (25 mg, 0.057 mmol) and allyl trimethylsilane (65 mg, 0.57 mmol) were dissolved in chloroform (0.5 mL), and stirred for 16 hour at 40° C. The solvent and unreacted allyl trimethylsilane were evaporated to obtain a yellow solid.

$^1$H NMR (400 MHz, 298 K, CDCl$_3$): δ 7.28-7.26 (d, J=7.8 Hz, 4H, Ph-), 7.22-7.20 (d, J=7.8 Hz, 4H, Ph-), 7.07-7.05 (d, J=7.8 Hz, 4H, Ph-), 6.98-6.96 (d, J=8.4 Hz, 4H, Ph-), 4.58 (m, 1H, —CNOC$\underline{H}$CH$_2$—), 2.63 (m, 8H, —C$\underline{H_2}$CH$_2$CH$_2$—), 2.36 (m, 2H, —C$\underline{H_2}$CH$_2$CH$_2$CH$_3$), 2.21 (m, 2H, —CNOCH<u>CH$_2$</u>—), 1.88 (m, 8H, —CH$_2$<u>CH$_2$CH$_2$</u>CH$_2$—), 1.65 (m, 6H, C(<u>CH$_3$</u>)$_2$), 1.43 (m, 2H, —CH$_2$<u>CH$_2$</u>CH$_2$CH$_3$), 1.08 (m, 4H, —CH$_2$CH$_2$CH$_2$CH$_3$, —<u>CH$_2$</u>Si(CH$_3$)$_3$), 0.81 (m, 3H, —CH$_2$CH$_2$CH$_2$<u>CH$_3$</u>), 0 (s, 9H, Si(<u>CH$_3$</u>)$_3$) ppm Preparation of PE-isoxazoline-10

PE-CNO-10 (25 mg) and allyl trimethylsilane (65 mg, 0.57 mmol) were dissolved in chloroform (0.5 mL), and stirred for hour at 40° C. The solvent and unreacted allyl trimethylsilane were evaporated to obtain a pale yellow solid.

$^1$H NMR (400 MHz, 298 K, CDCl$_3$): δ 7.30-7.28 (d, J=7.8 Hz, 4H, Ph-), 7.07-7.05 (d, J=7.8 Hz, 4H, Ph-), 4.59 (m, 1H, —CNO<u>CH</u>CH$_2$—), 2.65 (m, 4H, —<u>CH$_2$</u>CH$_2$CH$_2$<u>CH$_2$</u>—), 2.34 (m, 2H, —<u>CH$_2$</u>CH$_2$CH$_2$CH$_3$), 2.23 (m, 2H, —CNOCH<u>CH$_2$</u>—), 1.89 (m, 4H, —CH$_2$CH$_2$<u>CH$_2$</u>CH$_2$—), 1.34 (m, 2H, —CH$_2$<u>CH$_2$</u>CH$_2$CH$_3$), 1.08 (m, 4H, —CH$_2$CH$_2$<u>CH$_2$</u>CH$_3$, —CH$_2$Si(CH$_3$)$_3$), 0.80 (m, 3H, —CH$_2$CH$_2$CH$_2$<u>CH$_3$</u>), 0 (s, 9H, Si<u>CH$_3$</u>) ppm Example 4: Crosslinking Reaction of Natural Rubber by PE-CNO

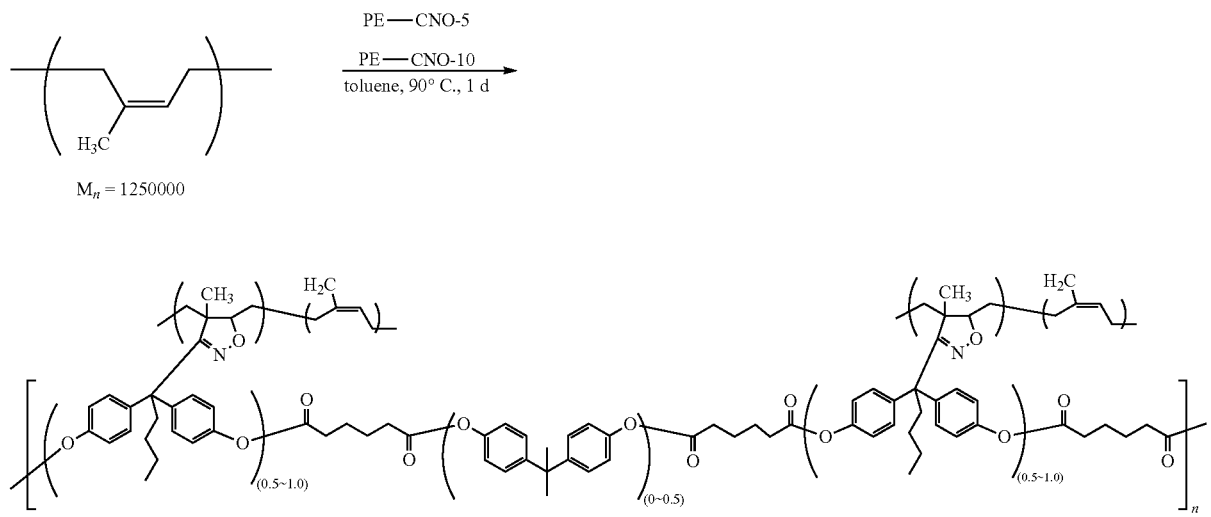

Crosslinking Reaction by PE-CNO-5

A natural rubber was dissolve in toluene, and PE-CNO-5 was added and reacted at 90° C. The produced polymer was immersed in chloroform for one day, and dried under air at a room temperature and under vacuum at 70° C. to obtain a pale yellow network polymer (53%).

Yield: 53%

Degree of swelling (CHCl$_3$): 5700

Crosslinking Reaction by PE-CNO-10

A natural rubber (67 mg) was dissolve in toluene (1 mL), PE-CNO-10 (7.0 mg) was added and reacted at 90° C. The produced polymer was immersed in chloroform for one day, and dried under air at a room temperature and under vacuum at 70° C. to obtain a pale yellow network polymer (39 mg, 53%).

Yield: 67%

Degree of swelling (CHCl$_3$): 3700%

Example 5: Preparation of OH diphenyl nitrileoxide

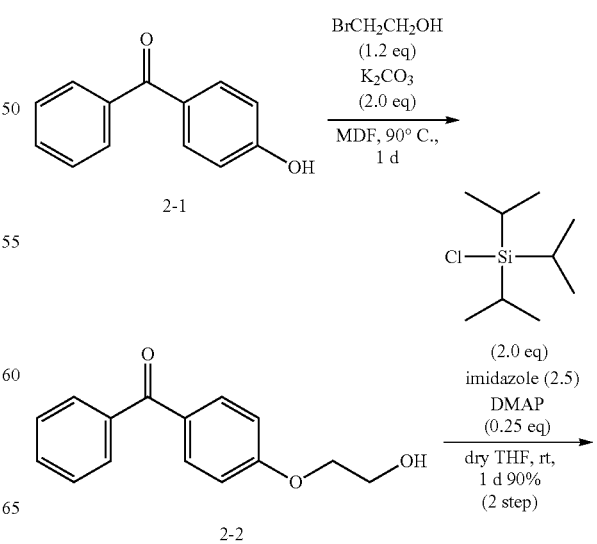

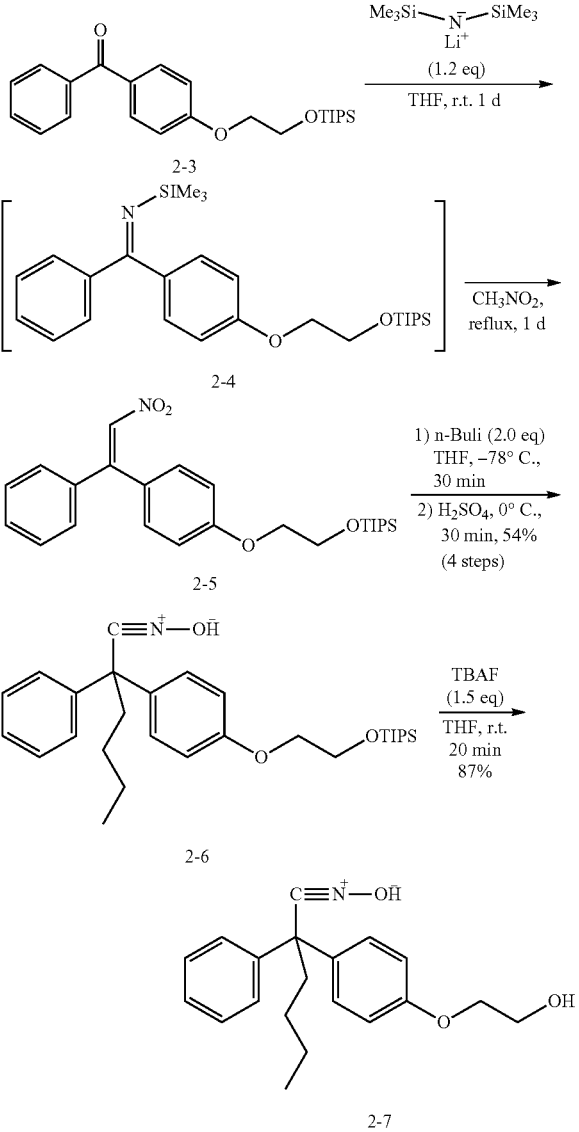

Preparation of OH benzophenone 2-2

4-hydroxy benzophenone (9.9 g, 50 mmol), 2-bromoethanol (7.5 g, 60 mmol) and potassium carbonate (10 g, 75 mmol) were added to N,N-dimethylformamide (DMF, 150 mL), and stirred at 90° C. for one day. A solvent was distilled off, and dichloromethane was added. The mixture extracted with water and saturated saline solution, and dried. A solvent was distilled off to obtain a pale yellow powder (crude yield 12 g). This compound was used in the next reaction.

Preparation of TIPS benzophenone 2-3

The crude 2-2 (12 g), imidazole (8.5 g, 130 mmol), and DMAP (1.5 g, 1.3 mmol) were dissolved in anhydrous THF (250 mL), and triisopropylsilyl chloride (19 g, 100 mmol) was added at 0° C. The mixture was returned to a room temperature and reacted for one day. The solvent was evaporated under reduced pressure. The dichloromethane was added and separated with water, and dried. The solvent was evaporated under reduced pressure. The residue was purified by a silica gel column chromatography (ethyl acetate:hexane=1:30) to obtain a pale oil (22 g, 45 mmol, 90%).

Preparation of TIPS diphenylnitroethene 2-5

TIPS benzophenone 2-3 (11 g, 23 mmol) was added to THF (20 mL), and cooled to 0° C. under Ar atmosphere. Lithium bis(trimethylsilyl)amide (19 mL, 25 mmol) was added, and stirred at a room temperature for one day. The solvent was evaporated under reduced pressure, and ethyl acetate was added. The mixture was separated with water and saturated saline solution. The solvent was evaporated under reduced pressure. Nitromethane (25 mL) was added, and refluxed at 115° C. for one day. A solvent was distilled off to obtain a brown oil. This compound was used in the next reaction.

Preparation of TIPS diphenyl nitrileoxide 2-6

The crude 2-5 (14 g) was added to anhydrous THF (350 mL), and cooled at −78° C. under Ar atmosphere. n-BuLi (25 mL, 64 mmol) was added, and stirred for 30 minutes. A concentrated sulfuric acid (>95%, 17 mL, 320 mmol) was added, stirred at 0° C. for 30 minutes. The mixture was separated water, and dried. The solvent was evaporated under reduced pressure. The residue was purified by a silica gel column chromatography (dichloromethane:hexane=1:2) to obtain a yellow oil (5.8 g, 12 mmol, 54%).

Preparation of OH diphenyl nitrileoxide 2-7

TIPS diphenyl nitrileoxide 2-6 (2.0 g, 4.5 mmol) was dissolve in THF (50 mL), and TBAF (1.7 mL, 6.7 mmol) was added and stirred for 20 minutes. Dichloromethane was added, and the mixture was separated with water and saturated saline solution, and dried. The solvent was evaporated under reduced pressure. The residue was purified by a silica gel column chromatography (dichloromethane:hexane=10:1) to obtain a yellow oil (2.6 g, 8.2 mmol, 97%).

$^1$H NMR (400 MHz, 298 K, CDCl$_3$): δ 7.37-7.28 (m, J=8.7 Hz, 5H), 7.18-7.16 (d, J=8.7 Hz, 2H), 6.82-6.80 (d, J=8.7 Hz, 2H), 5.16 (s, 1H), 2.38-2.34 (t, J=6.8 Hz, 2H), 1.37 (m, 4H), 0.93-0.89 (t, J=6.8 Hz, 3H) ppm

Example 6: Ring-Opening Polymerization Using OH diphenyl nitrileoxide as an Initiator

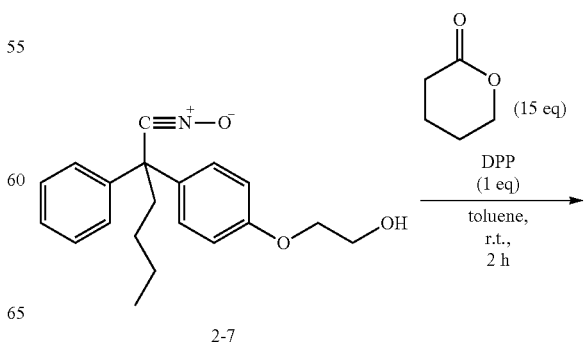

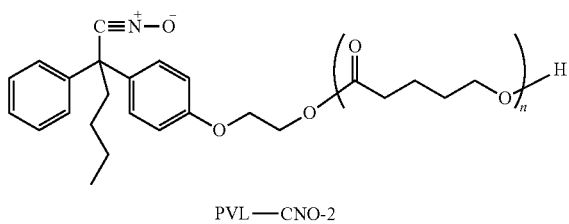

PVL—CNO-2

Preparation of macromolecular nitrileoxide PVL-CNO-2

5-valerolactone (0.96 g, 9.6 mmol) and OHdiphenyl nitrileoxide 3-6 (0.20 g, 0.64 mmol) were added to dehydrated toluene (5 mL), and diphenyl phosphate (0.16 g, 0.64 mmol) was added while stirring at a room temperature, and stirred for 2 hours. Reprecipitation in hexane:ethanol=(9:1) (100 mL) and filtration were repeated two times to obtain a white solid 0.83 g (72%). As a result of the GPC measurement, unimodal peak (Mn=6100, Mw/Mn=1.21) was observed.

$^1$H NMR (400 MHz, 298 K, CDCl$_3$): δ 7.34-7.26 (m, 5H, Ph-) 7.22-7.20 (d, J=8.0 Hz, 2H, Ph-), 6.88-6.86 (d, J=8.0 Hz, 2H, Ph-), 4.44-4.42 (t, J=4.0 Hz, 2H, —OCH$_2$CH$_2$O—), 4.17 (m, 2H, —OCH$_2$CH$_2$O—), 4.08 (m, 62H, —CH$_2$CH$_2$OCO—) 3.67-3.64 (t, J=6.0, 2H, —CH$_2$CH$_2$OH), 2.34 (m, 64H, —OCOCH$_2$CH$_2$—, —CH$_2$CH$_2$CH$_3$), 1.68 (m, 124H, —CH$_2$CH$_2$CH$_2$CH$_2$—), 1.35 (m, 4H, —CH$_2$CH$_2$CH$_3$), 0.90-0.87 (m, J=6.0, 3H, —CH$_2$CH$_2$CH$_2$CH$_3$) ppm

Example 7: Click Reaction of PVL-CNO-2 and allyl Trimethylsilane

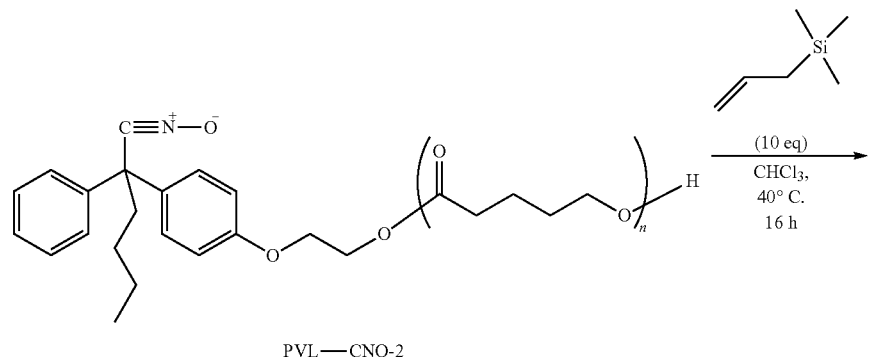

PVL—CNO-2

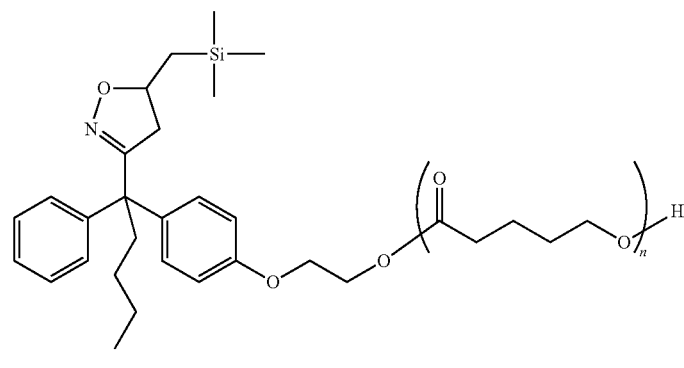

PVL-isoxazoline

Preparation of PVL-isoxazoline

PVL-CNO-2 (75 mg, 0.022 mmol) and allyl trimethylsilane (25 mg, 0.22 mmol) were dissolved in chloroform (0.5 mL), and stirred at 40° C. for one day. The solution was reprecipitated in hexane (50 mL) to obtain a white solid.

$^1$H NMR (400 MHz, 298 K, CDCl$_3$): δ 7.32-7.18 (m, 7H), 6.87-6.85 (d, J=8.0 Hz, 2H), 4.59 (m, 1H), 4.45-4.43 (t, J=4.0 Hz, 2H), 4.26 (m, 2H), 4.09 (m, 60H) 3.67-3.64 (t, J=6.0, 2H), 2.77-2.71 (m, 1H) 2.40-2.32 (m, 61H), 1.69-1.67 (m, 120H), 1.28-1.24 (m, 2H), 1.10-1.08 (m, 3H) 0.85-0.79 (m, 4H), 0.00 (s, 9H) ppm

Example 8

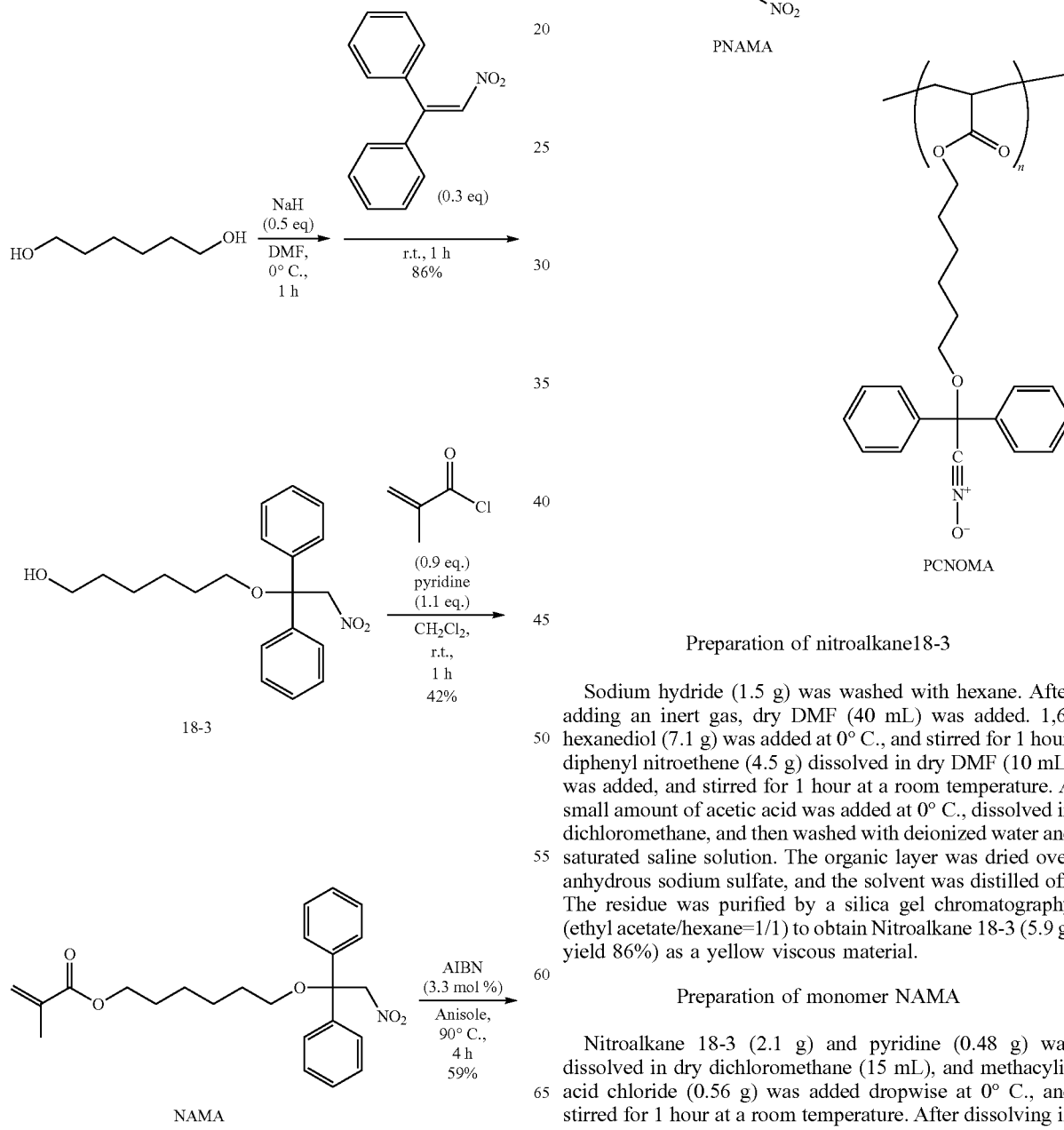

Preparation of nitroalkane18-3

Sodium hydride (1.5 g) was washed with hexane. After adding an inert gas, dry DMF (40 mL) was added. 1,6-hexanediol (7.1 g) was added at 0° C., and stirred for 1 hour. diphenyl nitroethene (4.5 g) dissolved in dry DMF (10 mL) was added, and stirred for 1 hour at a room temperature. A small amount of acetic acid was added at 0° C., dissolved in dichloromethane, and then washed with deionized water and saturated saline solution. The organic layer was dried over anhydrous sodium sulfate, and the solvent was distilled off. The residue was purified by a silica gel chromatography (ethyl acetate/hexane=1/1) to obtain Nitroalkane 18-3 (5.9 g, yield 86%) as a yellow viscous material.

Preparation of monomer NAMA

Nitroalkane 18-3 (2.1 g) and pyridine (0.48 g) was dissolved in dry dichloromethane (15 mL), and methacylic acid chloride (0.56 g) was added dropwise at 0° C., and stirred for 1 hour at a room temperature. After dissolving in chloroform, the mixture was washed with saturated saline solution. The organic layer was dried over anhydrous sodium sulfate, and the solvent was distilled off. The residue was purified by a silica gel chromatography (chloroform/hexane=3/1) to obtain a colorless clear liquid NAMA (1.0 g, yield 42%).

$^1$H NMR (300 MHz, CDCl$_3$, ppm) δ 7.67-7.24 (m, 10H, Ph), 6.09 (s, 1H, H$_2$C=C), 5.43 (s, 1H, H$_2$C=C), 5.34 (s, 2H, CH$_2$NO$_2$), 4.13 (t, 2H, J=6.7 Hz, OCH$_2$), 4.13 (t, 2H, J=6.7 Hz, C=OOCH$_2$), 3.56 (t, 2H, J=6.2 Hz, OCH$_2$), 1.94 (s, 1H, C=CCH$_3$), 1.72-1.60 (m, 4H, OCH$_2$CH$_2$), 1.50-1.31 (m, CH$_2$CH$_2$)

Preparation of PNAMA by Free Radical Polymerization

[M]/[I]=33, [M]=0.6M wherein M is NAMA, and I is AIBN.

NAMA (0.5 g), azobisisobutyronitrile (AIBN) (6.0 mg), anisole (2.0 mL) was added to a reactor. After freeze-degassing three times, the mixture was stirred at 90° C. for 4 hours. Reprecipitation in hexane/ethanol=9/1 was performed three times to obtain a white solid (0.29 g).

$^1$H NMR (400 MHz, CDCl$_3$, ppm): δ 7.3 (m, 10H, Ph-H), 5.3 (s, 2H, —C(Ph)$_2$-CH$_2$—NO$_2$), 3.9 (br, 2H, —C(O)O—CH$_2$—), 3.4 (br, 2H, —C(Ph)$_2$-O—CH$_2$—), 2.1-0.8 (m, 13H, —O—C$_4$H$_8$—O—, —CH$_2$—C(CH$_3$)—C(O)—)

Preparation of PCNOMA

PNAMA (0.18 g), dry dichloromethane 10 mL, p-chlorophenyl isocyanate (0.67 g) and triethylamine (0.68 g) was added under an inert gas, and stirred for 2 hours at a room temperature. The insoluble portion was filtered off, and the solvent was evaporated. Reprecipitation in hexane/ethanol=9/1 was performed three times to obtain a white solid (42 mg, yield 23%).

$^1$H NMR (400 MHz, CDCl$_3$, ppm): δ 7.3 (m, 10H, Ph-H), 3.9 (br, 2H, —C(O)O—CH$_2$—), 3.4 (br, 2H, —C(Ph)$_2$-O—CH$_2$—), 2.1-0.7 (m, 13H, —O—C$_4$H$_8$—O—, —CH$_2$—C(CH$_3$)—C(O)—)

INDUSTRIAL APPLICABILITY

The compound of the present invention can be suitably used in various applications, for example, hydrophilizing agent, surface treating agent, polymerization initiator, polymerizable monomer, a crosslinking agent, denaturation treatment agent, thermosetting resin, thermosetting elastomer, liquid rubber, low temperature property rubber, modifier of filler or reactive compatibilizing agent.

What is claimed is:

1. A compound of the formula (III):

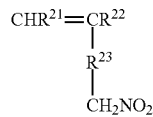

wherein:

R$^{21}$ is a hydrogen atom or an alkyl group;

R$^{22}$ is a hydrogen atom or an alkyl group; and

R$_{23}$ is —R$^{24}$—R$^{25}$—R$^{26}$—;

R$^{24}$ is —CO—O—;

R$^{25}$ is a linker having 1-20 atoms of the main chain;

R$_{26}$ is —CR$^{27}$R$^{28}$—; and

R$^{27}$ and R$^{28}$ are each independently an aryl group having 5-10 carbon atoms.

* * * * *